US010267787B2

(12) United States Patent
Bearss et al.

(10) Patent No.: US 10,267,787 B2
(45) Date of Patent: *Apr. 23, 2019

(54) PROFILING PEPTIDES AND METHODS FOR SENSITIVITY PROFILING

(71) Applicant: Tolero Pharmaceuticals, Inc., Lehi, UT (US)

(72) Inventors: David J. Bearss, Alpine, UT (US); Adam Siddiqui-Jain, South Jordan, UT (US); Clifford J. Whatcott, West Jordan, UT (US); Peter W. Peterson, Salt Lake City, UT (US); Steven L. Warner, Sandy, UT (US); Lars Mouritsen, Lehi, UT (US)

(73) Assignee: Tolero Pharmaceuticals, Inc., Lehi, UT (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/023,360

(22) Filed: Jun. 29, 2018

(65) Prior Publication Data

US 2018/0299432 A1 Oct. 18, 2018

Related U.S. Application Data

(63) Continuation of application No. 15/847,697, filed on Dec. 19, 2017, now Pat. No. 10,132,797.

(60) Provisional application No. 62/436,221, filed on Dec. 19, 2016, provisional application No. 62/562,990, filed on Sep. 25, 2017.

(51) Int. Cl.
| | |
|---|---|
| *C07K 14/00* | (2006.01) |
| *G01N 33/50* | (2006.01) |
| *A61K 31/4545* | (2006.01) |
| *A61K 31/7068* | (2006.01) |
| *A61K 31/136* | (2006.01) |
| *A61K 31/496* | (2006.01) |
| *A61K 31/704* | (2006.01) |
| *A61K 45/06* | (2006.01) |
| *A61P 35/02* | (2006.01) |
| *C12N 7/00* | (2006.01) |
| *A61P 35/00* | (2006.01) |
| *C07K 14/47* | (2006.01) |
| *C12Q 1/6886* | (2018.01) |

(52) U.S. Cl.
CPC ....... *G01N 33/5091* (2013.01); *A61K 31/136* (2013.01); *A61K 31/4545* (2013.01); *A61K 31/496* (2013.01); *A61K 31/704* (2013.01); *A61K 31/7068* (2013.01); *A61K 45/06* (2013.01); *A61P 35/00* (2018.01); *A61P 35/02* (2018.01); *C07K 14/00* (2013.01); *C07K 14/4747* (2013.01); *C12N 7/00* (2013.01); *C12Q 1/6886* (2013.01); *G01N 33/5011* (2013.01); *G01N 33/5079* (2013.01); *C07K 2319/10* (2013.01); *C12N 2740/16322* (2013.01); *G01N 2333/47* (2013.01); *G01N 2800/56* (2013.01)

(58) Field of Classification Search
None
See application file for complete search history.

(56) References Cited

U.S. PATENT DOCUMENTS

| | | | |
|---|---|---|---|
| 4,522,811 A | 6/1985 | Eppstein et al. |
| 4,676,980 A | 6/1987 | Segal et al. |
| 4,816,567 A | 3/1989 | Cabilly et al. |
| 4,900,727 A | 2/1990 | Kattige et al. |
| 4,946,778 A | 8/1990 | Ladner et al. |
| 5,225,539 A | 7/1993 | Winter |
| 5,545,806 A | 8/1996 | Lonberg et al. |
| 5,545,807 A | 8/1996 | Surani et al. |
| 5,569,825 A | 10/1996 | Lonberg et al. |
| 5,633,425 A | 5/1997 | Lonberg et al. |
| 5,804,604 A | 9/1998 | Frankel et al. |
| 5,916,771 A | 6/1999 | Hon et al. |
| 5,939,598 A | 8/1999 | Kucherlapati et al. |
| 5,965,703 A | 10/1999 | Horne et al. |
| 6,087,366 A | 7/2000 | Park et al. |
| 6,136,981 A | 10/2000 | Brion et al. |
| 6,225,473 B1 | 5/2001 | Breipohl et al. |
| 6,258,540 B1 | 7/2001 | Lo et al. |
| 6,406,912 B1 | 6/2002 | Holla |
| 6,576,647 B2 | 6/2003 | Bafus et al. |
| 6,821,990 B2 | 11/2004 | Kesseler |
| 7,064,193 B1 | 6/2006 | Cory et al. |
| 7,714,005 B2 | 5/2010 | Chen et al. |
| 7,829,662 B2 | 11/2010 | Korsmeyer et al. |

(Continued)

FOREIGN PATENT DOCUMENTS

| | | |
|---|---|---|
| CN | 1583776 A | 2/2005 |
| WO | 91/00360 A1 | 1/1991 |

(Continued)

OTHER PUBLICATIONS

Yeh et al (Oncotarget, 2010, 6(5): 2667-2679).*

(Continued)

*Primary Examiner* — Sean E Aeder
(74) *Attorney, Agent, or Firm* — Oblon, McClelland, Maier & Neustadt, L.L.P.

(57) ABSTRACT

The present disclosure is generally directed to profiling peptides, compositions, and kits, as well as methods of use thereof. The profiling peptides comprise an Mcl-1 binding domain, and optionally a cellular uptake moiety. The methods of using such profiling peptides include predicting sensitivity of a cancer, selecting a treatment, treating a cancer, producing a sensitivity profile, and the like.

13 Claims, 6 Drawing Sheets

Specification includes a Sequence Listing.

(56) References Cited

U.S. PATENT DOCUMENTS

| | | | |
|---|---|---|---|
| 7,868,133 | B2 | 1/2011 | Korsemeyer et al. |
| 8,168,755 | B2 | 5/2012 | Cardone et al. |
| 8,221,966 | B2 | 7/2012 | Letai |
| 9,540,674 | B2 | 1/2017 | Letai |
| 9,758,539 | B2 | 9/2017 | Siddiqui-Jain et al. |
| 9,901,574 | B2 | 2/2018 | Warner et al. |
| 2002/0115613 | A1 | 8/2002 | Kumar |
| 2003/0073661 | A1 | 4/2003 | Matsuyama et al. |
| 2005/0153991 | A1 | 7/2005 | Gianella-Borradori et al. |
| 2008/0027105 | A1 | 1/2008 | Suarez et al. |
| 2009/0030005 | A1 | 1/2009 | Kamb et al. |
| 2010/0286057 | A1 | 11/2010 | Walensky et al. |
| 2011/0008371 | A1 | 1/2011 | Michelson |
| 2011/0130309 | A1 | 6/2011 | Cardone |
| 2011/0251240 | A1 | 10/2011 | Suarez et al. |
| 2012/0225851 | A1 | 9/2012 | Cardone et al. |
| 2013/0079424 | A1 | 3/2013 | Gerber et al. |
| 2013/0122492 | A1 | 5/2013 | Khosravi et al. |
| 2014/0080838 | A1 | 3/2014 | Wendel et al. |
| 2014/0303167 | A1 | 10/2014 | Choidas et al. |
| 2015/0051249 | A1 | 2/2015 | Walensky |
| 2015/0150869 | A1 | 6/2015 | Cardone et al. |
| 2015/0301053 | A1 | 10/2015 | Pierceall et al. |
| 2015/0352097 | A1 | 12/2015 | Cardone et al. |
| 2015/0362479 | A1 | 12/2015 | Letai et al. |
| 2016/0303101 | A1 | 10/2016 | Warner et al. |
| 2016/0340376 | A1 | 11/2016 | Siddiqui-Jain et al. |
| 2017/0260268 | A1* | 9/2017 | Beatty .......... C07K 14/705 |
| 2017/0334938 | A1 | 11/2017 | Siddiqui-Jain et al. |
| 2018/0172673 | A1 | 6/2018 | Bearss et al. |

FOREIGN PATENT DOCUMENTS

| | | |
|---|---|---|
| WO | 92/20373 A1 | 11/1992 |
| WO | 93/08829 A1 | 5/1993 |
| WO | 94/02602 A1 | 2/1994 |
| WO | 94/11026 A2 | 5/1994 |
| WO | 96/15263 A1 | 5/1996 |
| WO | 96/27011 A1 | 9/1996 |
| WO | 96/33735 A1 | 10/1996 |
| WO | 96/34096 A1 | 10/1996 |
| WO | 97/05265 A1 | 2/1997 |
| WO | 99/16787 | 4/1999 |
| WO | 99/53049 A1 | 10/1999 |
| WO | 00/59526 A1 | 10/2000 |
| WO | 01/12661 A2 | 2/2001 |
| WO | 02/20568 A2 | 3/2002 |
| WO | 03/028001 A1 | 4/2003 |
| WO | 03/040168 A2 | 5/2003 |
| WO | 2004/022580 A2 | 3/2004 |
| WO | 2004/058804 A1 | 7/2004 |
| WO | 2005/044839 A2 | 5/2005 |
| WO | 2006/099667 A1 | 9/2006 |
| WO | 2006/101846 A1 | 9/2006 |
| WO | 2007/123791 A2 | 11/2007 |
| WO | 2010/093742 A1 | 8/2010 |
| WO | 2010/147961 A1 | 12/2010 |
| WO | 2011/088137 A2 | 7/2011 |
| WO | 2012/122370 A2 | 9/2012 |
| WO | 2013/082660 A1 | 6/2013 |
| WO | 2013/138702 A2 | 9/2013 |
| WO | 2013/170176 A2 | 11/2013 |
| WO | 2013/188355 A1 | 12/2013 |
| WO | 2013/188978 A1 | 12/2013 |
| WO | 2014/047342 A1 | 3/2014 |
| WO | 2014/066848 A1 | 5/2014 |
| WO | 2015/010094 A1 | 1/2015 |
| WO | 2015/017788 A1 | 2/2015 |
| WO | 2015/042249 A1 | 3/2015 |
| WO | 2015/066305 A1 | 5/2015 |
| WO | 2015/070020 A2 | 5/2015 |
| WO | 2016/061144 A1 | 4/2016 |
| WO | 2016/073913 A1 | 5/2016 |
| WO | 2016/115105 A1 | 7/2016 |
| WO | 2016/149613 A1 | 9/2016 |
| WO | 2016/154380 A1 | 9/2016 |
| WO | 2016/176288 A1 | 11/2016 |
| WO | 2016/176299 A1 | 11/2016 |
| WO | 2017/075349 A1 | 5/2017 |

OTHER PUBLICATIONS

Molassiotis et al (Annals of Oncology, 2005, 16: 655-663).*
Yeh et al (Oncotarget, 2015, 6(5): 2667-2679).*
Adams et al., "The Bcl-2 Protein Family: Arbiters of Cell Survival," *Science* 281:1322-1326, 1998.
Adlard et al., "Prediction of the response of colorectal cancer to systemic therapy," *Lancet Oncol.* 3:75-82, 2002.
Aït-Ikhlef et al., "The motoneuron degeneration in the wobbler mouse is independent of the overexpression of a Bcl2 transgene in neurons," *Neuroscience Letters* 199:163-166, 1995.
Almarzooqi et al., "Comparison of Peripheral Blood versus Bone Marrow Blasts Immunophenotype in Pediatric Acute Leukemias," *Ibnosina Journal of Medicine and Biomedical Sciences*, pp. 195-204, 2011. (10 pages).
Altschul et al., "Gapped BLAST and PSI-BLAST: a new generation of protein database search programs," *Nucleic Acids Research* 25(17):3389-3402, 1997.
de Azevedo Jr. et al., "Structural basis for inhibition of cyclin-dependent kinase 9 by flavopiridol," *Biochemical and Biophysical Research Communications* 293:566-571, 2002.
Bae et al., "Underphosphorylated BAD interacts with diverse antiapoptotic Bcl-2 family proteins to regulate apoptosis," *Apoptosis* 6:319-330, 2001.
Barretina et al., "The Cancer Cell Line Encyclopedia enables predictive modelling of anticancer drug sensitivity," *Nature* 483:603-607, 2012; Addendum in: *Nature* 492:290, 2012.
Bearss, "NOXA Priming—Predictive Biomarker for Patients With Acute Myeloid Leukemia to Improve Treatment Outcomes," 2016, retrieved from https://openforum.hbs.org/challenge/precision-medicine/submit-ideas/noxa-priming-predic . . . , 7 pages.
Blachly et al., "Emerging Drug Profile: Cyclin-Dependent Kinase Inhibitors," *Leuk Lymphoma* 54:2133-2143, 2013. (22 pages).
Bodet et al., "BH3-only protein Bik is involved in both apoptosis induction and sensitivity to oxidative stress in multiple myeloma," *British Journal of Cancer* 103:1808-1814, 2010.
Bose et al., "Mcl-1 as a therapeutic target in acute myelogenous leukemia (AML)," *Leukemia Research Reports* 2:12-14, 2013.
Bouillet et al., "Proapoptotic Bcl-2 Relative Bim Required for Certain Apoptotic Responses, Leukocyte Homeostasis, and to Preclude Autoimmunity," *Science* 286:1735-1738, 1999.
Boyd et al., "Bik, a novel death-inducing protein shares a distinct sequence motif with Bcl-2 family proteins and interacts with viral and cellular survival-promoting proteins," *Oncogene* 11:1921-1928, 1995.
Brady et al., "Reflections on a peptide," *Nature* 368:692-693, 1994.
Brennan et al., "Preparation of Bispecific Antibodies by Chemical Recombination of Monoclonal Immunoglobulin $G_1$ Fragments," *Science* 229:81-83, 1985.
Brunelle et al., "MCL-1-dependent leukemia cells are more sensitive to chemotherapy than BCL-2-dependent counterparts," *J. Cell. Biol.* 187(3):429-442, 2009.
Brunetto et al., "First-in-human, Pharmacokinetic and Pharmacodynamic Phase I Study of Resminostat, an Oral Histone Deacetylase Inhibitor, in Patients with Advanced Solid Tumors," *Clin Cancer Res* 19(19):5494-5504, 2013.
Buggy et al., "CRA-024781: a novel synthetic inhibitor of histone deacetylase enzymes with antitumor activity in vitro and in vivo," *Mol Cancer Ther* 5(5): 1309-1317, 2006.
Buron et al., "Use of Human Cancer Cell Lines Mitochondria to Explore the Mechanisms of BH3 Peptides and ABT-737-Induced Mitochondrial Membrane Permeabilization," *PLoS One* 5(3):e9924, 2010. (13 pages).
Byrd et al., "Flavopiridol Induces Apoptosis in Chronic Lymphocytic Leukemia Cells via Activation of Caspase-3 Without Evidence of bcl-2 Modulation or Dependence on Functional p53," *Blood* 92:3804-3816, 1998.

(56) References Cited

OTHER PUBLICATIONS

Byrd et al., "Sequential Phase II Studies of Flavopiridol by 72-Hour Continuous Infusion and 1-Hour Intravenous Bolus for the Treatment of Relapsed B-Cell Chronic Lymphocytic Leukemia: Results from CALGB Study 19805," *Blood* 104:3485, 2004. (2 pages).

Byrd et al., "Flavopiridol Administered as a Pharmacologically-Derived Schedule Demonstrates Marked Clinical Activity in Refractory, Genetically High Risk, Chronic Lymphocytic Leukemia (CLL)," *Blood* 104:341, 2004. (2 pages).

Byrd et al., "Chronic Lymphocytic Leukemia," *Hematology*, pp. 163-183, 2004. (21 pages).

Byrd et al., "Treatment of Relapsed Chronic Lymphocytic Leukemia by 72-Hour Continuous Infusion or 1-Hour Bolus Infusion of Flavopiridol: Results from Cancer and Leukemia Group B Study 19805," *Clin Cancer Res* 11:4176-4181, 2005.

Byrd et al., "Flavopiridol administered using a pharmacologically derived schedule is associated with marked clinical efficacy in refractory, genetically high-risk chronic lymphocytic leukemia," *Blood* 109:399-404, 2007.

Calin et al., "A MicroRNA Signature Associated with Prognosis and Progression in Chronic Lymphocytic Leukemia," *The New England Journal of Medicine* 353:1793-1801, 2005.

Carlson et al., "Flavopiridol Induces $G_1$ Arrest with Inhibition of Cyclin-dependent Kinase (CDK) 2 and CDK4 in Human Breast Carcinoma Cells," *Cancer Research* 56:2973-2978, 1996.

Caron et al., "Engineered Humanized Dimeric Forms of IgG Are More Effective Antibodies," *J. Exp. Med.* 176:1191-1195, 1992.

Cartron et al., "The First α Helix of Bax Plays a Necessary Role in Its Ligand-Induced Activation by the BH3-Only Proteins Bid and PUMA," *Molecular Cell* 16:807-818, 2004.

Certo et al., "Mitochondria primed by death signals determine cellular addiction to antiapoptotic BCL-2 family members," *Cancer Cell* 9:351-365, 2006.

Chao et al., "Flavopiridol Inhibits P-TEFb and Blocks HIV-1 Replication," *The Journal of Biological Chemistry* 275:28345-28348, 2000.

Chao et al., "Flavopiridol Inactivates P-TEFb and Blocks Most RNA Polymerase II Transcription in Vivo," *The Journal of Biological Chemistry* 276:31793-31799, 2001.

Chen et al., "Caspase cleavage of $Bim_{EL}$ triggers a positive feedback amplification of apoptotic signaling," *PNAS* 101(5): 1235-1240, 2004.

Chen et al., "Mcl-1 Down-regulation Potentiates ABT-737 Lethality by Cooperatively Inducing Bak Activation and Bax Translocation," *Cancer Res* 67(2):782-791, 2007.

Chen et al., "Transcription inhibition by flavopiridol: mechanism of chronic lymphocytic leukemia cell death," *Blood* 106:2513-2519, 2005.

Chen et al., "Differential Targeting of Prosurvival Bcl-2 Proteins by Their BH3-Only Ligands Allows Complementary Apoptotic Function," *Molecular Cell* 17:393-403, 2005.

Chen et al., "Mechanism of action of SNS-032, a novel cyclin-dependent kinase inhibitor in chronic lymphocytic leukemia," *Blood* 113:4637-4645, 2009.

Cheng et al., "Bax-independent inhibition of apoptosis by $Bcl-x_L$," *Nature* 379:554-556, 1996.

Cheng et al., "BCL-2, $BCL-X_L$ Sequester BH3 Domain-Only Molecules Preventing BAX- and BAK-Mediated Mitochondrial Apoptosis," *Molecular Cell* 8:705-711, 2001.

Cheson et al., "National Cancer Institute-Sponsored Working Group Guidelines for Chronic Lymphocytic Leukemia: Revised Guidelines for Diagnosis and Treatment," *Blood* 87:4990-4997, 1996.

Chipuk et al., "Direct Activation of Bax by p53 Mediates Mitochondrial Membrane Permeabilization and Apoptosis," *Science* 303:1010-1014, 2004.

Chittenden et al., "A conserved domain in Bak, distinct from BH1 and BH2, mediates cell death and protein binding functions," *The EMBO Journal* 14(22):5589-5596, 1995.

Chittenden et al., "Induction of apoptosis by the Bcl-2 homologue Bak," *Nature* 374:733-736, 1995.

Chonghaile et al., "Mitochondrial Apoptotic Priming Measured by BH3 Profiling Regulates Clinical Response to Chemotherapy in Myeloma and Acute Lymphoblastic Leukemia and Explains Therapeutic Index," *Blood* 118:1442, 2011. (6 pages).

Chonghaile et al., "Pretreatment Mitochondrial Priming Correlates with Clinical Response to Cytotoxic Chemotherapy," *Science* 334:1129-1133, 2011.

Chonghaile et al., "Supporting Online Material for: Pretreatment Mitochondrial Priming Correlates with Clinical Response to Cytotoxic Chemotherapy," *Science* 334:1129-1133, 2011. (36 pages).

Chonghaile et al., "Mimicking the BH3 domain to kill cancer cells," *Oncogene* 27:S149-S157, 2009.

Cole et al., "The EBV-Hybridoma Technique and Its Application to Human Lung Cancer," in Reisfeld et al. (eds.), *Monoclonal Antibodies and Cancer Therapy*, Alan R. Liss, Inc., New York, New York, USA, 1985, pp. 77-96.

Conaway et al., "The Mediator Complex and Transcription Elongation," *Biochim Biophys Acta* 1829:69-75, 2013. (16 pages).

Cory et al., "The BCL2 Family: Regulators of the Cellular Life-Or-Death Switch," *Nature Reviews Cancer* 2:647-656, 2002.

Cosulich et al., "Regulation of apoptosis by BH3 domains in a cell-free system," *Current Biology* 7:913-920, 1997.

Cote et al., "Generation of human monoclonal antibodies reactive with cellular antigens," *Proc. Natl. Acad. Sci. USA* 80:2026-2030, 1983.

Czabotar et al., "Bax activation by Bim?" *Cell Death and Differentiation* 16:1187-1191, 2009.

Czabotar et al., "Structural insights into the degradation of Mcl-1 induced by BH3 domains," *PNAS* 104:6217-6222, 2007.

Czech et al., "Antitumoral activity of flavone L 86-8275," *International Journal of Oncology* 6:31-36, 1995.

Daigle et al., "Potent inhibition of DOT1L as treatment of MLL-fusion leukemia," *Blood* 122(6): 1017-1025, 2013.

Danial et al., "Cell Death: Critical Control Points," *Cell* 116:205-219, 2004.

Davids et al., "BH3 Profiling Demonstrates That Restoration of Apoptotic Priming Contributes to Increased Sensitivity to PI3K Inhibition in Stroma-Exposed Chronic Lymphocytic Leukemia Cells," *Blood* 118:974, 2011. (6 pages).

Davids et al., "Targeting the B-Cell Lymphoma/Leukemia 2 Family in Cancer," *Journal of Clinical Oncology* 30(25):3127-3135, 2012.

Degrado, "Design of Peptides and Proteins," *Advances in Protein Chemistry* 39:51-124, 1988.

Deng et al., "BH3 Profiling Identifies Three Distinct Classes of Apoptotic Blocks to Predict Response to ABT-737 and Conventional Chemotherapeutic Agents," *Cancer Cell* 12:171-185, 2007.

Derenne et al., "Antisense strategy shows that Mcl-1 rather than Bcl-2 or $Bcl-x_L$ is an essential survival protein in human myeloma cells," *Blood* 100:194-199, 2002.

Desagher et al., "Bid-induced Conformational Change of Bax Is Responsible for Mitochondrial Cytochrome c Release during Apoptosis," *The Journal of Cell Biology* 144(5):891-901, 1999.

Denman et al., "Context Dependent Diagnosis Test for Guiding Cancer Treatment," U.S. Appl. No. 62/102,499, filed Jan. 12, 2015, 71 pages.

Denman et al., "Abstract 3400: Mitochondrial profiling in AML patients treated with an Alvocidib containing regimen reveals MCL1 dependency in responder bone marrow," *Cancer Res* 75:3400, 2015. (2 pages).

Di Lisa et al., "Mitochondrial Function and Cell Injury in Single Cardiac Myocytes Exposed to Anoxia and Reoxygenation," *Transplantation Proceedings* 27(5):2829-2830, 1995.

Di Lisa et al., "Mitochondrial membrane potential in single living adult rat cardiac myocytes exposed to anoxia or metabolic inhibition," *Journal of Physiology* 486.1:1-13, 1995.

Diamandis et al. (eds.), *Immunoassay*, Academic Press, San Diego, CA, 1996, 613 pages.

Dinnen et al., "Redirecting Apoptosis to Aponecrosis Induces Selective Cytotoxicity to Pancreatic Cancer Cells through Increased ROS, Decline in ATP Levels, and VDAC," *Mol Cancer Ther* 12(12):2792-2803, 2013.

(56) References Cited

OTHER PUBLICATIONS

Döhner et al., "Genomic Aberrations and Survival in Chronic Lymphocytic Leukemia," *The New England Journal of Medicine* 343:1910-1916, 2000.

Egle et al., "Bim is a suppressor of Myc-induced mouse B cell leukemia," *PNAS* 101(16):6164-6169, 2004.

Ellerby et al., "Anti-cancer activity of targeted pro-apoptotic peptides," *Nature Medicine* 5(9):1032-1038, 1999.

Elliott et al., "Intercellular Trafficking and Protein Delivery by a Herpesvirus Structural Protein," *Cell* 88:223-233, 1997.

Elston et al., "Pathological prognostic factors in breast cancer. I. The value of histological grade in breast cancer: experience from a large study with long-term follow-up," *Histopathology* 19:403-410, 1991.

Ember et al., "Acetyl-lysine Binding Site of Bromodomain-Containing Protein 4 (BRD4) Interacts with Diverse Kinase Inhibitors," *ACS Chem. Biol.* 9:1160-1171, 2014.

Eskes et al., "Bid Induces the Oligomerization and Insertion of Bax into the Outer Mitochondrial Membrane," *Molecular and Cellular Biology* 20(3):929-935, 2000.

Falkenberg et al., "Histone deacetylases and their inhibitors in cancer, neurological diseases and immune disorders," *Nature Reviews Drug Discovery* 13:673-691, 2014.

Fanidi et al., "Cooperative interaction between c-myc and bcl-2 proto-oncogenes," *Nature* 359:554-556, 1992.

Filippakopoulos et al., "Selective inhibition of BET bromodomains," *Nature* 468:1067-1073, 2010.

Filippakopoulos et al., "Targeting bromodomains: epigenetic readers of lysine acetylation," *Nature Reviews Drug Discovery* 13:337-356, 2014.

Fish et al., "Identification of a Chemical Probe for Bromo and Extra C-Terminal Bromodomain Inhibition through Optimization of a Fragment-Derived Hit," *J. Med. Chem.* 55:9831-9837, 2012.

Fiskum et al., "[21] Apoptosis-Related Activities Measured with Isolated Mitochondria and Digitonin-Permeabilized Cells," *Methods in Enzymology* 322:222-234, 2000.

Fiskus et al., "Highly Active Combination of BRD4 Antagonist and Histone Deacetylase Inhibitor against Human Acute Myelogenous Leukemia Cells," *Molecular Cancer Therapeutics* 13:1142-1154, 2014.

Flinn et al., "Flavopiridol administered as a 24-hour continuous infusion in chronic lymphocytic leukemia lacks clinical activity," *Leukemia Research* 29:1253-1257, 2005.

Foight et al., "Designed BH3 Peptides with High Affinity and Specificity for Targeting Mcl-1 in Cells," *ACS Chem. Biol.* 9:1962-1968, 2014.

Frankel et al., "Activity of synthetic peptides from the Tat protein of human immunodeficiency virus type 1," *Proc. Natl. Acad. Sci. USA* 86:7397-7401, 1989.

Friedman et al., "Precision medicine for cancer with next-generation functional diagnostics," *Nat Rev Cancer* 15(12):747-756, 2015. (26 pages).

Fuchs et al., "Pathway for Polyarginine Entry into Mammalian Cells," *Biochemistry* 43(9):2438-2444, 2004. (15 pages).

Fukui et al., "The Analysis of the Effect of JQ1 and Flavopiridol on Chondrocytes under Inflammatory Stimuli," *ORS 2014 Annual Meeting*, New Orleans, Louisiana, USA, Mar. 15-18, 2014, 4 pages.

Futaki et al., "Arginine-rich Peptides: An Abundant Source of Membrane-Permeable Peptides Having Potential as Carriers for Intracellular Protein Delivery," *The Journal of Biological Chemistry* 276(8):5836-5840, 2001.

Geserick et al., "The ratio of Mcl-1 and Noxa determines ABT737 resistance in squamous cell carcinoma of the skin," *Cell Death and Disease* 5:e1412, 2014. (14 pages).

Giles et al., "A Phase I Study of Intravenous LBH589, a Novel Cinnamic Hydroxamic Acid Analogue Histone Deacetylase Inhibitor, in Patients with Refractory Hematologic Malignancies," *Clin Cancer Res* 12(15):4628-4635, 2006.

Gojo et al., "The Cyclin-dependent Kinase Inhibitor Flavopiridol Induces Apoptosis in Multiple Myeloma Cells through Transcriptional Repression and Down-Regulation of Mcl-1," *Clinical Cancer Research* 8:3527-3538, 2002.

Goldsmith et al., "BH3 peptidomimetics potently activate apoptosis and demonstrate single agent efficacy in neuroblastoma," *Oncogene* 25:4525-4533, 2006.

Göttlicher et al., "Valproic acid defines a novel class of HDAC inhibitors inducing differentiation of transformed cells," *The EMBO Journal* 20(24):6969-6978, 2001.

Green, "Life, Death, BH3 Profiles, and the Salmon Mousse," *Cancer Cell* 12:97-99, 2007.

Green et al., "A matter of life and death," *Cancer Cell* 1:19-30, 2002.

Green et al., "The Pathophysiology of Mitochondrial Cell Death," *Science* 305:626-629, 2004.

Griffiths et al., "Cell Damage-induced Conformational Changes of the Pro-Apoptotic Protein Bak In Vivo Precede the Onset of Apoptosis," *The Journal of Cell Biology* 144(5):903-914, 1999.

Gross et al., "Enforced dimerization of BAX results in its translocation, mitochondrial dysfunction and apoptosis," *The EMBO Journal* 17(14):3878-3885, 1998.

Gruber et al., "Efficient Tumor Cell Lysis Mediated by a Bispecific Single Chain Antibody Expressed in *Escherichia coli*," *Journal of Immunology* 152:5368-5374, 1994.

Guha, "Cyclin-dependent kinase inhibitors move into Phase III," *Nature Reviews Drug Discovery* 11:892-894, 2012.

Gul et al., "Apoptotic blocks and chemotherapy resistance: strategies to identify Bcl-2 protein signatures," *Briefings in Functional Genomics and Proteomics* 7(1):27-34, 2008.

Hanahan, "Heritable formation of pancreatic β-cell tumours in transgenic mice expressing recombinant insulin/simian virus 40 oncogenes," *Nature* 315:115-122, 1985.

Hanahan et al., "The Hallmarks of Cancer," *Cell* 100:57-70, 2000.

Hans et al., "β-Carbolines induce apoptosis in cultured cerebellar granule neurons via the mitochondrial pathway," *Neuropharmacology* 48:105-117, 2005.

Harada et al., "Survival factor-induced extracellular signal-regulated kinase phosphorylates BIM, inhibiting its association with BAX and proapoptotic activity," *PNAS* 101(43):15313-15317, 2004.

Hemann et al., "Suppression of tumorigenesis by the p53 target PUMA," *PNAS* 101(25):9333-9338, 2004.

Hemann et al., "Evasion of the p53 tumour surveillance network by tumour-derived MYC mutants," *Nature* 436(7052):807-811, 2005. (13 pages).

Hengartner et al., "C. elegans Cell Survival Gene ced-9 Encodes a Functional Homolog of the Mammalian Proto-Oncogene bcl-2," *Cell* 76:665-676, 1994.

Hirst et al., "Application of Non-Parametric Regression to Quantitative Structure-Activity Relationships," *Bioorganic & Medicinal Chemistry* 10:1037-1041, 2002.

Hnisz et al., "Super-Enhancers in the Control of Cell Identity and Disease," *Cell* 155:934-947, 2013.

Holinger et al., "Bak BH3 Peptides Antagonize Bcl-$x_L$ Function and Induce Apoptosis through Cytochrome c-independent Activation of Caspases," *The Journal of Biological Chemistry* 274(19):13298-13304, 1999.

Holliger et al., ""Diabodies": Small bivalent and bispecific antibody fragments," *Proc. Natl. Acad. Sci. USA* 90:6444-6448, 1993.

Hoogenboom et al., "By-passing Immunisation—Human Antibodies from Synthetic Repertoires of Germline $V_H$ Gene Segments Rearranged in Vitro," *J. Mol. Biol.* 227:381-388, 1992.

Hopp et al., "Prediction of protein antigenic determinants from amino acid sequences," *Proc. Natl. Acad. Sci. USA* 78(6):3824-3828, 1981.

Hoppel et al., "The Action of Digitonin on Rat Liver Mitochondria," *Biochem J.* 107:367-375, 1968.

Hsu et al., "Nonionic Detergents Induce Dimerization among Members of the Bcl-2 Family," *The Journal of Biological Chemistry* 272(21):13829-13834, 1997.

Huang et al., "BH3-Only Proteins—Essential Initiators of Apoptotic Cell Death," *Cell* 103:839-842, 2000.

(56) References Cited

OTHER PUBLICATIONS

Huse et al., "Generation of a Large Combinatorial Library of the Immunoglobulin Repertoire in Phage Lambda," *Science* 246:1275-1281, 1989.
Innocenti et al., "Flavopiridol Metabolism in Cancer Patients Is Associated with the Occurrence of Diarrhea," *Clinical Cancer Research* 6:3400-3405, 2000.
Inohara et al., "harakiri, a novel regulator of cell death, encodes a protein that activates apoptosis and interacts selectively with survival-promoting proteins Bcl-2 and Bcl-$X_L$," *The EMBO Journal* 16(7):1686-1694, 1997.
Ishizawa et al., "Mitochondrial Profiling of Acute Myeloid Leukemia in the Assessment of Response to Apoptosis Modulating Drugs," *PLoS One* 10(9):e0138377, 2015. (16 pages).
Jackson et al., "Heat shock induces the release of fibroblast growth factor 1 from NIH 3T3 cells," *Proc. Natl. Acad. Sci. USA* 89:10691-10695, 1992.
Jameson et al., "A rationally designed CD4 analogue inhibits experimental allergic encephalomyelitis," *Nature* 368:744-746, 1994.
Jones et al., "Replacing the complementarity-determining regions in a human antibody with those from a mouse," *Nature* 321:522-525, 1986.
Jonkers et al., "Oncogene addiction: Sometimes a temporary slavery," *Cancer Cell* 6:535-538, 2004.
Keating et al., "Results of First Salvage Therapy for Patients Refractory to a Fludarabine Regimen in Chronic Lymphocytic Leukemia," *Leukemia and Lymphoma* 43(9):1755-1762, 2002.
Keating et al., "Therapeutic role of alemtuzumab (Campath-1H) in patients who have failed fludarabine: results of a large international study," *Blood* 99:3554-3561, 2002.
Kelekar et al., "Bcl-2-family proteins: the role of the BH3 domain in apoptosis," *Trends in Cell Biology* 8:324-330, 1998.
Kelekar et al., "Bad Is a BH3 Domain-Containing Protein That Forms an Inactivating Dimer with Bcl-$x_L$," *Molecular and Cellular Biology* 17(12):7040-7046, 1997.
KG-1, ATCC® CCL-246™, ATCC Product Sheet, May 31, 2013, 3 pages.
Kitada et al., "Protein kinase inhibitors flavopiridol and 7-hydroxystaurosporine down-regulate antiapoptosis proteins in B-cell chronic lymphocytic leukemia," *Blood* 96:393-397, 2000.
Köhler et al., "Continuous cultures of fused cells secreting antibody of predefined specificity," *Nature* 256:495-497, 1975.
König et al., "The Novel Cyclin-Dependent Kinase Inhibitor Flavopiridol Downregulates Bcl-2 and Induces Growth Arrest and Apoptosis in Chronic B-Cell Leukemia Lines," *Blood* 90:4307-4312, 1997.
Korsmeyer et al., "Pro-apoptotic cascade activates BID, which oligomerizes BAK or BAX into pores that result in the release of cytochrome c," *Cell Death and Differentiation* 7:1166-1173, 2000.
Kozbor et al., "The production of monoclonal antibodies from human lymphocytes," *Immunology Today* 4(3):72-79, 1983.
Kryštof et al., "Cyclin-Dependent Kinase Inhibitors as Anticancer Drugs," *Current Drug Targets* 11:291-302, 2010.
Kuwana et al., "Bid, Bax, and Lipids Cooperate to Form Supramolecular Openings in the Outer Mitochondrial Membrane," *Cell* 111:331-342, 2002.
Kuwana et al., "BH3 Domains of BH3-Only Proteins Differentially Regulate Bax-Mediated Mitochondrial Membrane Permeabilization Both Directly and Indirectly," *Molecular Cell* 17:525-535, 2005.
Kyte et al., "A Simple Method for Displaying the Hydropathic Character of a Protein," *J. Mol. Biol.* 157:105-132, 1982.
La Vieira et al., "Cell permeable BH3-peptides overcome the cytoprotective effect of Bcl-2 and Bcl-$X_L$," *Oncogene* 21:1963-1977, 2002.
Labi et al., "Targeting the Bcl-2-regulated apoptosis pathway by BH3 mimetics: a breakthrough in anticancer therapy?," *Cell Death and Differentiation* 15:977-987, 2008.
Leo et al., "Characterization of the Antiapoptotic Bcl-2 Family Member Myeloid Cell Leukemia-1 (Mcl-1) and the Stimulation of Its Message by Gonadotropins in the Rat Ovary," *Endocrinology* 140(12):5469-5477, 1999.
Letai, "The BCL-2 network: Mechanistic insights and therapeutic potential," *Drug Discovery Today: Disease Mechanisms* 2(2):145-151, 2005.
Letai et al., "Antiapoptotic BCL-2 is required for maintenance of a model leukemia," *Cancer Cell* 6:241-249, 2004.
Letai, "Perturbing cancer cell mitochondria to learn how to kill cancer with BH3 profiling," Dana-Farber Cancer Institute, Broad Institute, *Cell Circuits and Epigenomics*, Jul. 28, 2014, 47 pages.
Letai, "BH3 domains as BCL-2 inhibitors: prototype cancer therapeutics," *Expert Opin. Biol. Ther.* 3:293-304, 2003.
Letai et al., "Distinct BH3 domains either sensitize or activate mitochondrial apoptosis, serving as prototype cancer therapeutics," *Cancer Cell* 2:183-192, 2002.
Li et al., "tsg101: A Novel Tumor Susceptibility Gene Isolated by Controlled Homozygous Functional Knockout of Allelic Loci in Mammalian Cells," *Cell* 85:319-329, 1996.
Li et al., "Cleavage of BID by Caspase 8 Mediates the Mitochondrial Damage in the Fas Pathway of Apoptosis," *Cell* 94:491-501, 1998.
Li et al., "Endonuclease G is an apoptotic DNase when released from mitochondria," *Nature* 412:95-99, 2001.
Lin et al., "Seventy-Two Hour Continuous Infusion Flavopiridol in Relapsed and Refractory Mantle Cell Lymphoma," *Leukemia & Lymphoma* 43:793-797, 2002.
Lin et al., "Flavopiridol given as a 30-min intravenous (IV) bolus followed by 4-hr continuous IV infusion (CIVI) results in clinical activity and tumor lysis in refractory chronic lymphocytic leukemia (CLL)," *Journal of Clinical Oncology, 2004 ASCO Annual Meeting Proceedings (Post-Meeting Edition)* 22(145):8564, 2004. (1 page).
Liu et al., "Bax conformational change is a crucial step for PUMA-mediated apoptosis in human leukemia," *Biochemical and Biophysical Research Communications* 310:956-962, 2003.
Liu et al., "BH3-based Fusion Artificial Peptide Induces Apoptosis and Targets Human Colon Cancer," *Molecular Therapy* 17:1509-1516, 2009.
Liu et al., "CDKI-71, a novel CDK9 inhibitor, is preferentially cytotoxic to cancer cells compared to flavopiridol," *Int. J. Cancer* 130:1216-1226, 2012.
Lonberg et al., "Antigen-specific human antibodies from mice comprising four distinct genetic modifications," *Nature* 368:856-859, 1994.
Long et al., "Optimization and validation of mitochondria-based functional assay as a useful tool to identify BH3-like molecules selectively targeting anti-apoptotic Bcl-2 proteins," *BMC Biotechnology* 13:45, 2013. (10 pages).
Lovén et al., "Selective Inhibition of Tumor Oncogenes by Disruption of Super-Enhancers," *Cell* 153:320-334, 2013. (27 pages).
Lozanski et al., "Alemtuzumab is an effective therapy for chronic lymphocytic leukemia with p53 mutations and deletions," *Blood* 103:3278-3281, 2004.
Luo et al., "Bid, a Bcl2 Interacting Protein, Mediates Cytochrome c Release from Mitochondria in Response to Activation of Cell Surface Death Receptors," *Cell* 94:481-490, 1998.
Lutter et al., "The pro-apoptotic Bcl-2 family member tBid localizes to mitochondrial contact sites," *BMC Cell Biology* 2:22, 2001. (9 pages).
Marani et al., "Identification of Novel Isoforms of the BH3 Domain Protein Bim Which Directly Activate Bax to Trigger Apoptosis," *Molecular and Cellular Biology* 22(11):3577-3589, 2002.
Marks et al., "By-passing Immunization: Human Antibodies from V-gene Libraries Displayed on Phage," *J. Mol. Biol.* 222:581-597, 1991.
Marks et al., "By-Passing Immunization: Building High Affinity Human Antibodies by Chain Shuffling," *Nature Bio/Technology* 10:779-783, 1992.
Martin, "Opening the Cellular Poison Cabinet," *Science* 330:1330-1331, 2010.
Mason et al., "The Hypogonadal Mouse: Reproductive Functions Restored by Gene Therapy," *Science* 234:1372-1378, 1986.
Matsushita et al., "A High-Efficiency Protein Transduction System Demonstrating the Role of PKA in Long-Lasting Long-Term Potentiation," *The Journal of Neuroscience* 21(16):6000-6007, 2001.
Matsuzaki, "Why and how are peptide-lipid interactions utilized for self defence?," *Biochem. Soc. Transactions* 29:598-601, 2001.

(56) References Cited

OTHER PUBLICATIONS

McDonnell et al., "bcl-2-Immunoglobulin Transgenic Mice Demonstrate Extended B Cell Survival and Follicular Lymphoproliferation," *Cell* 57:79-88, 1989.
Means et al., *Chemical Modification of Proteins*, Holden-Day, Inc., San Francisco, California, USA, 1974, "Modifications to change properties," Chapter 3, pp. 35-54. (22 pages).
Miller et al., "Therapeutic Strategies to Enhance the Anticancer Efficacy of Histone Deacetylase Inhibitors," *Journal of Biomedicine and Biotechnology* 2011:514261, 2011. (17 pages).
Milstein et al., "Hybrid hybridomas and their use in immunohistochemistry," *Nature* 305:537-540, 1983.
Montero et al., "Drug-Induced Death Signaling Strategy Rapidly Predicts Cancer Response to Chemotherapy," *Cell* 160:977-989, 2015. (14 pages).
Moore et al., "Chronic lymphocytic leukemia requires BCL2 to sequester prodeath BIM, explaining sensitivity to BCL2 antagonist ABT-737," *The Journal of Clinical Investigation* 117(1):112-121, 2007.
Moore et al., "BH3 profiling—measuring integrated function of the mitochondrial apoptotic pathway to predict cell fate decisions," *Cancer Lett* 332:202-205, 2013. (10 pages).
Morrison, "Success in specification," *Nature* 368:812-813, 1994.
Muchmore et al., "X-ray and NMR structure of human Bcl-$x_L$, an inhibitor of programmed cell death," *Nature* 381:335-341, 1996. (16 pages).
Munson et al., "LIGAND: A Versatile Computerized Approach for Characterization of Ligand-Binding Systems," *Analytical Biochemistry* 107:220-239, 1980. (22 pages).
Murthi et al., "Structure-Activity Relationship Studies of Flavopiridol Analogues," *Bioorganic & Medicinal Chemistry Letters* 10:1037-1041, 2000.
Naik et al., "An Antiinflammatory Cum Immunomodulatory Piperidinylbenzopyranone From *Dysoxylum binectariferum*: Isolation, Structure and Total Synthesis," *Tetrahedron* 44:2081-2086, 1988.
Nakano et al., "PUMA, a Novel Proapoptotic Gene, Is Induced by p53," *Molecular Cell* 7:683-694, 2001.
Narita et al., "Bax interacts with the permeability transition pore to induce permeability transition and cytochrome c release in isolated mitochondria," *Proc. Natl. Acad. Sci. USA* 95:14681-14686, 1998.
Neuberger, "Generating high-avidity human Mabs in mice," *Nature Biotechnology* 14:826, 1996.
Noel et al., "Abstract C244: Development of the BET bromodomain inhibitor OTX015," *Proceedings of the AACR-NCI-EORTC International Conference: Molecular Targets and Cancer Therapeutics*, Oct. 19-23, 2013, Boston, MA, Philadelphia, PA: AACR; *Mol Cancer Ther* 12(11 Suppl): Abstract No. C244, 2013. (4 pages).
O'Brien et al., "Phase I to II Multicenter Study of Oblimersen Sodium, a Bcl-2 Antisense Oligonucleotide, in Patients With Advanced Chronic Lymphocytic Leukemia," *Journal of Clinical Oncology* 23(30):7697-7702, 2005.
O'Connor et al., "Bim: a novel member of the Bcl-2 family that promotes apoptosis," *The EMBO Journal* 17(2):384-395, 1998.
Oda et al., "Noxa, a BH3-Only Member of the Bcl-2 Family and Candidate Mediator of p53-Induced Apoptosis," *Science* 288:1053-1058, 2000.
Oh et al., "Conformational Changes in BID, a Pro-apoptotic BCL-2 Family Member, upon Membrane Binding," *The Journal of Biological Chemistry* 280(1):753-767, 2005.
Oltersdorf et al., "An inhibitor of Bcl-2 family proteins induces regression of solid tumours," *Nature* 435:677-681, 2005.
Opferman et al., "Development and maintenance of B and T lymphocytes requires antiapoptotic MCL-1," *Nature* 426:671-676, 2003.
Oscier et al., "Multivariate analysis of prognostic factors in CLL: clinical stage, IGVH gene mutational status, and loss or mutation of the p53 gene are independent prognostic factors," *Blood* 100:1177-1184, 2002.

Paoluzzi et al., "The BH3-only mimetic ABT-737 synergizes the antineoplastic activity of proteasome inhibitors in lymphoid malignancies," *Blood* 112:2906-2916, 2008.
Paquin et al., "Design and synthesis of 4-[(s-triazin-2-ylamino)methyl]-N-(2-aminophenyl)-benzamides and their analogues as a novel class of histone deacetylase inhibitors," *Bioorganic & Medicinal Chemistry Letters* 18:1067-1071, 2008.
Parker et al., "Early Induction of Apoptosis in Hematopoietic Cell Lines After Exposure to Flavopiridol," *Blood* 91:458-465, 1998.
Parry et al., "Dinaciclib (SCH 727965), a Novel and Potent Cyclin-Dependent Kinase Inhibitor," *Mol Cancer Ther* 9(8):2344-2353, 2010.
Paruch et al., "Discovery of Dinaciclib (SCH 727965): A Potent and Selective Inhibitor of Cyclin-Dependent Kinases," *ACS Med. Chem. Lett* 1:204-208, 2010.
Perkins et al., "Frequency and Type of Serious Infections in Fludarabine-Refractory B-Cell Chronic Lymphocytic Leukemia and Small Lymphocytic Lymphoma," *Cancer* 94:2033-2039, 2002.
Picaud et al., "PFI-1, a Highly Selective Protein Interaction Inhibitor, Targeting BET Bromodomains," *Cancer Res* 73(11):3336-3346, 2013.
Piekarz et al., "Inhibitor of histone deacetylation, depsipeptide (FR901228), in the treatment of peripheral and cutaneous T-cell lymphoma: a case report," *Blood* 98:2865-2868, 2001.
Pierceall et al., "BH3 Profiling Discriminates Response to Cytarabine-Based Treatment of Acute Myelogenous Leukemia," *Molecular Cancer Therapeutics* 12(12):2940-2949, 2013.
Pierceall et al., "Mcl-1 Dependence Predicts Response to Vorinostat and Gemtuzumab Ozogamicin in Acute Myeloid Leukemia," *Leuk Res* 38:564-568, 2014. (13 pages).
Pierceall et al., "Mitochondrial Priming of Chronic Lymphocytic Leukemia Patients Associates Bcl-$x_L$ Dependence with Alvocidib Response," *Leukemia* 28:2251-2254, 2014. (7 pages).
Pinkert et al., "An albumin enhancer located 10 kb upstream functions along with its promoter to direct efficient, liver-specific expression in transgenic mice," *Genes & Development* 1:268-276, 1987.
Plumb et al., "Pharmacodynamic Response and Inhibition of Growth of Human Tumor Xenografts by the Novel Histone Deacetylase Inhibitor PXD101," *Molecular Cancer Therapeutics* 2:721-728, 2003.
Pode-Shakked et al., "Development tumourigenesis: NCAM as a putative marker for the malignant renal stem/progenitor cell population," *J. Cell. Mol. Med.* 13(8B):1792-1808, 2009.
Polster et al., "BH3 Death Domain Peptide Induces Cell Type-selective Mitochondrial Outer Membrane Permeability," *The Journal of Biological Chemistry* 276:37887-37894, 2001.
Presta, "Antibody engineering," *Current Opinion in Structural Biology* 2:593-596, 1992.
Pritzker, "Cancer Biomarkers: Easier Said Than Done," *Clinical Chemistry* 48(8):1147-1150, 2002.
Putcha et al., "Induction of BIM, a Proapoptotic BH3-Only BCL-2 Family Member, Is Critical for Neuronal Apoptosis," *Neuron* 29:615-628, 2001.
Puthalakath et al., "The Proapoptotic Activity of the Bcl-2 Family Member Bim is Regulated by Interaction with the Dynein Motor Complex," *Molecular Cell* 3:287-296, 1999.
Puthalakath et al., "Bmf: A Proapoptotic BH3-Only Protein Regulated by Interaction with the Myosin V Actin Motor Complex, Activated by Anoikis," *Science* 293:1829-1832, 2001.
Puthalakath et al., "Keeping killers on a tight leash: transcriptional and post-translational control of the pro-apoptotic activity of BH3-only proteins," *Cell Death and Differentiation* 9:505-512, 2002.
Quinsay et al., "Abstract 1783: Pro-Apoptotic Bnip3 Mediates Permeabilization of Mitochondria and Release of Cytochrome c via a Novel Mechanism," *Circulation* 118:S388. 2008. (5 pages).
Raff, "Social controls on cell survival and cell death," *Nature* 356:397-400, 1992.
Rassenti et al., "ZAP-70 Compared with Immunoglobulin Heavy-Chain Gene Mutation Status as a Predictor of Disease Progression in Chronic Lymphocytic Leukemia," *N. Engl. J. Med.* 351:893-901, 2004.

(56) References Cited

OTHER PUBLICATIONS

Ray et al., "BNIP3 Heterodimerizes with Bcl-2/Bcl-$X_L$ and Induces Cell Death Independent of a Bcl-2 Homology 3 (BH3) Domain at Both Mitochondrial and Nonmitochondrial Sites," *The Journal of Biological Chemistry* 275(2):1439-1448, 2000.
Raychaudhuri, "Low probability Bid-Bax reaction generates heterogeneity in apoptosis resistance of cancer and cancer stem cells," arXiv:1108.2091 [q-bio.MN], 2011, 17 pages.
Ren et al., "BID, BIM, and PUMA Are Essential for Activation of the BAX- and BAK-Dependent Cell Death Program," *Science* 330:1390-1393, 2010.
Rezaei et al., "Leukemia markers expression of peripheral blood vs. bone marrow blasts using flow cytometry," *Med Sci. Monit* 9:CR359-CR362, 2003.
Richon et al., "A class of hybrid polar inducers of transformed cell differentiation inhibits histone deacetylases," *Proc. Natl. Acad. Sci. USA* 95:3003-3007, 1998.
Riechmann et al., "Reshaping human antibodies for therapy," *Nature* 332:323-327, 1988.
Rollins-Raval et al., "The value of immunohistochemistry for CD14, CD123, CD33, myeloperoxidase and CD68R in the diagnosis of acute and chronic myelomonocytic leukaemias," *Histopathology* 60:933-942, 2012.
Rothbard et al., "Conjugation of arginine oligomers to cyclosporin A facilitates topical delivery and inhibition of inflammation," *Nature Medicine* 6(11):1253-1257, 2000.
Rudek et al., "Clinical Pharmacology of Flavopiridol Following a 72-Hour Continuous Infusion," *Ann Pharmacother* 37:1369-1374, 2003.
Ryan et al., "Heightened mitochondrial priming is the basis for apoptotic hypersensitivity of $CD4^+CD8^+$ thymocytes," *PNAS* 107(29):12895-12900, 2010.
Ryan et al., "BH3 Profiling in Whole Cells by Fluorimeter or FACS," *Methods* 61:156-164, 2013. (22 pages).
Saito et al., "A synthetic inhibitor of histone deacetylase, MS-27-275, with marked in vivo antitumor activity against human tumors," *Proc. Natl. Acad. Sci. USA* 96:4592-4597, 1999.
Samson et al., "A 35 Amino Acid Fragment of Leptin Inhibits Feeding in the Rat," *Endocrinology* 137(11):5182-5185, 1996.
Sattler et al., "Structure of Bcl-$x_L$-Bak Peptide Complex: Recognition Between Regulators of Apoptosis," *Science* 275:983-986, 1997.
Sausville et al., "Inhibition of CDKs as a Therapeutic Modality," *Ann. NY Acad. of Sci.* 910:207-222, 2000.
Schimmer et al., "The BH3 domain of BAD fused to the Antennapedia peptide induces apoptosis via its alpha helical structure and independent of Bcl-2," *Cell Death and Differentiation* 8:725-733, 2001.
Schwartz et al., "Phase II Study of the Cyclin-Dependent Kinase Inhibitor Flavopiridol Administered to Patients With Advanced Gastric Carcinoma," *J Clin Oncol* 19:1985-1992, 2001.
Seal et al., "Identification of a novel series of BET family bromodomain inhibitors: Binding mode and profile of I-BET151 (GSK1210151A)," *Bioorganic & Medicinal Chemistry Letters* 22:2968-2972, 2012.
Sedlacek et al., "Flavopiridol (L86 8275; NSC 649890), a new kinase inhibitor for tumor therapy," *International Journal of Oncology* 9:1143-1168, 1996.
Sen et al., "Artemisinin triggers induction of cell-cycle arrest and apoptosis in *Leishmania donovani* promastigotes," *Journal of Medical Microbiology* 56:1213-1218, 2007.
Senderowicz, "Flavopiridol: the first cyclin-dependent kinase inhibitor in human clinical trials," *Investigational New Drugs* 17:313-320, 1999.
Senderowicz et al., "Phase I Trial of Continuous Infusion Flavopiridol, a Novel Cyclin-Dependent Kinase Inhibitor, in Patients With Refractory Neoplasms," *J. Clin Oncol* 16:2986-2999, 1998.
Senderowicz et al., "Preclinical and Clinical Development of Cyclin-Dependent Kinase Modulators," *J Natl Cancer Inst* 92:376-387, 2000.
Shalaby et al., "Development of Humanized Bispecific Antibodies Reactive with Cytotoxic Lymphocytes and Tumor Cells Overexpressing the HER2 Protooncogene," *J. Exp. Med.* 175:217-225, 1992.
Shangary et al., "Peptides Derived from BH3 Domains of Bcl-2 Family Members: A Comparative Analysis of Inhibition of Bcl-2, Bcl-$x_L$ and Bax Oligomerization, Induction of Cytochrome c Release, and Activation of Cell Death," *Biochemistry* 41:9485-9495, 2002.
Shapiro et al., "A Phase II Trial of the Cyclin-dependent Kinase Inhibitor Flavopiridol in Patients with Previously Untreated Stage IV Non-Small Cell Lung Cancer," *Clinical Cancer Research* 7:1590-1599, 2001.
Shibue et al., "Differential contribution of Puma and Noxa in dual regulation of p53-mediated apoptotic pathways," *The EMBO Journal* 25:4952-4962, 2006.
Shimizu et al., "Proapoptotic BH3-only Bcl-2 family members induce cytochrome c release, but not mitochondrial membrane potential loss, and do not directly modulate voltage-dependent anion channel activity," *PNAS* 97:577-582, 2000.
Shopes, "A Genetically Engineered Human IgG Mutant With Enhanced Cytolytic Activity," *The Journal of Immunology* 148(9):2918-2922, 1992.
Sinicrope et al., "Proapoptotic Bad and Bid Protein Expression Predict Survival in Stages II and III Colon Cancers," *Clin Cancer Res* 14(13):4128-4133, 2008.
Sinicrope et al., "Prognostic Impact of Bim, Puma, and Noxa Expression in Human Colon Carcinomas," *Clin Cancer Res* 14(18):5810-5818, 2008.
Smith et al "Enhancer biology and enhanceropathies," *Nature Structural & Molecular Biology* 21:210-219, 2014.
Smith et al., "An alvocidib-containing regimen is highly effective in AML patients through a mechanism dependent on MCL1 expression and function," *2015 ASCO Annual Meeting*, Abstract No. 7062, 2015. (3 pages).
Soltow et al., "Overexpression of CuZnSOD or MnSOD protects satellite cells from doxorubicin-induced apoptosis," *The FASEB Journal* 21(5): Abstract No. A449, 2007. (2 pages).
Song et al., "Carbon Monoxide Promotes Fas/CD95-induced Apoptosis in Jurkat Cells," *The Journal of Biological Chemistry* 279(43):44327-44334, 2004. (11 pages).
Song et al., "Carbon Monoxide Promotes Fas/CD95-induced Apoptosis in Jurkat Cells," *The Journal of Biological Chemistry* 279(43):44327-44334, 2004—"Additions and Correction," *The Journal of Biological Chemistry* 280(23):22555-22556, 2005. (3 pages).
Stevenson et al., "A chimeric antibody with dual Fc regions (bisFabFc) prepared by manipulations at the IgG hinge," *Anti-Cancer Drug Design* 3:219-230, 1989.
Stewart et al., "The MCL-1 BH3 Helix is an Exclusive MCL-1 inhibitor and Apoptosis Sensitizer," *Nat. Chem. Biol.* 6(8):595-601, 2010. (17 pages).
Sturm et al., "Mutation of p53 and consecutive selective drug resistance in B-CLL occurs as a consequence of prior DNA-damaging chemotherapy," *Cell Death and Differentiation* 10:477-484, 2003.
Sugiyama et al., "Activation of mitochondrial voltage-dependent anion channel by a pro-apoptotic BH3-only protein Bim," *Oncogene* 21:4944-4956, 2002.
Suzuki et al., "Possible Existence of Common Internalization Mechanisms among Arginine-rich Peptides," *The Journal of Biological Chemistry* 277(4):2437-2443, 2002.
Tahir et al., "Potential mechanisms of resistance to venetoclax and strategies to circumvent it," *BMC Cancer* 17:399, 2017. (10 pages).
Tan et al., "Phase I Clinical and Pharmacokinetic Study of Flavopiridol Administered as a Daily 1-Hour Infusion in Patients With Advanced Neoplasms," *J Clin Oncol* 20:4074-4082, 2002.
Taussig et al., "Anti-CD38 antibody-mediated clearance of human repopulating cells masks the heterogeneity of leukemia-initiating cells," *Blood* 112:568-575, 2008.
Terradillos et al., "Direct addition of BimL to mitochondria does not lead to cytochrome c release," *FEBS Letters* 522:29-34, 2002.
Theisen et al., "Reversible inhibition of lysine specific demethylase 1 is a novel anti-tumor strategy for poorly differentiated endometrial carcinoma," *BMC Cancer* 14:752, 2014. (12 pages).

(56) References Cited

OTHER PUBLICATIONS

Thomas et al., "Phase I clinical pharmacokinetic trial of the cyclin-dependent kinase inhibitor flavopiridol," *Cancer Chemother Pharmacol* 50:465-472, 2002.
Thomenius et al., "Using BH3 Profiling as a Predictive Indicator for Myeloma Patient Response to Bortezomib," *Blood* 118:3952, 2011. (6 pages).
Thornton et al., "High dose methyl prednisolone can induce remissions in CLL patients with p53 abnormalities," *Ann Hematol* 82:759-765, 2003.
Thornton et al., "Characterisation of TP53 abnormalities in chronic lymphocytic leukaemia," *The Hematology Journal* 5:47-54, 2004.
Tolero Pharmaceuticals, "Jefferies 2016 Heathcare Conference," 2016, 31 pages.
Toogood et al., "Discovery of a Potent and Selective Inhibitor of Cyclin-Dependent Kinase 4/6," *J. Med. Chem.* 48:2388-2406, 2005.
Touzeau et al., "BH3-profiling identifies heterogeneous dependency of Bcl-2 family members in Multiple Myeloma and predicts sensitivity to BH3 mimetics," *Leukemia* 30(3):761-764, 2016. (8 pages).
Traunecker et al., "Bispecific single chain molecular (Janusins) target cytotoxic lymphocytes on HIV infected cells," *The EMBO Journal* 10(12):3655-3659, 1991.
Tutt et al., "Trispecific F(ab')$_3$ Derivatives That Use Cooperative Signaling Via the TCR/CD3 Complex and CD2 to Activate and Redirect Resting Cytotoxic T Cells," *The Journal of Immunology* 147(1):60-69, 1991.
Valencia et al., "A new reliable fluorescence in situ hybridization method for identifying multiple specific cytogenetic abnormalities in acute myeloid leukemia," *Leukemia & Lymphoma* 51(4):680-685, 2010.
Vaquero et al., "Extracellular Matrix Proteins Protect Pancreatic Cancer Cells From Death via Mitochondrial and Nonmitochondrial Pathways," *Gastroenterology* 125:1188-1202, 2003.
Vaux et al., "Bcl-2 gene promotes haemopoietic cell survival and cooperates with c-myc to immortalize pre-B cells," *Nature* 335:440-442, 1988.
Venkat, "Flavopiridol: A Drug that May Save Lives," 2004, retrieved from https://web.archive.org/web/20060615112217/http://clltopics.org/Chemo/flavopiridol.htm, 7 pages.
Venugopal et al., "A Phase I Study of Quisinostat (JNJ-26481585), an Oral Hydroxamate Histone Deacetylase Inhibitor with Evidence of Target Modulation and Antitumor Activity, in Patients with Advanced Solid Tumors," *Clin Cancer Res* 19(15):4262-4272, 2013.
Verhoeyen et al., "Reshaping Human Antibodies: Grafting an Antilysozyme Activity," *Science* 239:1534-1536, 1988.
Ververis et al., "Histone deacetylase inhibitors (HDACIs): multitargeted anticancer agents," *Biologics: Targets and Therapy* 7:47-60, 2013.
Vitetta et al., "Redesigning Nature's Poisons to Create Anti-Tumor Reagents," *Science* 238:1098-1104, 1987.
Vivès et al., "A Truncated HIV-1 Tat Protein Basic Domain Rapidly Translocates through the Plasma Membrane and Accumulates in the Cell Nucleus," *The Journal of Biological Chemistry* 272(25):16010-16017, 1997.
Vo, "Mitochondrial Priming Determines Chemotherapeutic Response in Acute Myeloid Leukemia," Dissertation, The Division of Medical Sciences, Harvard University, Cambridge, Massachusetts, Apr. 2012, 119 pages.
Vo et al., "Relative Mitochondrial Priming of Myeloblasts and Normal HSCs Determines Chemotherapeutic Success in AML," *Cell* 151:344-355, 2012.
Wang, "The expanding role of mitochondria in apoptosis," *Genes & Development* 15:2922-2933, 2001.
Wang et al., "BID: a novel BH3 domain-only death agonist," *Genes & Development* 10:2859-2869, 1996.
Wang et al., "Cell Permeable Bcl-2 Binding Peptides: A Chemical Approach to Apoptosis Induction in Tumor Cells," *Cancer Research* 60:1498-1502, 2000.
Wang et al., "Structure-based discovery of an organic compound that binds Bcl-2 protein and induces apoptosis of tumor cells," *PNAS* 97(13):7124-7129, 2000.
Wei et al., "tBID, a membrane-targeted death ligand, oligomerizes BAK to release cytochrome c," *Genes & Development* 14:2060-2071, 2000.
Wei et al., "Proapoptotic BAX and BAK: A Requisite Gateway to Mitochondrial Dysfunction and Death," *Science* 292:727-730, 2001.
Weinstein, "Addiction to Oncogenes—the Achilles Heal of Cancer," *Science* 297:63-64, 2002.
Weniger et al., "Treatment-Induced Oxidative Stress and Cellular Antioxidant Capacity Determine Response to Bortezomib in Mantle Cell Lymphoma," *Clinical Cancer Research* 17(15):5101-5112, 2011.
Werner et al., "Bcl-2 Family Member Bfl-1/A1 Sequesters Truncated Bid to Inhibit Its Collaboration with Pro-apoptotic Bak or Bax," *The Journal of Biological Chemistry* 277(25):22781-22788, 2002.
Westerhoff et al., "Magainins and the disruption of membrane-linked free-energy transduction," *Proc. Natl. Acad. Sci. USA* 86:6597-6601, 1989.
Wilkinson, "Ultimate Abs—Immunochemical techniques inspire development of new antibody purification methods," *The Scientist* 14(8):25-28, 2000. (6 pages).
Willis et al., "Proapoptotic Bak is sequestered by Mcl-1 and Bcl-x$_L$, but not Bcl-2, until displaced by BH3-only proteins," *Genes & Development* 19:1294-1305, 2005.
Willis et al., "Apoptosis Initiated When BH3 Ligands Engage Multiple Bcl-2 Homologs, Not Bax or Bak," *Science* 315:856-859, 2007.
Wolff et al., "Monoclonal Antibody Homodimers. Enhanced Antitumor Activity in Nude Mice," *Cancer Research* 53:2560-2565, 1993.
Wolter et al., "Movement of Bax from the Cytosol to Mitochondria during Apoptosis," *The Journal of Cell Biology* 139(5): 1281-1292, 1997.
Worland et al., "Alteration of the Phosphorylation State of p34$^{cdc2}$ Kinase by the Flavone L86-8275 in Breast Carcinoma Cells," *Biochemical Pharmacology* 46(10):1831-1840, 1993.
Woyach et al., "Targeted therapies in CLL: mechanisms of resistance and strategies for management," *Blood* 126:471-477, 2015.
Wyatt et al., "Identification of N-(4-Piperidinyl)-4-(2,6-dichlorobenzoylamino)-1H-pyrazole-3-carboxamide (AT7519), a Novel Cyclin Dependent Kinase Inhibitor Using Fragment-Based X-Ray Crystallography and Structure Based Drug Design," *J. Med. Chem.* 51:4986-4999, 2008.
Yamaguchi et al., "Bcl-XL Protects BimEL-induced Bax Conformational Change and Cytochrome c Release Independent of Interacting with Bax or BimEL," *The Journal of Biological Chemistry* 277(44):41604-41612, 2002.
Yang et al., "[11] Calculation of Protein Conformation from Circular Dichroism," *Methods Enzymol* 130:208-269, 1986.
Yang et al., "Bad, a Heterodimeric Partner for Bcl-x$_L$ and Bcl-2, Displaces Bax and Promotes Cell Death," *Cell* 80:285-291, 1995.
Yang et al., "A novel liposomal formulation of flavopiridol," *International Journal of Pharmaceutics* 365:170-174, 2009.
Yang et al., "Bone marrow stroma-mediated resistance to FLT3 inhibitors in FLT3-ITD AML is mediated by persistent activation of extracellular regulated kinase," *British Journal of Haematology* 164:61-72, 2014.
Yasuda et al., "BNIP3α: A Human Homolog of Mitochondrial Proapoptotic Protein BNIP3," *Cancer Research* 59:533-537, 1999.
Yi et al., "Inhibition of Bid-induced Apoptosis by Bcl-2," *The Journal of Biological Chemistry* 278(19):16992-16999, 2003.
Yu et al., "Catalytic site remodelling of the DOT1L methyltransferase by selective inhibitors," *Nature Communications* 3:1288, 2012. (12 pages).
Zeng et al., "Targeting the leukemia microenvironment by CXCR4 inhibition overcomes resistance to kinase inhibitors and chemotherapy in AML," *Blood* 113:6215-6224, 2009.
Zha et al., "Serine Phosphorylation of Death Agonist BAD in Response to Survival Factor Results in Binding to 14-3-3 Not BCL-X$_L$," *Cell* 87:619-628, 1996.

(56) References Cited

OTHER PUBLICATIONS

Zha et al., "BH3 Domain of BAD Is Required for Heterodimerization with BCL-$X_L$ and Pro-apoptotic Activity," *The Journal of Biological Chemistry* 272(39):24101-24104, 1997.

Zha et al., "Posttranslational N-Myristoylation of BID as a Molecular Switch for Targeting Mitochondria and Apoptosis," *Science* 290:1761-1765, 2000.

Zhai et al., "Clinical pharmacology and pharmacogenetics of flavopiridol 1-h i.v. infusion in patients with refractory neoplasms," *Anti-Cancer Drugs* 14:125-135, 2003.

Zhao et al., "The Making of I-BET762, a BET Bromodomain Inhibitor Now in Clinical Development," *J. Med. Chem.* 56:7498-7500, 2013.

Zhou et al., "Novel mutant-selective EGFR kinase inhibitors against EGFR T790M," *Nature* 462(7276):1070-1074, 2009.

Zong et al., "BH3-only proteins that bind pro-survival Bcl-2 family members fail to induce apoptosis in the absence of Bax and Bak," *Genes & Development* 15:1481-1486, 2001.

Kasper, et al., Blood Cancer Journal, 2012, 2(3): 1-10.

Choudhary, et al., Cell Death Dis. 2015, e 1593: 1-12.

Tsao, et al, Ann Hemtoal, 2012, 91(12): 1861-1870.

\* cited by examiner

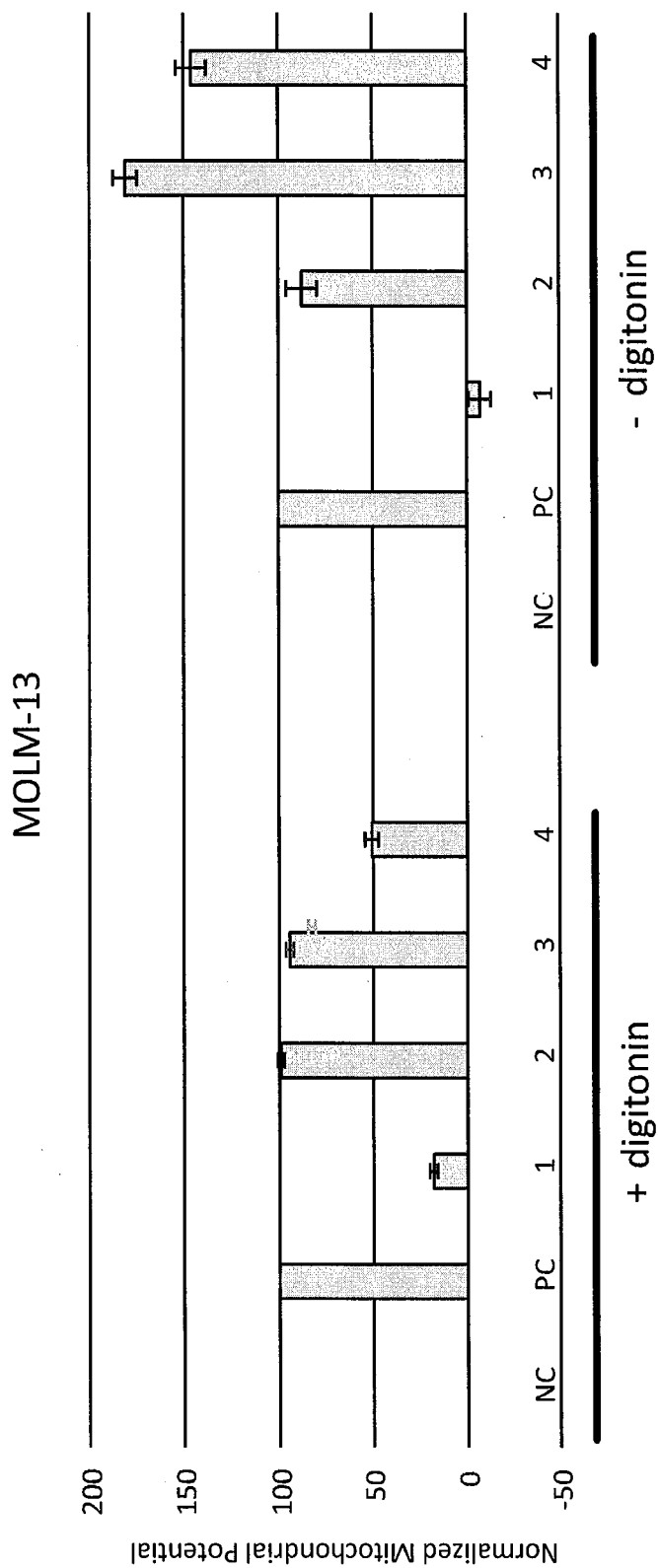

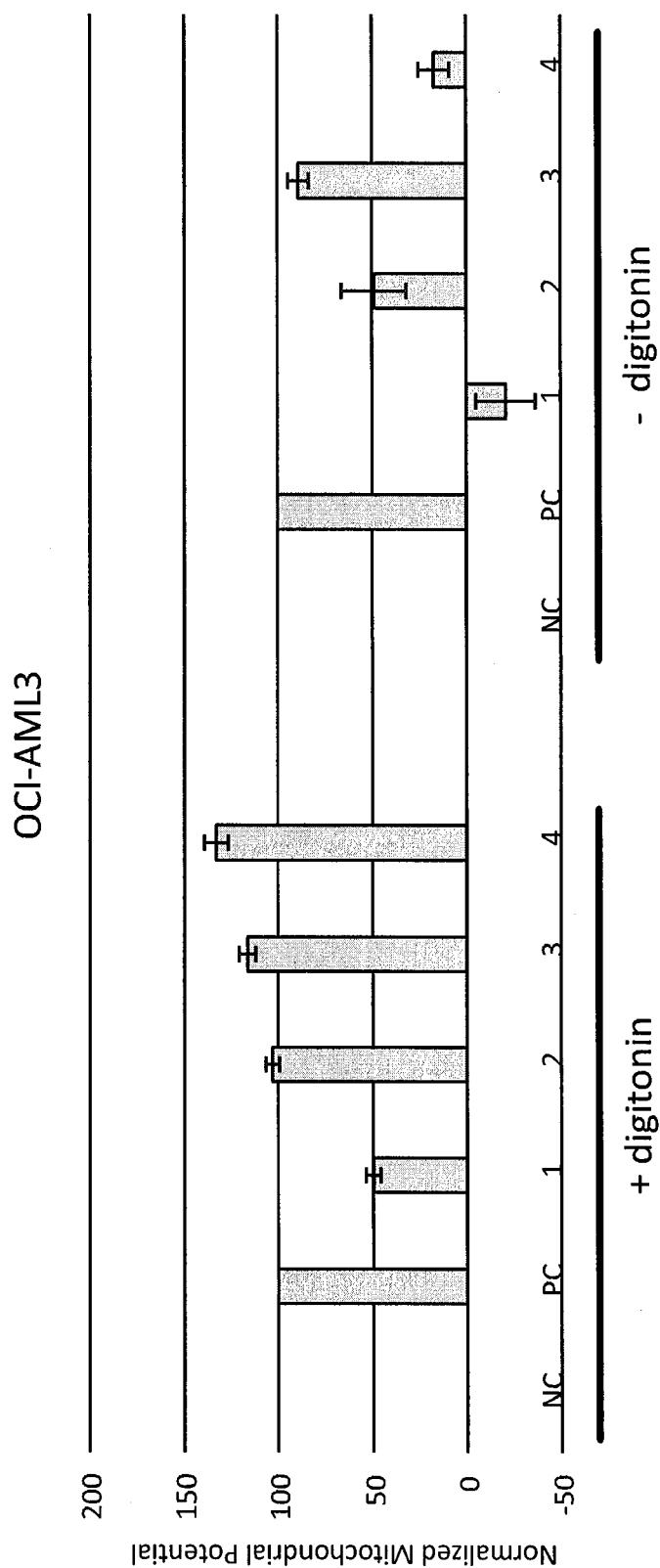

PROFILING PEPTIDES AND METHODS FOR SENSITIVITY PROFILING

STATEMENT REGARDING SEQUENCE LISTING

The Sequence Listing associated with this application is provided in text format in lieu of a paper copy, and is hereby incorporated by reference into the specification. The name of the text file containing the Sequence Listing is 910208_428C1_SEQUENCE_LISTING.txt. The text file is 6 KB, was created on Jun. 28, 2018, and is being submitted electronically via EFS-Web.

FIELD

The present disclosure is generally directed to profiling peptides, compositions, and kits, as well as methods for predicting sensitivity of a cancer to a treatment, selecting a treatment for a cancer, producing a sensitivity profile for a cancer, and treating a cancer. In some embodiments, the treatment includes administration of a therapeutic agent that is a cyclin-dependent kinase 9 (CDK9) inhibitor.

BACKGROUND

While there have been advances in cancer treatment, chemotherapy remains largely inefficient and ineffective. One reason for the generally poor performance of chemotherapy is that the selected treatment is often not closely matched to the genetic and molecular dependencies of an individual's disease.

For example, cancer cells exhibit abnormalities, such as DNA damage, genetic instability, abnormal growth factor signaling, and abnormal or missing matrix interactions, any of which should typically induce apoptosis through the intrinsic (mitochondrial) apoptosis pathway. As a result of these aberrant phenotypes, cancer cells develop blocks in apoptosis pathways that allow the cells to survive rather than respond to the apoptosis signals. As many cancer therapies rely on apoptosis to be effective, modulation of apoptosis by a specific anti-apoptotic protein may relate to responsiveness to particular therapy.

The concept of "oncogene addiction" describes the phenomena of the acquired dependence of cancer cells on, or addiction to, particular proteins for survival. These dependencies make some cancer cells both resistant to particular therapies, and, surprisingly, sensitive to other therapies.

Dependence by cancer cells on the anti-apoptotic Bcl-2 family proteins frequently relates to their otherwise unintended survival. Cancer cells generally rely on one Bcl-2 family member or another (e.g. Bcl-2, Bcl-xL, Mcl-1) to suppress cell death signals and resist apoptosis. Bcl-2 family proteins are regulated by distinct protein-protein interactions between pro-survival (i.e., anti-apoptotic) and pro-apoptotic members. These interactions occur primarily through Bcl-2 homology domain-3 (BH3) mediated binding and can have various outcomes, including homeostasis, cell death, sensitization to apoptosis, and blockade of apoptosis. Many cancer cells in which apoptotic signaling is blocked have an accumulation of the BH3 only activator proteins at the mitochondrial surface, a result of these proteins being sequestered by the anti-apoptotic proteins. This accumulation and proximity to their effector target proteins accounts for increased sensitivity to antagonism of Bcl-2 family proteins in the "primed" state. Accordingly, measurement of the functionality of anti-apoptotic Bcl-2 family proteins have proven to provide sound predictions for the dependency cancer cells have on a given Bcl-2 family member and how a cancer subject will respond to a treatment.

There are two main profiling assays currently used for BH3 profiling. The primary difference in the two commonly used assays is the use of flow cytometry to measure the response versus a fluorescence microplate reader. Using flow cytometry requires fluorescently labeling the cells with antibodies directed toward various cell surface markers and using the gating functions on the flow cytometer to only measure the response in the malignant population of cells. In short, after isolating leukocytes from a sample, the cells are labeled, the outer membrane is permeabilized, contacted with a BH3 peptide (e.g., NOXA), and stained with JC-1 fluorescent dye. Then, flow cytometry is used to quantify the response.

Alternatively, a microplate reader uses cell surface marker antibodies and cell separation techniques to isolate the malignant population of cells. After isolating leukocytes from a sample, the cells of interest are purified, the outer membrane is permeabilized, contacted with a BH3 peptide (e.g., NOXA), and stained with JC-1 fluorescent dye. Then, a microplate reader is used to quantify the response.

Both approaches generally require the cancer cells to be permeabilized by digitonin, which allows fragments of Bcl-2 family peptides (such as NOXA, BIM, etc.) to enter the cell and interact with mitochondrial proteins. In most assays using the standard NOXA peptide, this step is essential. However, cell permeabilization adds complexity, introduces significant variation to the assay, and increases the overall assay run time, all of which introduce technical challenges to providing accurate profiling results that are cost effective. As digitonin non-selectively permeabilizes biological membranes, including the mitochondrial membrane (Hoppel, C, and Cooper, C. Biochem J. 1968 April; 107(3): 367-375), the assays that use digitonin generally require precise titration of the digitonin such that the concentration used is within the window that permeabilizes the outer cellular membrane with minimal effects on the mitochondrial membrane. This window of digitonin concentration and treatment time is narrow, may vary between different cell types, and is directly related to having a robust assay that produces accurate results. This challenge is traditionally overcome currently by performing the assay at a single central laboratory that has the experience and the appropriate controls to ensure the assay is performed correctly. Thus, the cell permeabilization step is a challenge for decentralizing the use of such assays, for example, in producing an in vitro diagnostic kit that may be used in clinical laboratories.

Accordingly, improved methods of measuring the functionality of anti-apoptotic Bcl-2 proteins that are more accurate, reproducible, and cost-effective are needed.

BRIEF SUMMARY

In one aspect, the present disclosure provides a profiling peptide comprising a cellular uptake moiety and an Mcl-1 binding domain, the Mcl-1 binding domain having the sequence of SEQ ID NO:1 with 0-8 modifications.

In another aspect, the present disclosure provides a composition comprising a profiling peptide comprising a cellular uptake moiety and an Mcl-1 binding domain, the Mcl-1 binding domain having the sequence of SEQ ID NO:1 with 0-8 modifications, and a carrier.

In further aspects, the present disclosure provides a kit comprising: a profiling peptide comprising a cellular uptake moiety and an Mcl-1 binding domain, the Mcl-1 binding domain having the sequence of SEQ ID NO:1 with 0-8 modifications; and a detecting agent.

In aspects, the present disclosure provides a method for treating a cancer in a subject in need thereof, the method comprising administering a treatment regimen comprising a therapeutic agent to a subject having an Mcl-1 dependency percentage above a predetermined value, the Mcl-1 dependency percentage having been obtained by an in vitro method comprising contacting a first portion of a plurality of cancer cells with a profiling peptide comprising a cellular uptake moiety and an Mcl-1 binding domain, the Mcl-1 binding domain having the sequence of SEQ ID NO:1 with 0-8 modifications, or a composition comprising a profiling peptide comprising a cellular uptake moiety and an Mcl-1 binding domain, the Mcl-1 binding domain having the sequence of SEQ ID NO:1 with 0-8 modifications and a carrier.

In other embodiments, the present disclosure provides a method of predicting sensitivity of a cancer cell from a subject to a therapeutic agent, the method comprising: contacting the cancer cell with a profiling peptide comprising a cellular uptake moiety and an Mcl-1 binding domain, the Mcl-1 binding domain having the sequence of SEQ ID NO:1 with 0-8 modifications; and detecting a change in mitochondrial integrity of the cancer cell; wherein a decrease in mitochondrial integrity indicates that the cancer cell is sensitive to the therapeutic agent.

In further embodiments, the present disclosure provides a method of treating a cancer in a subject in need thereof, the method comprising: contacting a cancer cell from the subject with a profiling peptide comprising a cellular uptake moiety and an Mcl-1 binding domain, the Mcl-1 binding domain having the sequence of SEQ ID NO:1 with 0-8 modifications; detecting a change in mitochondrial integrity of the cancer cell; and administering an effective amount of a therapeutic agent to the subject if a decrease in mitochondrial integrity is detected, thereby treating the cancer in the subject.

In another aspect, the present disclosure provides a method of producing a sensitivity profile for a plurality of cancer cells from a subject, the method comprising: contacting a first portion of the plurality of cancer cells with a profiling peptide comprising a cellular uptake moiety and an Mcl-1 binding domain, the Mcl-1 binding domain having the sequence of SEQ ID NO:1 with 0-8 modifications, or a composition comprising a profiling peptide comprising a cellular uptake moiety and an Mcl-1 binding domain, the Mcl-1 binding domain having the sequence of SEQ ID NO:1 with 0-8 modifications and a carrier; and detecting a change in mitochondrial integrity of the first portion of the plurality of cancer cells.

In yet further embodiments, the present disclosure provides a method of selecting a therapeutic agent for treating a cancer in a subject, the method comprising: receiving a sensitivity profile for a cancer cell of the subject, the sensitivity profile comprising mitochondrial integrity data of the cancer cell when contacted with a profiling peptide comprising a cellular uptake moiety and an Mcl-1 binding domain, the Mcl-1 binding domain having the sequence of SEQ ID NO:1 with 0-8 modifications; and selecting the therapeutic agent to treat the subject if the mitochondrial integrity data shows a decrease in mitochondrial integrity.

In further embodiments, the present disclosure provides a method of treating a cancer in a subject in need thereof, the method comprising: receiving a sensitivity profile for a cancer cell of the subject, the sensitivity profile comprising mitochondrial integrity data of the cancer cell when contacted with a profiling peptide comprising a cellular uptake moiety and an Mcl-1 binding domain, the Mcl-1 binding domain having the sequence of SEQ ID NO:1 with 0-8 modifications; and administering an effective amount of a therapeutic agent to the subject if the mitochondrial integrity data shows a decrease in mitochondrial integrity, thereby treating the cancer in the subject.

In still further embodiments, the present disclosure provides a method of predicting sensitivity of a cancer cell from a subject to a therapeutic agent, the method comprising: contacting the cancer cell with a profiling peptide comprising a cellular uptake moiety and an Mcl-1 binding domain, the Mcl-1 binding domain having the sequence of SEQ ID NO:1 with 0-8 modifications; detecting a change in mitochondrial integrity of the cancer cell; and determining an Mcl-1 dependency percentage for the cancer cell based at least on the change in mitochondrial integrity, wherein an Mcl-1 dependency percentage above a predetermined value indicates that the cancer cell is sensitive to the therapeutic agent.

In other embodiments, the present disclosure provides a method of treating a cancer in a subject in need thereof, the method comprising: contacting a cancer cell from the subject with a profiling peptide comprising a cellular uptake moiety and an Mcl-1 binding domain, the Mcl-1 binding domain having the sequence of SEQ ID NO:1 with 0-8 modifications; detecting a change in mitochondrial integrity of the cancer cell; determining an Mcl-1 dependency percentage for the cancer cell based at least on the change in mitochondrial integrity; and administering an effective amount of a therapeutic agent to the subject if the Mcl-1 dependency percentage is above a predetermined value, thereby treating the cancer in the subject.

In other embodiments, the present disclosure provides a method of producing a sensitivity profile for a cancer cell from a subject, the method comprising: contacting the cancer cell with a profiling peptide comprising a cellular uptake moiety and an Mcl-1 binding domain, the Mcl-1 binding domain having the sequence of SEQ ID NO:1 with 0-8 modifications; detecting a change in mitochondrial integrity of the cancer cell; and determining an Mcl-1 dependency percentage for the cancer cell based at least on the change in mitochondrial integrity.

In yet other embodiments, the present disclosure provides a method of selecting a therapeutic agent for treating a cancer in a subject, the method comprising: receiving a sensitivity profile for a cancer cell of the subject, the sensitivity profile comprising Mcl-1 dependency data for the cancer cell, the Mcl-1 dependency data determined based at least on a change in mitochondrial integrity of the cancer cell when contacted with a profiling peptide comprising a cellular uptake moiety and an Mcl-1 binding domain, the Mcl-1 binding domain having the sequence of SEQ ID NO:1 with 0-8 modifications; and selecting the therapeutic agent to treat the subject if the Mcl-1 dependency data shows an Mcl-1 dependency percentage above a predetermined value.

In still other embodiments, the present disclosure provides a method of treating a cancer in a subject in need thereof, the method comprising: receiving a sensitivity profile for cancer cells of the subject, the sensitivity profile comprising Mcl-1 dependency data for the cancer cell, the Mcl-1 dependency data being determined based at least on a change in mitochondrial integrity of the cancer cell when contacted with a profiling peptide comprising a cellular uptake moiety and an Mcl-1 binding domain, the Mcl-1 binding domain having the sequence of SEQ ID NO:1 with 0-8 modifications; and administering an effective amount of a therapeutic agent to the subject if the Mcl-1 dependency data shows an Mcl-1 dependency percentage above a predetermined value, thereby treating the cancer in the subject.

In another aspect, the present disclosure provides a method of producing a sensitivity profile for a plurality of cancer cells from a subject, the method comprising isolating the plurality of cancer cells from a sample, contacting the plurality of cancer cells with a stain, treating a first portion of the plurality of cancer cells with a negative control, treating a second portion of the plurality of cancer cells with a positive control, treating a third portion of the plurality of cancer cells with a profiling peptide comprising a cellular uptake moiety and an Mcl-1 binding domain, the Mcl-1 binding domain having the sequence of SEQ ID NO:1 with 0-8 modifications, or a composition comprising a profiling peptide comprising a cellular uptake moiety and an Mcl-1 binding domain, the Mcl-1 binding domain having the sequence of SEQ ID NO:1 with 0-8 modifications and a carrier, contacting the first portion, the second portion, and the third portion of the plurality of cancer cells with a dye, and analyzing the first portion, the second portion, and the third portion of the plurality of cancer cells by flow cytometry.

In a further aspect, the present disclosure provides a therapeutic composition for use in the treatment of cancer in a subject with a Mcl-1 dependency percentage of at least 15%, the Mcl-1 dependency percentage having been obtained by an in vitro method comprising: contacting a first portion of a plurality of cancer cells with a profiling peptide comprising a cellular uptake moiety and an Mcl-1 binding domain, the Mcl-1 binding domain having the sequence of SEQ ID NO:1 with 0-8 modifications, or a composition comprising a profiling peptide comprising a cellular uptake moiety and an Mcl-1 binding domain, the Mcl-1 binding domain having the sequence of SEQ ID NO:1 with 0-8 modifications and a carrier.

In yet further aspects, the present disclosure provides a therapeutic composition for cancer comprising a therapeutic agent, which is administered to a subject having a Mcl-1 dependency percentage of at least 15%, wherein, the Mcl-1 dependency percentage is obtained by an in vitro method comprising: contacting a first position of plurality of cancer cells with a profiling peptide comprising a cellular uptake moiety and an Mcl-1 binding domain, the Mcl-1 binding domain having the sequence of SEQ ID NO:1 with 0-8 modifications, or a composition comprising a profiling peptide comprising a cellular uptake moiety and an Mcl-1 binding domain, the Mcl-1 binding domain having the sequence of SEQ ID NO:1 with 0-8 modifications and a carrier.

BRIEF DESCRIPTION OF THE FIGURES

FIGS. 1A-1D show the results of a whole cell assay of the profiling peptides described herein compared to NOXA.

DETAILED DESCRIPTION

Figure 2:
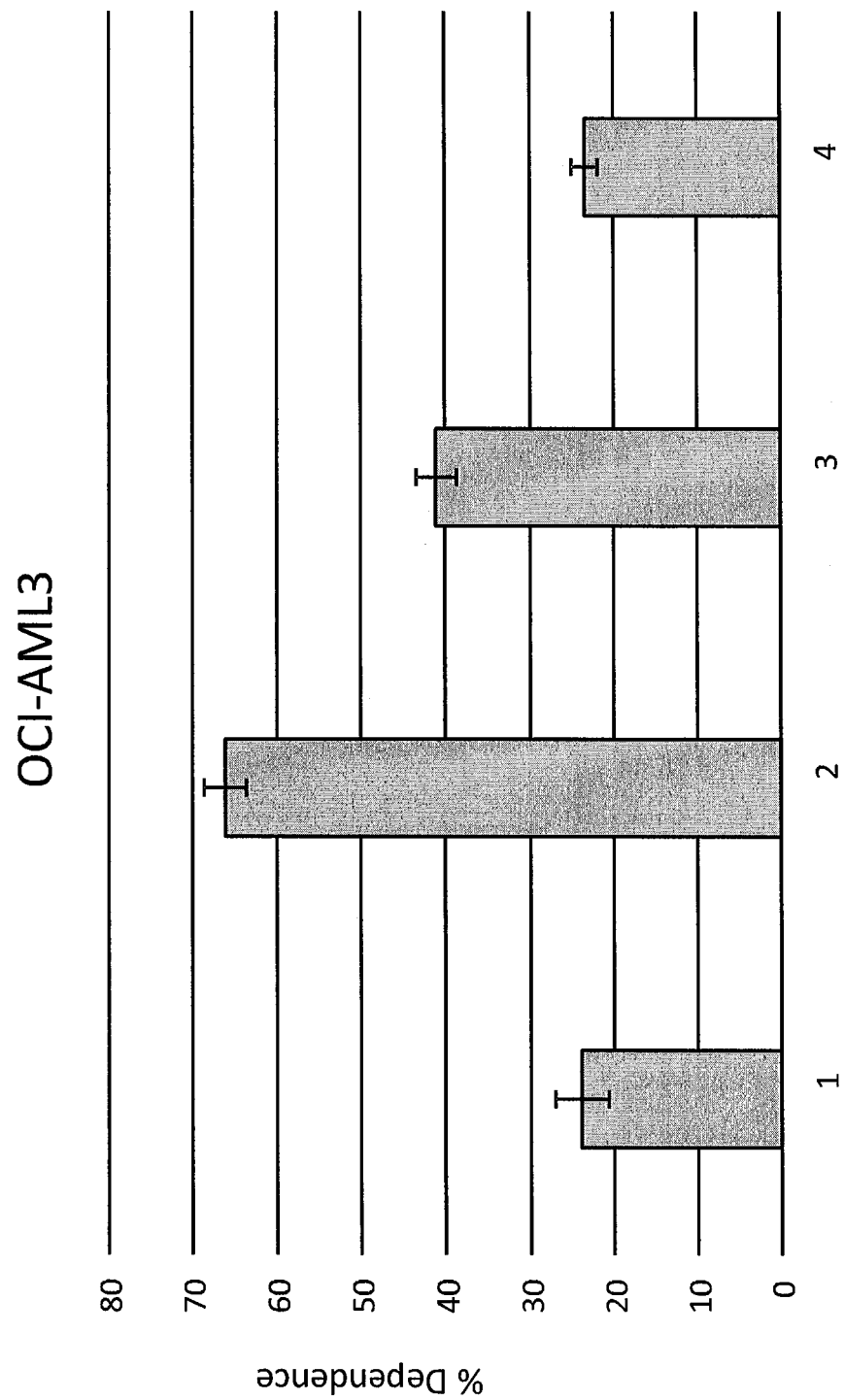
FIG. 2 shows the Mcl-1 dependency percentages for varying concentrations of a profiling peptide described herein compared to NOXA.

The present disclosure relates to profiling peptides comprising an optionally modified Mcl-1 binding domain having the sequence of any one of SEQ ID NOS:1-11, as well as compositions, methods of use, and kits. More specifically, the profiling peptides optionally include a cellular uptake moiety and an Mcl-1 binding domain, the Mcl-1 binding domain having the sequence of SEQ ID NO:1 with 0-8 modifications. In some embodiments, the profiling peptides comprise a cellular uptake moiety and an Mcl-1 binding domain having the sequence of any one of SEQ ID NO:1-11. The methods of using such profiling peptides include predicting sensitivity of a cancer cell, selecting a therapeutic agent, treating a cancer, producing a sensitivity profile, and the like.

Prior to setting forth this disclosure in more detail, it may be helpful to an understanding thereof to provide definitions of certain terms to be used herein. Additional definitions are set forth throughout this disclosure.

"Optional" or "optionally" means that the subsequently described element, component, event, or circumstance may or may not occur, and that the description includes instances in which the element, component, event, or circumstance occurs and instances in which they do not.

"Peptide" refers to a polymer of amino acid residues. Peptides include naturally occurring amino acid polymers and non-naturally occurring amino acid polymers, as well as amino acid polymers in which one or more amino acid residues is an artificial chemical mimetic of a corresponding naturally occurring amino acid.

As used herein, "amino acid" refers to naturally occurring amino acids and synthetic amino acids, as well as amino acid analogs and amino acid mimetics that function in a manner similar to the naturally occurring amino acids. Naturally occurring amino acids are those encoded by the genetic code, as well as those amino acids that are later modified, e.g., hydroxyproline, γ-carboxyglutamate, and O-phosphoserine. Amino acid analogs refer to compounds that have the same basic chemical structure as a naturally occurring amino acid, i.e., an α-carbon that is bound to a hydrogen, a carboxyl group, an amino group, and an R group (e.g., homoserine, norleucine, methionine sulfoxide, and methionine methyl sulfonium). Such analogs have modified R groups (e.g., norleucine) or modified peptide backbones, but retain the same basic chemical structure as a naturally occurring amino acid. Amino acid mimetics refer to chemical compounds that have a structure that is different from the general chemical structure of an amino acid, but that function in a manner similar to a naturally occurring amino acid.

A "cancer," including a "tumor," refers to an uncontrolled growth of cells and/or abnormal increased cell survival and/or inhibition of apoptosis which interferes with the normal functioning of the bodily organs and systems. "Cancer" (e.g., a tumor) includes solid and non-solid cancers. A subject that has a cancer or a tumor has an objectively measurable number of cancer cells present in the subject's body. "Cancers" include benign and malignant cancers (e.g., benign and malignant tumors, respectively), as well as dormant tumors or micrometastases. "Cancers" include acute lymphoblastic leukemia (ALL), acute myeloid leukemia (AML), adrenocortical carcinoma, AIDS-related cancers, anal cancer, appendix cancer, astrocytoma (e.g. childhood cerebellar or cerebral), basal-cell carcinoma, bile duct cancer, bladder cancer, bone tumor (e.g. osteosarcoma, malignant fibrous histiocytoma), brainstem glioma, brain cancer, brain tumors (e.g. cerebellar astrocytoma, cerebral astrocytoma/malignant glioma, ependymoma, medulloblastoma, supratentorial primitive neuroectodermal tumors, visual pathway and hypothalamic glioma), breast cancer, bronchial adenomas/carcinoids, Burkitt's lymphoma, carcinoid tumors, central nervous system lymphomas, cerebellar astrocytoma, cervical cancer, chronic lymphocytic leukemia (CLL), chronic myelogenous leukemia (CML), chronic myeloproliferative disorders, colon cancer, cutaneous t-cell lymphoma, desmoplastic small round cell tumor, endometrial cancer, ependymoma, esophageal cancer, Ewing's sarcoma, extracranial germ cell tumor, extragonadal germ cell tumor, extrahepatic bile duct cancer, eye cancer, gallbladder cancer, gastric (stomach) cancer, gastrointestinal stromal tumor (GIST), germ cell tumor (e.g. extracranial, extragonadal, ovarian), gestational trophoblastic tumor, gliomas (e.g. brain stem, cerebral astrocytoma, visual pathway and hypothalamic), gastric carcinoid, head and neck cancer, heart cancer, hepatocellular (liver) cancer, hypopharyngeal cancer, hypothalamic and visual pathway glioma, intraocular melanoma, islet cell carcinoma (endocrine pancreas), kidney cancer (renal cell cancer), laryngeal cancer, leukemias (e.g. acute lymphocytic leukemia, acute myelogenous leukemia, chronic lymphocytic leukemia, chronic myeloid leukemia, hairy cell), lip and oral cavity cancer, liposarcoma, liver cancer, lung cancer (e.g. non-small cell, small cell), lymphoma (e.g. AIDS-related, Burkitt, cutaneous T-cell Hodgkin, non-Hodgkin, primary central nervous system), medulloblastoma, melanoma, Merkel cell carcinoma, mesothelioma, metastatic squamous neck cancer, mouth cancer, multiple endocrine neoplasia syndrome, multiple myeloma, mycosis fungoides, myelodysplastic syndromes, myelodysplastic/myeloproliferative diseases, myelogenous leukemia, myeloid leukemia, myeloid leukemia, myeloproliferative disorders, chronic, nasal cavity and paranasal sinus cancer, nasopharyngeal carcinoma, neuroblastoma, non-Hodgkin lymphoma, non-small cell lung cancer, oral cancer, oropharyngeal cancer, osteosarcoma, ovarian cancer, pancreatic cancer, pancreatic cancer, paranasal sinus and nasal cavity cancer, parathyroid cancer, penile cancer, pharyngeal cancer, pheochromocytoma, pineal astrocytoma and/or germinoma, pineoblastoma and supratentorial primitive neuroectodermal tumors, pituitary adenoma, plasma cell neoplasia/multiple myeloma, pleuropulmonary blastoma, primary central nervous system lymphoma, prostate cancer, rectal cancer, renal cell carcinoma (kidney cancer), renal pelvis and ureter, retinoblastoma, rhabdomyosarcoma, salivary gland cancer, sarcoma (e.g. Ewing family, Kaposi, soft tissue, uterine), Sézary syndrome, skin cancer (e.g. non-melanoma, melanoma, merkel cell), small cell lung cancer, small intestine cancer, soft tissue sarcoma, squamous cell carcinoma, squamous neck cancer, stomach cancer, supratentorial primitive neuroectodermal tumor, t-cell lymphoma, testicular cancer, throat cancer, thymoma and thymic carcinoma, thyroid cancer, trophoblastic tumors, ureter and renal pelvis cancers, urethral cancer, uterine cancer, uterine sarcoma, vaginal cancer, visual pathway and hypothalamic glioma, vulvar cancer, Waldenström macroglobulinemia, or Wilms tumor.

"Metastasis" refers to the spread of cancer from its primary site to other places in the body. "Metastases" are cancers which migrate from their original location and seed vital organs, which can eventually lead to the death of the subject through the functional deterioration of the affected organs. Metastasis is a sequential process, where cancer cells can break away from a primary tumor, penetrate into lymphatic and blood vessels, circulate through the bloodstream, and grow in a distant focus (metastasize) in normal tissues elsewhere in the body. At the new site, the cells establish a blood supply and can grow to form a life-threatening mass. Metastasis can be local or distant. Both stimulatory and inhibitory molecular pathways within the tumor cell regulate this behavior, and interactions between the tumor cell and host cells in the new site are also significant.

"Subject" includes humans, domestic animals, such as laboratory animals (e.g. dogs, monkeys, rats, mice, etc.), household pets (e.g., cats, dogs, rabbits, etc.), and livestock (e.g., pigs, cattle, sheep, goats, horses, etc.), and non-domestic animals (e.g., bears, elephants, porcupines, etc.). In embodiments, a subject is a human.

"Treating" or "treatment" as used herein refers to the administration of a medication or medical care to a subject, such as a human, having a disease or condition of interest, e.g., a cancer, including: (i) preventing the disease or condition from occurring in a subject, in particular, when such subject is predisposed to the condition but has not yet been diagnosed as having it; (ii) inhibiting the disease or condition, i.e., arresting its development; (iii) relieving the disease or condition, i.e., causing regression of the disease or condition; or (iv) relieving the symptoms resulting from the disease or condition, (e.g., pain, weight loss, cough, fatigue, weakness, etc.) without addressing the underlying disease or condition. As used herein, the terms "disease" and "condition" may be used interchangeably or may be different in that the particular malady or condition may not have a known causative agent (so that etiology has not yet been confirmed) and it is therefore not yet recognized as a disease but only as an undesirable condition or syndrome, wherein a more or less specific set of symptoms have been identified by clinicians.

"Effective amount" refers to the amount of a compound or composition which, when administered to a subject, such as a human, is sufficient to effect treatment of the subject's cancer. The amount of a compound or composition that constitutes an "effective amount" will vary depending on the compound or composition, the condition being treated and its severity, the manner of administration, the duration of treatment, and/or the age of the subject to be treated, but can be determined routinely by one of ordinary skill in the art based on his own knowledge and this disclosure. In embodiments, an "effective amount" effects treatment (e.g., treats, prevents, inhibits, relieves, promotes, improves, increases, reduces, and the like) as measured by a statistically significant change in one or more indications, symptoms, signs, diagnostic tests, vital signs, and the like. In other embodiments, an "effective amount" suppresses, manages, or prevents a condition as measured by a lack of a statistically significant change in one or more indications, symptoms, signs, diagnostic tests, vital signs, and the like.

As used herein, "statistically significant" refers to a p value of 0.050 or less when calculated using the Students t-test and indicates that it is unlikely that a particular event or result being measured has arisen by chance.

In the present description, any concentration range, percentage range, ratio range, or integer range is to be understood to include the value of any integer within the recited range and, when appropriate, fractions thereof (such as one tenth and one hundredth of an integer), unless otherwise indicated. Also, any number range recited herein relating to any physical feature, such as polymer subunits, size, or thickness, are to be understood to include any integer within the recited range, unless otherwise indicated. As used herein, the term "about" means±20%, ±10%, ±5% or ±1% of the indicated range, value, or structure, unless otherwise indicated. It should be understood that the terms "a" and "an" as used herein refer to "one or more" of the enumerated components. The use of the alternative (e.g., "or") should be understood to mean either one, both, or any combination thereof of the alternatives. Unless the context requires otherwise, throughout the present specification and claims, the word "comprise" and variations thereof, such as, "comprises" and "comprising," as well as synonymous terms like "include" and "have" and variants thereof, are to be construed in an open, inclusive sense; that is, as "including, but not limited to," such that recitation of items in a list is not to the exclusion of other like items that may also be useful in the materials, compositions, devices, and methods of this technology. Although the open-ended term "comprising," as a synonym of terms such as including, containing, or having, is used herein to describe and claim the invention, the present technology, or embodiments thereof, may alternatively be described using more limiting terms such as "consisting of" or "consisting essentially of" the recited ingredients.

Unless defined otherwise, all technical and scientific terms herein have the same meaning as commonly understood by one of ordinary skill in the art to which this invention belongs.

Reference throughout this specification to "one embodiment" or "an embodiment" means that a particular feature, structure, or characteristic described in connection with the embodiment is included in at least one embodiment of the present disclosure. Thus, the appearances of the phrases "in one embodiment" or "in an embodiment" in various places throughout this specification are not necessarily all referring to the same embodiment. Similarly, the terms "can" and "may" and their variants are intended to be non-limiting, such that recitation that an embodiment can or may comprise certain elements or features does not exclude other embodiments of the present technology that do not contain those elements or features. Furthermore, the particular features, structures, or characteristics may be combined in any suitable manner in one or more embodiments.

In the following description, certain specific details are set forth in order to provide a thorough understanding of various embodiments of this disclosure. However, one skilled in the art will understand that the disclosure may be practiced without these details.

Profiling Peptides

As noted herein, the present disclosure provides profiling peptides. Generally, profiling peptides comprise an Mcl-1 binding domain having a sequence shown in Table 1, which may be optionally modified.

TABLE 1

Exemplary Mcl-1 Binding Domains.

| SEQ ID NO: | Sequence |
|---|---|
| 1 | RPEIWMTQGLRRLGDEINAYYAR |
| 2 | RPEIWLTQSLQRLGDEINAYYAR |
| 3 | RPEIWLTQHLQRLGDEINAYYAR |
| 4 | RPEIWMGQGLRRLGDEINAYYAR |
| 5 | RPEIWLGQSLQRLGDEINAYYAR |

TABLE 1-continued

Exemplary Mcl-1 Binding Domains.

| SEQ ID NO: | Sequence |
|---|---|
| 6 | RPEIWLGQHLQRLGDEINAYYAR |
| 7 | RPEIWITQELRRIGDEFNAYYAR |
| 8 | RPEIWMTQELRRIGDEFNAYYAR |
| 9 | RPEIWITQGLRRIGDEFNAYYAR |
| 10 | RPEIWITQELRRLGDEFNAYYAR |
| 11 | RPEIWITQELRRIGDEINAYYAR |

In some embodiments, a profiling peptide comprises an Mcl-1 binding domain having the sequence of any one of SEQ ID NOS:1-11 with 0-8 modifications. In some embodiments, a profiling peptide comprises an Mcl-1 binding domain having the sequence of any one of SEQ ID NOS: 1-11 with 1-8 modifications.

"Modified" peptides include peptides having one or more amino acid substitutions as compared to a sequence disclosed herein. The substitution can be a conservative or a non-conservative substitution. Modified peptides also include peptides having additions of amino acids to, or deletions of amino acids from, the original peptide sequence. Therefore, modified peptides include fragments of the original peptide sequence. In some embodiments, the modifications comprise one or more conservative amino acid substitutions, additions, deletions, or combinations thereof.

As used herein, a "modification" refers to a substitution, addition, or deletion of a single amino acid. Accordingly, when a number of modifications is referenced (e.g., an Mcl-1 binding domain having the sequence of SEQ ID NO:1 with two modifications), the number refers to the number of amino acids of the sequence that may be substituted, added, or deleted. In other words, each "substitution," "addition," or "deletion" replaces, adds, or removes a single amino acid, respectively, and does not refer to a single instance that replaces, adds, or removes more than one amino acid.

Modifications may be introduced by altering a polynucleotide encoding a profiling peptide, and may be performed by a variety of methods, including site-specific or site-directed mutagenesis. For example, mutations may be introduced at a particular location by synthesizing oligonucleotides containing a mutant sequence flanked by restriction sites enabling ligation to fragments of the unmodified sequence. Following ligation, the resulting sequence would encode a modified peptide having the desired amino acid addition, substitution, or deletion.

A "conservative substitution" includes a substitution found in one of the following conservative substitutions groups: Group 1: Alanine (Ala or A), Glycine (Gly or G), Serine (Ser or S), Threonine (Thr or T); Group 2: Aspartic acid (Asp or D), Glutamic acid (Glu or Z); Group 3: Asparagine (Asn or N), Glutamine (Gln or Q); Group 4: Arginine (Arg or R), Lysine (Lys or K), Histidine (His or H); Group 5: Isoleucine (Ile or I), Leucine (Leu or L), Methionine (Met or M), Valine (Val or V); and Group 6: Phenylalanine (Phe or F), Tyrosine (Tyr or Y), Tryptophan (Trp or W). Additionally or alternatively, amino acids can be grouped into conservative substitution groups by similar function or chemical structure or composition (e.g., acidic, basic, aliphatic, aromatic, or sulfur-containing). For example, an aliphatic grouping may include, for purposes of substitution, Gly, Ala, Val, Leu, and Ile. Other conservative substitutions groups include: sulfur-containing: Met and Cysteine (Cys or C); acidic: Asp, Glu, Asn, and Gln; small aliphatic, nonpolar or slightly polar residues: Ala, Ser, Thr, Proline (Pro or P), and Gly; polar, negatively charged residues and their amides: Asp, Asn, Glu, and Gln; polar, positively charged residues: His, Arg, and Lys; large aliphatic, nonpolar residues: Met, Leu, Ile, Val, and Cys; and large aromatic residues: Phe, Tyr, and Trp. Additional information can be found in Creighton (1984) Proteins, W.H. Freeman and Company.

In embodiments, the modifications described herein may include the substitution of a naturally-occurring amino acid with a synthetic amino acid, amino acid analog, or amino acid mimetic, or the addition of a synthetic amino acid, amino acid analog, or amino acid mimetic. In such embodiments, modifications can include the substitution of one more L-amino acids with D-amino acids. The D-amino acid can be the same amino acid type as that found in the natural sequence or can be a different amino acid.

"Modification" also includes the substitution of a naturally-occurring amino acid with an amino acid that has been conjugated to, or otherwise associated with, a functional group. Such an amino acid may be, e.g., a glycosylated amino acid, a PEGylated amino acid, a farnesylated amino acid, an acetylated amino acid, a biotinylated amino acid, an amino acid conjugated to a lipid moiety, or an amino acid conjugated to an organic derivatizing agent. The presence of such amino acids may be preferred to, for example, increase polypeptide storage stability, and/or increase peptide solubility. Such modifications can be performed co-translationally or post-translationally during recombinant production, or by synthetic means.

In embodiments, the profiling peptides described herein comprise an Mcl-1 binding domain (e.g., any one of SEQ ID NOS: 1-11) with 0 to 1 modifications. In some embodiments, the profiling peptides described herein comprise an Mcl-1 binding domain with 0 to 2 modifications. In some embodiments, the profiling peptides described herein comprise an Mcl-1 binding domain with 0 to 3 modifications. In some embodiments, the profiling peptides described herein comprise an Mcl-1 binding domain with 0 to 4 modifications. In some embodiments, the profiling peptides described herein comprise an Mcl-1 binding domain with 0 to 5 modifications. In some embodiments, the profiling peptides described herein comprise an Mcl-1 binding domain with 0 to 6 modifications. In some embodiments, the profiling peptides described herein comprise an Mcl-1 binding domain with 0 to 7 modifications. In some embodiments, the profiling peptides described herein comprise an Mcl-1 binding domain with 0 to 8 modifications. In some embodiments, the profiling peptides described herein comprise an Mcl-1 binding domain with 0 to 9 modifications, 0 to 10 modifications, 0 to 12 modifications, 0 to 15 modifications, or 0 to 20 modifications.

In some embodiments, the profiling peptides described herein comprise an Mcl-1 binding domain with 1 to 2 modifications. In some embodiments, the profiling peptides described herein comprise an Mcl-1 binding domain with 1 to 3 modifications. In some embodiments, the profiling peptides described herein comprise an Mcl-1 binding domain with 1 to 4 modifications. In some embodiments, the profiling peptides described herein comprise an Mcl-1 binding domain with 1 to 5 modifications. In some embodiments, the profiling peptides described herein comprise an Mcl-1 binding domain with 1 to 6 modifications. In some embodiments, the profiling peptides described herein comprise an Mcl-1 binding domain with 1 to 7 modifications. In some embodiments, the profiling peptides described herein comprise an Mcl-1 binding domain with 1 to 8 modifications. In some embodiments, the profiling peptides described herein comprise an Mcl-1 binding domain with 1 to 9 modifications. In some embodiments, the profiling peptides described herein comprise an Mcl-1 binding domain with 1 to 10 modifications, 1 to 12 modifications, 1 to 15 modifications, or 1 to 20 modifications. In some embodiments, the profiling peptides described herein comprise an Mcl-1 binding domain with 2 to 3 modifications. In some embodiments, the profiling peptides described herein comprise an Mcl-1 binding domain with 2 to 4 modifications. In some embodiments, the profiling peptides described herein comprise an Mcl-1 binding domain with 2 to 5 modifications. In some embodiments, the profiling peptides described herein comprise an Mcl-1 binding domain with 2 to 6 modifications. In some embodiments, the profiling peptides described herein comprise an Mcl-1 binding domain with 2 to 7 modifications. In some embodiments, the profiling peptides described herein comprise an Mcl-1 binding domain with 2 to 8 modifications. In some embodiments, the profiling peptides described herein comprise an Mcl-1 binding domain with 2 to 9 modifications, 2 to 10 modifications, 2 to 12 modifications, 2 to 15 modifications, or 2 to 20 modifications.

In some embodiments, the profiling peptides described herein comprise an Mcl-1 binding domain with 3 to 4 modifications. In some embodiments, the profiling peptides described herein comprise an Mcl-1 binding domain with 3 to 5 modifications. In some embodiments, the profiling peptides described herein comprise an Mcl-1 binding domain with 3 to 6 modifications. In some embodiments, the profiling peptides described herein comprise an Mcl-1 binding domain with 3 to 7 modifications. In some embodiments, the profiling peptides described herein comprise an Mcl-1 binding domain with 3 to 8 modifications. In some embodiments, the profiling peptides described herein comprise an Mcl-1 binding domain with 3 to 9 modifications, 3 to 10 modifications, 3 to 12 modifications, 3 to 15 modifications, 3 to 20 modifications, 4 to 5 modifications, 4 to 6 modifications, 4 to 7 modifications, 4 to 8 modifications, 4 to 9 modifications, 4 to 10 modifications, 4 to 12 modifications, 4 to 15 modifications, 4 to 20 modifications, 5 to 6 modifications, 5 to 7 modifications, 5 to 8 modifications, 5 to 9 modifications, 5 to 10 modifications, 5 to 12 modifications, 5 to 15 modifications, 5 to 20 modifications, 6 to 7 modifications, 6 to 8 modifications, 6 to 9 modifications, 6 to 10 modifications, 7 to 8 modifications, 7 to 9 modifications, 7 to 10 modifications, 8 to 9 modifications, 8 to 10 modifications, or 9 to 10 modifications. In some embodiments, the profiling peptides described herein comprise a modified Mcl-1 binding domain with 1, 2, 3, 4, 5, 6, 7, 8, 9, 10, 11, 12, 13, 14, 15, 16, 17, 18, 19, or 20 modifications. The Mcl-1 binding domain sequence included in a profiling peptide of the present disclosure may include a modification at any position.

In embodiments where the Mcl-1 binding domain is a fragment of any one of SEQ ID NOS:1-11, the amino acid sequence can have a minimum length of 5 amino acids, 6 amino acids, 7 amino acids, 8 amino acids, 9 amino acids, 10 amino acids, 11 amino acids, 12 amino acids, 13 amino acids, or 14 amino acids. In some embodiments where the Mcl-1 binding domain is a fragment of any one of SEQ ID NOS:1-11, the amino acid sequence can have a minimum length of 15 amino acids. In some embodiments where the Mcl-1 binding domain is a fragment of any one of SEQ ID NOS:1-11, the amino acid sequence can have a minimum length of 16 amino acids. In some embodiments where the Mcl-1 binding domain is a fragment of any one of SEQ ID NOS:1-11, the amino acid sequence can have a minimum length of 17 amino acids. In some embodiments where the Mcl-1 binding domain is a fragment of any one of SEQ ID NOS:1-11, the amino acid sequence can have a minimum length of 18 amino acids. In some embodiments where the Mcl-1 binding domain is a fragment of any one of SEQ ID NOS:1-11, the amino acid sequence can have a minimum length of 19 amino acids. In some embodiments where the Mcl-1 binding domain is a fragment of any one of SEQ ID NOS:1-11, the amino acid sequence can have a minimum length of 20 amino acids. In some embodiments where the Mcl-1 binding domain is a fragment of any one of SEQ ID NOS:1-11, the amino acid sequence can have a minimum length of 21 amino acids.

In some embodiments, the Mcl-1 binding domain is a fragment of SEQ ID NO:1, and the amino acid sequence has a minimum length of 5 amino acids, 6 amino acids, 7 amino acids, 8 amino acids, 9 amino acids, 10 amino acids, 11 amino acids, 12 amino acids, 13 amino acids, or 14 amino acids. In some embodiments, the Mcl-1 binding domain is a fragment of SEQ ID NO:1, and the amino acid sequence has a minimum length of 15 amino acids. In some embodiments, the Mcl-1 binding domain is a fragment of SEQ ID NO:1, and the amino acid sequence has a minimum length of 16 amino acids. In some embodiments, the Mcl-1 binding domain is a fragment of SEQ ID NO:1, and the amino acid sequence has a minimum length of 17 amino acids. In some embodiments, the Mcl-1 binding domain is a fragment of SEQ ID NO:1, and the amino acid sequence has a minimum length of 18 amino acids. In some embodiments, the Mcl-1 binding domain is a fragment of SEQ ID NO:1, and the amino acid sequence has a minimum length of 19 amino acids. In some embodiments, the Mcl-1 binding domain is a fragment of SEQ ID NO:1, and the amino acid sequence has a minimum length of 20 amino acids. In some embodiments, the Mcl-1 binding domain is a fragment of SEQ ID NO:1, and the amino acid sequence has a minimum length of 21 amino acids.

In further embodiments, the Mcl-1 binding domain comprises at least 10 contiguous amino acids of any one of SEQ ID NOS:1-11. In some embodiments, the Mcl-1 binding domain comprises at least 11 contiguous amino acids of any one of SEQ ID NOS:1-11. In some embodiments, the Mcl-1 binding domain comprises at least 12 contiguous amino acids of any one of SEQ ID NOS:1-11. In some embodiments, the Mcl-1 binding domain comprises at least 13 contiguous amino acids of any one of SEQ ID NOS:1-11. In some embodiments, the Mcl-1 binding domain comprises at least 14 contiguous amino acids of any one of SEQ ID NOS:1-11. In some embodiments, the Mcl-1 binding domain comprises at least 15 contiguous amino acids of any one of SEQ ID NOS:1-11. In some embodiments, the Mcl-1 binding domain comprises at least 16 contiguous amino acids of any one of SEQ ID NOS:1-11. In some embodiments, the Mcl-1 binding domain comprises at least 17 contiguous amino acids of any one of SEQ ID NOS:1-11. In some embodiments, the Mcl-1 binding domain comprises at least 18 contiguous amino acids of any one of SEQ ID NOS:1-11. In some embodiments, the Mcl-1 binding domain comprises at least 19 contiguous amino acids of any one of SEQ ID NOS:1-11. In some embodiments, the Mcl-1 binding domain comprises at least 20 contiguous amino acids of any one of SEQ ID NOS:1-11. In some embodiments, the Mcl-1 binding domain comprises at least 21 contiguous amino acids of any one of SEQ ID NOS:1-11. In some embodiments, the Mcl-1 binding domain comprises at least at least 10 contiguous amino acids of SEQ ID NO:1, at least 11 contiguous amino acids of SEQ ID NO:1, at least 12 contiguous amino acids of SEQ ID NO:1, at least 13 contiguous amino acids of SEQ ID NO:1, at least 14 contiguous amino acids of SEQ ID NO:1, at least 15 contiguous amino acids of SEQ ID NO:1, at least 16 contiguous amino acids of SEQ ID NO:1, at least 17 contiguous amino acids of SEQ ID NO:1, at least 18 contiguous amino acids of SEQ ID NO:1, at least 19 contiguous amino acids of SEQ ID NO:1, at least 20 contiguous amino acids of SEQ ID NO:1, or at least 21 contiguous amino acids of SEQ ID NO:1.

In some embodiments, the Mcl-1 binding domain comprises no more than 10 contiguous amino acids of any one of SEQ ID NOS:1-11, no more than 11 contiguous amino acids of any one of SEQ ID NOS:1-11, no more than 12 contiguous amino acids of any one of SEQ ID NOS:1-11, no more than 13 contiguous amino acids of any one of SEQ ID NOS:1-11, no more than 14 contiguous amino acids of any one of SEQ ID NOS:1-11, no more than 15 contiguous amino acids of any one of SEQ ID NOS:1-11, no more than 16 contiguous amino acids of any one of SEQ ID NOS:1-11, no more than 17 contiguous amino acids of any one of SEQ ID NOS:1-11, no more than 18 contiguous amino acids of any one of SEQ ID NOS:1-11, no more than 19 contiguous amino acids of any one of SEQ ID NOS:1-11, no more than 20 contiguous amino acids of any one of SEQ ID NOS:1-11, or no more than 21 contiguous amino acids of any one of SEQ ID NOS:1-11. In some embodiments, the Mcl-1 binding domain comprises no more than 10 contiguous amino acids of SEQ ID NO:1, no more than 11 contiguous amino acids of SEQ ID NO:1, no more than 12 contiguous amino acids of SEQ ID NO:1, no more than 13 contiguous amino acids of SEQ ID NO:1, no more than 14 contiguous amino acids of SEQ ID NO:1, no more than 15 contiguous amino acids of SEQ ID NO:1, no more than 16 contiguous amino acids of SEQ ID NO:1, no more than 17 contiguous amino acids of SEQ ID NO:1, no more than 18 contiguous amino acids of SEQ ID NO:1, no more than 19 contiguous amino acids of SEQ ID NO:1, no more than 20 contiguous amino acids of SEQ ID NO:1, or no more than 21 contiguous amino acids of SEQ ID NO:1.

Embodiments of the Mcl-1 binding domains disclosed herein include amino acid sequences with at least 70% sequence identity to the sequence of any one of SEQ ID NOS:1-11. In some embodiments, the Mcl-1 binding domain has at least 75% sequence identity with the sequence of any one of SEQ ID NOS:1-11. In some embodiments, the Mcl-1 binding domain has at least 80% sequence identity with the sequence of any one of SEQ ID NOS:1-11. In some embodiments, the Mcl-1 binding domain has at least 85% sequence with the sequence of any one of SEQ ID NOS:1-11. In some embodiments, the Mcl-1 binding domain has at least 90% sequence identity with the sequence of any one of SEQ ID NOS:1-11. In some embodiments, the Mcl-1 binding domain has at least 95% sequence identity with the sequence of any one of SEQ ID NOS:1-11. In some embodiments, the Mcl-1 binding domain has at least 96% sequence identity with the sequence of any one of SEQ ID NOS:1-11. In some embodiments, the Mcl-1 binding domain has at least 97% sequence identity with the sequence of any one of SEQ ID NOS:1-11. In some embodiments, the Mcl-1 binding domain has at least 98% sequence identity with the sequence of any one of SEQ ID NOS:1-11. In some embodiments, the Mcl-1 binding domain has at least 99% sequence identity with the sequence of any one of SEQ ID NOS:1-11.

In some embodiments, the Mcl-1 binding domain has a sequence with at least 70% sequence identity to the sequence of SEQ ID NO:1. In some embodiments, the Mcl-1 binding domain has a sequence with at least 75% sequence identity to the sequence of SEQ ID NO:1. In some embodiments, the Mcl-1 binding domain has a sequence with at least 80% sequence identity to the sequence of SEQ ID NO:1. In some embodiments, the Mcl-1 binding domain has a sequence with at least 85% sequence to the sequence of SEQ ID NO:1. In some embodiments, the Mcl-1 binding domain has a sequence with at least 90% sequence identity to the sequence of SEQ ID NO:1. In some embodiments, the Mcl-1 binding domain has a sequence with at least 95% sequence identity to the sequence of SEQ ID NO:1. In some embodiments, the Mcl-1 binding domain has a sequence with at least 96% sequence identity to the sequence of SEQ ID NO:1. In some embodiments, the Mcl-1 binding domain has a sequence with at least 97% sequence identity to the sequence of SEQ ID NO:1. In some embodiments, the Mcl-1 binding domain has a sequence with at least 98% sequence identity to the sequence of SEQ ID NO:1. In some embodiments, the Mcl-1 binding domain has a sequence with at least 99% sequence identity to the sequence of SEQ ID NO:1.

"Percent sequence identity" refers to a relationship between two or more sequences, as determined by comparing the sequences. Preferred methods to determine sequence identity are designed to give the best match between the sequences tested. For example, the sequences are aligned for optimal comparison purposes (e.g., gaps can be introduced in one or both of a first and a second amino acid or nucleic acid sequence for optimal alignment). Further, non-homologous sequences may be disregarded for comparison purposes. In embodiments, the length of a sequence aligned for comparison purposes is at least 70%, 80%, 90%, or 100% of the length of the reference sequence. In embodiments, the percent sequence identity referenced herein is calculated over the length of the reference sequence. Methods to determine sequence identity and similarity can be found in publicly available computer programs. Sequence alignments and percent identity calculations may be performed using a BLAST program (e.g., BLAST 2.0, BLASTP, BLASTN, or BLASTX). The mathematical algorithm used in the BLAST programs can be found in Altschul et al., Nucleic Acids Res. 25:3389-3402, 1997. Within the context of this disclosure it will be understood that where sequence analysis software is used for analysis, the results of the analysis are based on the "default values" of the program referenced. "Default values" mean any set of values or parameters which originally load with the software when first initialized.

In embodiments, a modified Mcl-1 binding domain retains the specificity and affinity for binding to Mcl-1 of the unmodified sequence (i.e., the modifications to the Mcl-1 binding domain do not alter the specificity or affinity for binding to Mcl-1 in a statistically significant, clinically significant, or biologically significant manner). In some embodiments, a modified Mcl-1 binding domain retains the specificity and affinity for binding to Mcl-1 of the unmodified sequence if the specificity and affinity of the modified Mcl-1 binding domain are at least 70%, 80%, 85%, 90%, 95%, 97%, or 99% of the specificity and affinity of the unmodified sequence. For example, a modified Mcl-1 binding domain may retain the specificity and affinity for binding to Mcl-1 of the unmodified sequence if the specificity and affinity of the modified Mcl-1 binding domain are at least 70%, 80%, 85%, 90%, 95%, 97%, or 99% of the specificity and affinity of any one of SEQ ID NOS: 1-11.

In embodiments, the Mcl-1 binding domain binds to Mcl-1 with at least a 20-fold increased affinity over NOXA. In some embodiments, the Mcl-1 binding domain binds to Mcl-1 with at least a 22-fold increased affinity over NOXA. In some embodiments, the Mcl-1 binding domain binds to Mcl-1 with at least a 24-fold increased affinity over NOXA. In particular embodiments, the Mcl-1 binding domain binds to Mcl-1 with at least a 28-fold increased affinity over NOXA.

The effect of any amino acid modification to an Mcl-1 binding domain may be determined empirically by testing the resulting modified Mcl-1 binding domain for the ability to function in a biological assay, or to bind to a target molecule, such as a monoclonal or polyclonal antibody. For example, the ability of the modified Mcl-1 binding domain to fold into a conformation comparable to the unmodified sequence can be tested using assays known in the art, including reacting with monoclonal or polyclonal antibodies that are specific for the native or unfolded peptides, testing the retention of binding functions, and testing the sensitivity or resistance of the modified Mcl-1 binding domain to digestion with proteases.

Analysis and/or computer modeling of the primary and secondary amino acid structure of the Mcl-1 binding domain to analyze the tertiary structure of the peptide may aid in identifying specific amino acid residues that can be substituted, added, or deleted without significantly altering the structure and as a consequence, potentially significantly reducing the binding specificity and affinity of the Mcl-1 binding domain.

In embodiments, profiling peptides of the present disclosure further comprise a cellular uptake moiety, which is optionally joined to the Mcl-1 binding domain by a linker. A "cellular uptake moiety" refers to an amino acid sequence or chemical compound that, when conjugated to a peptide, allows the peptide and the cellular uptake moiety to cross the outer cell membrane, thereby transferring the peptide into the cell. Additionally, in some embodiments, the cellular uptake moiety may act as a targeting moiety, such that it directs the peptide to a desired cellular location (e.g., the mitochondria).

In embodiments, the cellular uptake moiety is a peptide sequence. In such embodiments, the cellular uptake moiety peptide is at least four amino acids in length, at least five amino acids in length, at least six amino acids in length, at least seven amino acids in length, at least eight amino acids in length, or at least nine amino acids in length. In some embodiments, the cellular uptake moiety comprises an amino acid sequence of 1 to 20 amino acids, 5 to 20 amino acids, 6 to 20 amino acids, 7 to 20 amino acids, 8 to 20 amino acids, 9 to 20 amino acids, 10 to 20 amino acids, 11 to 20 amino acids, 12 to 20 amino acids, 15 to 20 amino acids, 1 to 15 amino acids, 5 to 15 amino acids, 6 to 15 amino acids, 7 to 15 amino acids, 8 to 15 amino acids, 9 to 15 amino acids, 10 to 15 amino acids, 11 to 15 amino acids, 12 to 15 amino acids, 1 to 12 amino acids, 5 to 12 amino acids, 6 to 12 amino acids, 7 to 12 amino acids, 8 to 12 amino acids, 9 to 12 amino acids, 10 to 12 amino acids, 1 to 10 amino acids, 5 to 10 amino acids, 6 to 10 amino acids, or 7 to 10 amino acids.

In embodiments, the cellular uptake moiety peptide is a transduction domain isolated from a known peptide sequence. Peptides with transduction domains are well known in the art and include, for example, human immunodeficiency virus (HIV) Trans-Activator of Transcription (TAT; described in Vives et al. *J Biol Chem.* 1997 Jun. 20; 272(25):16010-7), Herpes simplex virus tegument protein VP22, Atennapedia plasma membrane (ANT) translocation domain, a poly-Arg sequence, and the like. In embodiments, the cellular uptake moiety peptide is a continuous amino acid sequence from a known transduction domain. In other embodiments, the cellular uptake moiety peptide is two or more amino acid sequences from one or more known transduction domains that are not naturally present in a contiguous amino acid sequence, for example, a cellular uptake domain comprising two amino acid sequences would be separated by a third amino acid sequence in nature.

In embodiments, the cellular uptake moiety peptide is an optionally modified transduction domain from a known peptide. The modifications may be made using known techniques.

In embodiments, the cellular uptake moiety peptide is an optionally modified TAT translocation domain. The optionally modified TAT translocation domain can have 0 to 1 modifications, 0 to 2 modifications, 0 to 3 modifications, 0 to 4 modifications, 0 to 5 modifications, 0 to 6 modifications, 0 to 7 modifications, 0 to 8 modifications, 0 to 9 modifications, 1 to 2 modifications, 1 to 3 modifications, 1 to 4 modifications, 1 to 5 modifications, 1 to 6 modifications, 1 to 7 modifications, 1 to 8 modifications, 1 to 9 modifications, 2 to 3 modifications, 2 to 4 modifications, 2 to 5 modifications, 2 to 6 modifications, 2 to 7 modifications, 2 to 8 modifications, 2 to 9 modifications, 3 to 4 modifications, 3 to 5 modifications, 3 to 6 modifications, 3 to 7 modifications, 3 to 8 modifications, 3 to 9 modifications, 4 to 5 modifications, 4 to 6 modifications, 4 to 7 modifications, 4 to 8 modifications, or 4 to 9 modifications. In embodiments where the cellular uptake moiety peptide is a fragment of the TAT translocation domain, the cellular uptake moiety peptide sequence can have a minimum length of 5 amino acids, 6 amino acids, 7 amino acids, 8 amino acids, 9 amino acids, or 10 amino acids. In some embodiments where the cellular uptake moiety peptide is a fragment of the TAT translocation domain, the cellular uptake moiety peptide sequence can have a minimum of 5 contiguous amino acids, 6 contiguous amino acids, 7 contiguous amino acids, 8 contiguous amino acids, 9 contiguous amino acids, or 10 contiguous amino acids of a TAT translocation domain. Modified TAT translocation domains disclosed herein include amino acid sequences with at least 70% sequence identity, at least 75% sequence identity, at least 80% sequence identity, at least 85% sequence, at least 90% sequence identity, at least 95% sequence identity, at least 96% sequence identity, at least 97% sequence identity, at least 98% sequence identity, or at least 99% sequence identity to the sequence of YGRKKRRQRRR (SEQ ID NO:12). In some embodiments, the cellular uptake moiety is a modified TAT translocation domain. In other embodiments, the cellular uptake moiety peptide is a TAT translocation domain having the sequence SEQ ID NO:12.

In embodiments, the profiling peptide of the present disclosure comprises a TAT translocation domain and an Mcl-1 binding domain having a sequence of SEQ ID NOS: 1-11 with 0-8 modifications. In some embodiments, the profiling peptide of the present disclosure comprises a TAT translocation domain and an Mcl-1 binding domain having a sequence of SEQ ID NOS:1-11 with 1-8 modifications. In embodiments, the profiling peptide of the present disclosure comprises a TAT translocation domain and an Mcl-1 binding domain having SEQ ID NO:1 with 0-8 modifications. In some embodiments, the profiling peptide of the present disclosure comprises a TAT translocation domain and an Mcl-1 binding domain having any one of SEQ ID NOS:1-11. In some embodiments, the profiling peptide of the present disclosure comprises a TAT translocation domain having SEQ ID NO:12 and an Mcl-1 binding domain having any one of SEQ ID NOS:1-11 with 0-8 modifications. In some embodiments, the profiling peptide of the present disclosure comprises a TAT translocation domain having SEQ ID NO:12 and an Mcl-1 binding domain having any one of SEQ ID NOS:1-11 with 1-8 modifications. In embodiments, the profiling peptide of the present disclosure comprises a TAT translocation domain having SEQ ID NO:12 and an Mcl-1 binding domain having SEQ ID NO:1 with 0-8 modifications. In some embodiments, the profiling peptide of the present disclosure comprises a TAT translocation domain having SEQ ID NO:12 and an Mcl-1 binding domain having any one of SEQ ID NOS:1-11.

In embodiments, the cellular uptake moiety peptide is an optionally modified ANT translocation domain. The optionally modified ANT translocation domain can have 0 to 1 modifications, 0 to 2 modifications, 0 to 3 modifications, 0 to 4 modifications, 0 to 5 modifications, 0 to 6 modifications, 0 to 7 modifications, 0 to 8 modifications, 0 to 9 modifications, 1 to 2 modifications, 1 to 3 modifications, 1 to 4 modifications, 1 to 5 modifications, 1 to 6 modifications, 1 to 7 modifications, 1 to 8 modifications, 1 to 9 modifications, 2 to 3 modifications, 2 to 4 modifications, 2 to 5 modifications, 2 to 6 modifications, 2 to 7 modifications, 2 to 8 modifications, 2 to 9 modifications, 3 to 4 modifications, 3 to 5 modifications, 3 to 6 modifications, 3 to 7 modifications, 3 to 8 modifications, 3 to 9 modifications, 4 to 5 modifications, 4 to 6 modifications, 4 to 7 modifications, 4 to 8 modifications, or 4 to 9 modifications. In embodiments where the cellular uptake moiety peptide is a fragment of the ANT translocation domain, the cellular uptake moiety peptide sequence can have a minimum length of 5 amino acids, 6 amino acids, 7 amino acids, 8 amino acids, 9 amino acids, or 10 amino acids. In some embodiments where the cellular uptake moiety peptide is a fragment of the ANT translocation domain, the cellular uptake moiety peptide sequence can have a minimum of 5 contiguous amino acids, 6 contiguous amino acids, 7 contiguous amino acids, 8 contiguous amino acids, 9 contiguous amino acids, or 10 contiguous amino acids of an ANT translocation domain. Modified ANT translocation domains disclosed herein include amino acid sequences with at least 70% sequence identity, at least 75% sequence identity, at least 80% sequence identity, at least 85% sequence, at least 90% sequence identity, at least 95% sequence identity, at least 96% sequence identity, at least 97% sequence identity, at least 98% sequence identity, or at least 99% sequence identity to the sequence of RQIKIWFQNRRMKWKK (SEQ ID NO:13). In some embodiments, the cellular uptake moiety peptide is a modified ANT translocation domain. In other embodiments, the cellular uptake moiety peptide is an ANT translocation domain having the sequence SEQ ID NO:13.

In embodiments, the profiling peptide of the present disclosure comprises an ANT translocation domain and an Mcl-1 binding domain having any one of SEQ ID NOS:1-11 with 0-8 modifications. In some embodiments, the profiling peptide of the present disclosure comprises an ANT translocation domain and an Mcl-1 binding domain having any one of SEQ ID NOS:1-11 with 1-8 modifications. In embodiments, the profiling peptide of the present disclosure comprises an ANT translocation domain and an Mcl-1 binding domain having SEQ ID NO:1 with 0-8 modifications. In embodiments, the profiling peptide of the present disclosure comprises an ANT translocation domain and an Mcl-1 binding domain having any one of SEQ ID NOS:1-11. In some embodiments, the profiling peptide of the present disclosure comprises an ANT translocation domain having SEQ ID NO:13 and an Mcl-1 binding domain having any one of SEQ ID NOS:1-11 with 0-8 modifications. In some embodiments, the profiling peptide of the present disclosure comprises an ANT translocation domain having SEQ ID NO:13 and an Mcl-1 binding domain having any one of SEQ ID NOS:1-11 with 1-8 modifications. In embodiments, the profiling peptide of the present disclosure comprises an ANT translocation domain having SEQ ID NO:13 and an Mcl-1 binding domain having SEQ ID NO:1 with 0-8 modifications. In some embodiments, the profiling peptide of the present disclosure comprises an ANT translocation domain having SEQ ID NO:13 and an Mcl-1 binding domain having any one of SEQ ID NOS:1-11.

In embodiments, the cellular uptake moiety is an arginine rich amino acid sequence, such as a poly-Arg sequence. In some embodiments, the arginine rich amino acid sequence includes 3 to 9 Arg residues, 3 to 10 Arg residues, 3 to 11 Arg residues, 3 to 12 Arg residues, 4 to 9 Arg residues, 4 to 10 Arg residues, 4 to 11 Arg residues, 4 to 12 Arg residues, 5 to 9 Arg residues, 5 to 10 Arg residues, 5 to 11 Arg residues, 5 to 12 Arg residues, 6 to 9 Arg residues, 6 to 10 Arg residues, 6 to 11 Arg residues, 6 to 12 Arg residues, 7 to 9 Arg residues, 7 to 10 Arg residues, 7 to 11 Arg residues, 7 to 12 Arg residues, 8 to 9 Arg residues, 8 to 10 Arg residues, 8 to 11 Arg residues, 8 to 12 Arg residues, 9 to 10 Arg residues, 9 to 11 Arg residues, or 9 to 12 Arg residues. In some embodiments, the poly-Arg sequence includes 3 Arg residues, 4 Arg residues, 5 Arg residues, 6 Arg residues, 7 Arg residues, 8 Arg residues, 9 Arg residues, 10 Arg residues, 11 Arg residues, or 12 Arg residues. In some embodiments, the poly-Arg sequence includes 3 to 9 contiguous Arg residues, 3 to 10 contiguous Arg residues, 3 to 11 contiguous Arg residues, 3 to 12 contiguous Arg residues, 4 to 9 contiguous Arg residues, 4 to 10 contiguous Arg residues, 4 to 11 contiguous Arg residues, 4 to 12 contiguous Arg residues, 5 to 9 contiguous Arg residues, 5 to 10 contiguous Arg residues, 5 to 11 contiguous Arg residues, 5 to 12 contiguous Arg residues, 6 to 9 contiguous Arg residues, 6 to 10 contiguous Arg residues, 6 to 11 contiguous Arg residues, 6 to 12 contiguous Arg residues, 7 to 9 contiguous Arg residues, 7 to 10 contiguous Arg residues, 7 to 11 contiguous Arg residues, 7 to 12 contiguous Arg residues, 8 to 9 contiguous Arg residues, 8 to 10 contiguous Arg residues, 8 to 11 contiguous Arg residues, 8 to 12 contiguous Arg residues, 9 to 10 contiguous Arg residues, 9 to 11 contiguous Arg residues, or 9 to 12 contiguous Arg residues.

In embodiments, the profiling peptide of the present disclosure comprises an arginine rich amino sequence and an Mcl-1 binding domain having any one of SEQ ID NOS:1-11 with 0-8 modifications. In some embodiments, the profiling peptide of the present disclosure comprises an arginine rich amino sequence and an Mcl-1 binding domain having any one of SEQ ID NOS:1-11 with 1-8 modifications. In embodiments, the profiling peptide of the present disclosure comprises an arginine rich amino acid sequence and an Mcl-1 binding domain having SEQ ID NO:1 with 0-8 modifications. In embodiments, the profiling peptide of the present disclosure comprises an arginine rich amino sequence and an Mcl-1 binding domain having any one of SEQ ID NOS:1-11. In some embodiments, the profiling peptide of the present disclosure comprises a poly-Arg sequence having 3 to 10 contiguous Arg residues and an Mcl-1 binding domain having any one of SEQ ID NOS:1-11 with 0-8 modifications. In some embodiments, the profiling peptide of the present disclosure comprises a poly-Arg sequence having 3 to 10 contiguous Arg residues and an Mcl-1 binding domain having any one of SEQ ID NOS:1-11 with 1-8 modifications. In embodiments, the profiling peptide of the present disclosure comprises a poly-Arg sequence having 3 to 10 Arg residues and an Mcl-1 binding domain having SEQ ID NO:1 with 0-8 modifications. In some embodiments, the profiling peptide of the present disclosure comprises a poly-Arg sequence having 3 to 10 contiguous Arg residues and an Mcl-1 binding domain having any one of SEQ ID NOS:1-11.

In embodiments, a modified cellular uptake moiety peptide retains the ability of the unmodified sequence to cross the cell membrane when conjugated to a peptide (i.e., the modifications to the cellular uptake moiety peptide do not alter the ability to cross the cell membrane when conjugated to a peptide in a statistically significant, clinically significant, or biologically significant manner). In some embodiments, a modified cellular uptake moiety peptide retains the ability of the unmodified sequence to cross the cell membrane when conjugated to a peptide if the internalization efficiency of the modified cellular uptake moiety peptide is at least 70%, 80%, 85%, 90%, 95%, 97%, or 99% of the internalization efficiency of the unmodified sequence.

Alternatively, the cellular uptake moiety can be a chemical compound. Chemical compounds that facilitate cellular internalization are understood by one of skill in the art, and include, for example, cholesterol moieties, octanoic acid, lithocholic acid, oleyl alcohol, lithocholic acid oleylamide, and decanoic acid.

The Mcl-1 binding domain and the cellular uptake moiety can be linked by chemical coupling in any suitable manner known in the art. The cellular uptake moiety may be linked to the Mcl-1 binding domain at any suitable location, for example the N-terminus or the C-terminus of the Mcl-1 binding domain, either directly or via a linker. In embodiments, the cellular uptake moiety is conjugated to the Mcl-1 binding domain via a linker. In some embodiments, the cellular uptake moiety is conjugated to the N-terminus of the Mcl-1 binding domain. In further embodiments, the cellular uptake moiety is conjugated via a linker to the N-terminus of the Mcl-1 binding domain. In other embodiments, the cellular uptake moiety is conjugated to the C-terminus of the Mcl-1 binding domain. In still further embodiments, the cellular uptake moiety is conjugated via a linker to the C-terminus of the Mcl-1 binding domain.

Suitable linkers include peptide sequences of any length and other chemical linkers as would be understood by one of ordinary skill. Short peptide sequences are employed in certain embodiments, for example peptide sequences including uncharged amino acids, non-polar amino acids and/or small amino acids. In some embodiments, a linker is an amino acid sequence of 1-5 amino acids. For example some exemplary linkers include Gly, Pro, Ala, Val, Leu, Met, Ile, and/or Phe amino acids. Other examples of suitable peptide sequences include two Pro residues, three Gly residues, and the like. In some embodiments, the cellular uptake moiety is linked to the Mcl-1 binding domain in such a way that the cellular uptake moiety is cleaved upon or after entry into the cell. In certain embodiments, the linker comprises three Gly residues, for example GGG.

Embodiments of the profiling peptides of the present disclosure may be 20 to 40 amino acids in length, 20 to 45 amino acids in length, 20 to 50 amino acids in length, 25 to 40 amino acids in length, 25 to 45 amino acids in length, 25 to 50 amino acids in length, 30 to 36 amino acids in length, 30 to 37 amino acids in length, 30 to 38 amino acids in length, 30 to 39 amino acids in length, 30 to 40 amino acids in length, 30 to 45 amino acids in length, 30 to 50 amino acids in length, 31 to 36 amino acids in length, 31 to 37 amino acids in length, 31 to 38 amino acids in length, 31 to 39 amino acids in length, 31 to 40 amino acids in length, 32 to 36 amino acids in length, 32 to 37 amino acids in length, 32 to 38 amino acids in length, 32 to 39 amino acids in length, 32 to 40 amino acids in length, 33 to 36 amino acids in length, 33 to 37 amino acids in length, 33 to 38 amino acids in length, 33 to 39 amino acids in length, 33 to 40 amino acids in length, 34 to 36 amino acids in length, 34 to 37 amino acids in length, 34 to 38 amino acids in length, 34 to 39 amino acids in length, 34 to 40 amino acids in length, 35 to 36 amino acids in length, 35 to 37 amino acids in length, 35 to 38 amino acids in length, 35 to 39 amino acids in length, 35 to 40 amino acids in length, 35 to 45 amino acids in length, 35 to 50 amino acids in length, 36 to 37 amino acids in length, 36 to 38 amino acids in length, 36 to 39 amino acids in length, 36 to 40 amino acids in length, 37 to 38 amino acids in length, 37 to 39 amino acids in length, 37 to 40 amino acids in length, 38 to 39 amino acids in length, 38 to 40 amino acids in length, or 39 to 40 amino acids in length.

In embodiments, a profiling peptide comprises a cellular uptake moiety, and an Mcl-1 binding domain having any one of SEQ ID NOS:1-11 with 0-8 modifications. In embodiments, a profiling peptide comprises a cellular uptake moiety, and an Mcl-1 binding domain having any one of SEQ ID NOS:1-11 with 1-8 modifications. In embodiments, a profiling peptide comprises a cellular uptake moiety, and an Mcl-1 binding domain having SEQ ID NO:1 with 0-8 modifications. In embodiments, a profiling peptide comprises a cellular uptake moiety, and an Mcl-1 binding domain having any one of SEQ ID NOS:1-11. In some embodiments, a profiling peptide comprises a cellular uptake moiety, and an Mcl-1 binding domain having SEQ ID NO:1.

In embodiments, a profiling peptide comprises a cellular uptake moiety having SEQ ID NO:12 conjugated to an Mcl-1 binding domain having any one of SEQ ID NOS:1-11 with 0-8 modifications by a linker. In embodiments, a profiling peptide comprises a cellular uptake moiety having SEQ ID NO:12 conjugated to an Mcl-1 binding domain having any one of SEQ ID NOS:1-11 with 1-8 modifications by a linker. In embodiments, a profiling peptide comprises a cellular uptake moiety of SEQ ID NO:12 conjugated to an Mcl-1 binding domain having SEQ ID NO:1 with 0-8 modifications by a linker. In embodiments, a profiling peptide comprises a cellular uptake moiety having SEQ ID NO:12 conjugated to an Mcl-1 binding domain having any one of SEQ ID NOS:1-11 by a linker.

In certain embodiments, the profiling peptide has the sequence of YGRKKRRQRRRGGGRPEIWMTQGLRRL-GDEINAYYAR (SEQ ID NO:14). In other embodiments, the profiling peptide has the sequence of RPEIWMTQGL-RRLGDEINAYYARGGGYGRKKRRQRRR (SEQ ID NO:15).

Modified profiling peptides may be synthesized and purified by standard chemical methods. Peptides may be chemically synthesized by manual techniques or by automated procedures. Equipment for automated synthesis of peptides is commercially available from suppliers such as Perkin-Elmer, Inc. (Waltham, Mass.) and may be operated according to the manufacturer's instructions. Additionally, synthesized profiling peptides may be obtained from any number of different custom peptide synthesizing manufacturers. If required, synthesized peptides may be purified using preparative reverse phase chromatography, partition chromatography, gel filtration, gel electrophoresis, ion-exchange chromatography, or other methods used in the art.

Alternatively, modified profiling peptides may be readily prepared by genetic engineering and recombinant molecular biology methods and techniques. For example, polynucleotides encoding modified profiling peptides, or fragments thereof, may be constructed by recombinant methods or chemically synthesized (using such devices as an automatic synthesizer). Methods for purifying polynucleotides after either chemical synthesis or recombinant synthesis are known to persons skilled in the art. The constructed or synthesized polynucleotides may be incorporated into expression vectors (e.g., a plasmid, a viral particle, or a phage) for production of the profiling peptide in a host cell into which the expression vector has been introduced. Polynucleotides that encode a profiling peptide described herein may be recombinantly expressed in a variety of different host cells. Host cells may then be genetically engineered (transduced, transformed, or transfected) with the expression vectors. Selection and maintenance of culture conditions for particular host cells, such as temperature, pH and the like, will be readily apparent to the ordinarily skilled artisan. The produced peptides may then be harvested and purified using methods known in the art.

Compositions

Also disclosed herein are compositions comprising a profiling peptide as described herein and a carrier. Suitable carriers include those that maintain the stability and integrity of the profiling peptide. Carriers may be a diluent, excipient, preservative, or solvent.

In embodiments, more than one profiling peptide may be included in a composition. In such embodiments, at least two, three, four, five, six, seven, eight, nine, or ten profiling peptides are included.

In further embodiments, the compositions disclosed herein further comprise a detecting agent. The detecting agent can be any suitable agent, such as a fluorescent dye, a non-fluorescent dye (e.g., a non-fluorescent dye that can be converted to a fluorescent dye), an antibody, and the like. Fluorescent dyes include, for example, 5,5',6,6'-Tetrachloro-1,1',3,3'-tetraethyl-imidacarbocyanine iodide (JC-1), propidium iodide (PI), 1,1',3,3,3',3'-hexamethylindodicarbo-cyanine iodide (DilC1), and 3,3'-Dihexyloxacarbocyanine Iodide (DiOC$_6$). In various embodiments, the fluorescent dye is a potentiometric dye. "Potentiometric dyes" are dyes that change properties, for example, fluoresce, in response to voltage changes. Suitable potentiometric dyes include, for example, DilC1, JC-1, and rhodamine 123. In embodiments, the potentiometric dye included is JC-1 or rhodamine 123. In other embodiments, the dye is dihydrorhodamine 123, a non-fluorescent dye that can be converted via oxidation to rhodamine 123, a fluorescent dye.

In certain embodiments, the compositions described herein do not include a cell permeabilization agent, such as digitonin. A "cell permeabilization agent" is any reagent that breaks down the outer cell membrane, such that access is provided to the intracellular area, including the organelles. Two types of reagents are commonly used as cell permeabilization agents: (1) organic solvents, such as methanol and acetone, and (2) detergents such as a saponin, Triton X-100, and Tween-20. Generally, organic solvents permeabilize the outer cell membrane by dissolving lipids in the membranes leaving holes. Detergents generally create pores in the outer membrane, such as by interacting with and selectively removing membrane cholesterol.

In some embodiments, the compositions described herein further comprise a whole cell. In embodiments, the whole cell is a cancer cell. In certain embodiments, the cancer cell is from a human tumor-derived cell line. In certain embodiments, the cancer cell is a cancer stem cell. In some embodiments, the cancer cell is isolated from a tumor. In certain embodiments, the cancer cell is derived from the biopsy of a non-solid tumor. In embodiments, the cancer cell is obtained from peripheral blood from the subject. In other embodiments the cancer cell is obtained from bone marrow of the subject.

In specific embodiments, the cancer cell is derived from the biopsy of a subject with multiple myeloma, AML, acute lymphocytic leukemia, chronic lymphogenous leukemia, mantle cell lymphoma, diffuse large B-cell lymphoma, and non-Hodgkin's lymphoma. In some embodiments, the cancer cell is derived from a hematologic cancer, including, for example, multiple myeloma, myelodysplastic syndrome (MDS), AML, ALL, acute lymphocytic leukemia, chronic lymphogenous leukemia, CLL, mantle cell lymphoma, diffuse large B-cell lymphoma, follicular lymphoma, or non-Hodgkin's lymphoma. In certain embodiments, the cancer is AML.

In some embodiments, the cancer cell is derived from a solid tumor. In embodiments, the cancer cell is derived from the biopsy of a solid tumor, such as, for example, a biopsy of a colorectal, breast, prostate, lung, pancreatic, renal, or ovarian primary tumor. In various embodiments, the cancer cell is isolated from a pre-metastatic cancer, or a metastatic cancer.

Compositions of the present disclosure include a therapeutic composition for use in the treatment of cancer in a subject with a Mcl-1 dependency percentage of at least 15%, the Mcl-1 dependency percentage having been obtained by an in vitro method comprising: contacting a first portion of a plurality of cancer cells with a profiling peptide comprising a cellular uptake moiety and an Mcl-1 binding domain, the Mcl-1 binding domain having the sequence of SEQ ID NO:1 with 0-8 modifications, or a composition comprising a profiling peptide comprising a cellular uptake moiety and an Mcl-1 binding domain, the Mcl-1 binding domain having the sequence of SEQ ID NO:1 with 0-8 modifications and a carrier. Compositions of the present disclosure also include a therapeutic composition for cancer comprising a therapeutic agent, which is administered to a subject having a Mcl-1 dependency percentage of at least 15%, wherein, the Mcl-1 dependency percentage is obtained by an in vitro method comprising: contacting a first position of plurality of cancer cells with a profiling peptide comprising a cellular uptake moiety and an Mcl-1 binding domain, the Mcl-1 binding domain having the sequence of SEQ ID NO:1 with 0-8 modifications, or a composition comprising a profiling peptide comprising a cellular uptake moiety and an Mcl-1 binding domain, the Mcl-1 binding domain having the sequence of SEQ ID NO:1 with 0-8 modifications and a carrier.

Kits

The present disclosure further provides for kits comprising a profiling peptide as described herein, and a detecting agent. The detecting agent included in a kit of the disclosure can be any suitable agent, such as a fluorescent dye, a non-fluorescent dye that can be converted to a fluorescent dye, an antibody, and the like. Fluorescent dyes include, for example, 5,5',6,6'-Tetrachloro-1,1',3,3'-tetraethyl-imidacarbocyanine iodide (JC-1), propidium iodide (PI), 1,1',3,3,3',3'-hexamethylindodicarbo-cyanine iodide (DilC1), and 3,3'-Dihexyloxacarbocyanine Iodide ($DiOC_6$). In various embodiments, the fluorescent dye is a potentiometric dye. Suitable potentiometric dyes include, for example, DilC1, JC-1, and rhodamine 123. In embodiments, the potentiometric dye included is JC-1 or rhodamine 123. In other embodiments, the dye is dihydrorhodamine 123, a non-fluorescent dye that can be converted via oxidation to rhodamine 123, a fluorescent dye.

In embodiments, more than one profiling peptide may be included in a kit. In such embodiments, at least two, three, four, five, six, seven, eight, nine, or ten profiling peptides are included. In various embodiments in which more than one profiling peptide is provided, the sequencing of use and/or instructions for use of combinations of the profiling peptides can be included in the kit.

The kits can further comprise written instructions for using the kit in the methods disclosed herein. In various embodiments, the written instructions may include instructions regarding preparation of the profiling peptide and/or detecting agent; appropriate reference levels to interpret results associated with using the kit; proper disposal of the related waste; and the like. The written instructions can be in the form of printed instructions provided within the kit, or the written instructions can be printed on a portion of the container housing the kit. Written instructions may be in the form of a sheet, pamphlet, brochure, CD-Rom, or computer-readable device, or can provide directions to locate instructions at a remote location, such as a website. The written instructions may be in English and/or in a national or regional language.

Such kits can further comprise one or more reagents, assay controls, or other supplies necessary for evaluation of a sample, such as welled plates, syringes, ampules, vials, tubes, tubing, facemask, a needleless fluid transfer device, an injection cap, sponges, sterile adhesive strips, Chloraprep, gloves, and the like. In certain embodiments, the kits described herein do not include a cell permeabilization agent, such as digitonin. Variations in contents of any of the kits described herein can be made. In various embodiments, the profiling peptide and detecting agent, optionally with one or more reagents or supplies, are combined into a compact container, optionally with written instructions for use.

In some embodiments, a kit of the present disclosure comprises a detecting agent and a profiling peptide comprising a cellular uptake moiety and an Mcl-1 binding domain having any one of SEQ ID NOS:1-11 with 0-8 modifications. In some embodiments, a kit of the present disclosure comprises a detecting agent and a profiling peptide comprising a cellular uptake moiety and an Mcl-1 binding domain having any one of SEQ ID NOS:1-11 with 1-8 modifications. In some embodiments, a kit of the present disclosure comprises a detecting agent and a profiling peptide comprising a cellular uptake moiety, and an Mcl-1 binding domain having SEQ ID NO:1 with 0-8 modifications. In some embodiments, a kit of the present disclosure comprises a detecting agent and a profiling peptide comprising a cellular uptake moiety and an Mcl-1 binding domain having any one of SEQ ID NOS:1-11. In any of the above embodiments, the cellular uptake moiety may be a TAT translocation domain or an ANT translocation domain. In some embodiments, the cellular uptake moiety is conjugated to the Mcl-1 binding domain via a linker. In some embodiments, a kit of the present disclosure comprises a detecting agent and a profiling peptide with the sequence of (SEQ ID NO:14). In some embodiments, a kit of the present disclosure comprises a detecting agent and a profiling peptide with the sequence of (SEQ ID NO:15). In any of the above embodiments, the kit may not include a cell permeabilization agent. In any of the above embodiments, the detecting agent may be a potentiometric dye.

Methods of Use

Also described herein are methods of profiling a cancer cell from a subject. Some embodiments comprise contacting a cancer cell with a profiling peptide. The profiling peptide may be any of those known in the art (e.g., NOXA) or any of the profiling peptides disclosed herein. Such methods include methods of producing a sensitivity profile for a cancer cell or a plurality of cancer cells. In some embodiments, methods of producing a sensitivity profile for a cancer cell from a subject includes isolating a cancer cell or a plurality of cancer cells from a subject. In certain embodiments, the cancer cell is from a human tumor-derived cell line. In certain embodiments, the cancer cell is a cancer stem cell. In some embodiments, the cancer cell is isolated from a tumor. In certain embodiments, the cancer cell is derived from the biopsy of a non-solid tumor. In embodiments, the cancer cell is obtained from peripheral blood from the subject. In other embodiments the cancer cell is obtained from bone marrow of the subject.

In specific embodiments, the cancer cell is derived from the biopsy of a subject with multiple myeloma, AML, acute lymphocytic leukemia, chronic lymphogenous leukemia, mantle cell lymphoma, diffuse large B-cell lymphoma, and non-Hodgkin's lymphoma. In some embodiments, the cancer cell is derived from a hematologic cancer, including, for example, multiple myeloma, MDS, AML, ALL, acute lymphocytic leukemia, chronic lymphogenous leukemia, CLL, mantle cell lymphoma, diffuse large B-cell lymphoma, follicular lymphoma, or non-Hodgkin's lymphoma. In certain embodiments, the cancer is AML.

In some embodiments, the cancer cell is derived from a solid tumor. In embodiments, the cancer cell is derived from the biopsy of a solid tumor, such as, for example, a biopsy of a colorectal, breast, prostate, lung, pancreatic, renal, or ovarian primary tumor. In various embodiments, the cancer cell is isolated from a pre-metastatic cancer, or a metastatic cancer. In some embodiments, the cancer cell is a circulating tumor cell.

In a specific embodiment, the cancer cell is a multiple myeloma cell that is enriched by selection from a biopsy sample with an anti-CD138 antibody bound to a solid matrix or bead. In a specific embodiment, the cancer cell is an AML cell that is enriched by binding to a CD45-directed antibody. In a specific embodiment, the cancer cell is from a chronic lymphogenous leukemia or diffuse large B-cell lymphoma that is enriched by non-B cell depletion.

In various embodiments, the plurality of cancer cells is from a sample that has been frozen. In other embodiments, the plurality of cancer cells is from a sample that has not been frozen, i.e., that has been freshly collected.

Methods of profiling a cancer cell or a plurality of cancer cells may include contacting the plurality of cancer cells with one or more labels. In some embodiments that use flow cytometry, the labels are fluorophores attached to antibodies or a chemical entity with affinity for a cell membrane feature or other cellular structure. In other embodiments that use flow cytometry, the labels are quantum dots attached to antibodies or a chemical entity with affinity for a cell membrane feature or other cellular structure. In any of these embodiments, the antibodies or chemical entities may recognize any suitable cell surface marker, such as CD3, CD13, CD20, CD33, CD34, or CD45. In various embodiments, a combination of labels is used.

Methods of profiling the cancer cell from the subject may comprise contacting the cancer cell with one or more profiling peptides disclosed herein and detecting a change in mitochondrial integrity of the cancer cell. In various embodiments, at least two, three, four, five, six, seven, eight, or nine profiling peptides may be used at once. In such embodiments, a panel of profiling peptides may be screened on a single subject specimen.

A change in mitochondrial integrity can be detected in any suitable manner, such as, for example, a change in mitochondrial membrane potential, chromatin condensation, loss of viability, Cytochrome C translocation from the mitochondrial intermembrane space to the cytosol, swelling of the mitochondria, mitochondrial fission, morphological changes (e.g., cell shrinkage, membrane blebbing, etc.), phosphatidyl serine externalization (e.g., as measured by annexin V staining) or the increase in reactive oxygen intermediates. As is understood by one of skill in the art, various methods of detection for each of the indications of a change in mitochondrial integrity may be employed. For example, a change in mitochondrial membrane potential may be measured using potentiometric dyes, such as, for example, DilC1, JC-1, or rhodamine 123. In one embodiment, the potentiometric dye is JC-1 or rhodamine 123. In another example, Cytochrome C translocation can be measured using immunofluorescence staining. In a further example, an increase in reactive oxygen intermediates can be measured flow cytometric analysis after staining with carboxy-dichlorofluorescin diacetate.

In embodiments, the change in mitochondrial integrity will be a decrease in mitochondrial integrity. In some embodiments, the decrease in mitochondrial integrity is measured by a decrease in mitochondrial membrane potential. The decrease in mitochondrial potential may be determined using any suitable method known in the art, such as using a potentiometric dye. (e.g., JC-1 or rhodamine 123). In some embodiments, the decrease in mitochondrial integrity is measured by Cytochrome C leakage. In some embodiments, the decrease will be a statistically significant, clinically significant, or biologically significant decrease. In some embodiments, the decrease is a 2%, 5%, 10%, 15%, 20%, 25%, 30%, 35%, 40%, 45%, 50%, 60%, 70%, 80%, or 90% difference in a measurement of mitochondrial integrity, as described herein, as compared to a control.

In various embodiments, the plurality of cancer cells is divided into three portions for the purposes of profiling. In such embodiments, one portion may be treated with a negative control, one may be contacted with a positive control, and one may be contacted with one or more profiling peptides or a composition comprising one or more profiling peptides disclosed herein.

Any suitable positive control may be used. Examples of positive controls include Carbonyl cyanide-4-(trifluoromethoxy)phenylhydrazone (FCCP), Carbonyl cyanide m-chlorophenyl hydrazone (CCCP), N5,N6-bis(2-fluorophenyl)-[1,2,5]oxadiazolo[3,4-b]pyrazine-5,6-diamine (BAM-15), and the like. In particular embodiments, the positive control used is CCCP. Any suitable negative control may be used. Examples of negative controls include water and water soluble organic solvents, such as DMSO, ethanol, and methanol.

In some embodiments, the plurality of cancer cells are then contacted with a fluorescent dye, as described above. In particular embodiments, the dye is JC-1 or $DiOC_6$. In such embodiments, the plurality of cancer cells may then be analyzed using flow cytometry. Any suitable gating may be used in flow cytometry analysis. In some embodiments, such gating is CD45 dim, CD13, CD33, and CD34 high population. In other embodiments, such gating is the CD34 dim, CD3 and CD20 high population. Accordingly, embodiments of the present disclosure include a method of producing a sensitivity profile for a plurality of cancer cells from a subject, the method comprising: isolating the plurality of cancer cells from a sample, contacting the plurality of cancer cells with a label, treating a first portion of the plurality of cancer cells with a negative control, treating a second portion of the plurality of cancer cells with a positive control, treating a third portion of the plurality of cancer cells with a profiling peptide comprising a cellular uptake moiety and an Mcl-1 binding domain, the Mcl-1 binding domain having the sequence of SEQ ID NO:1 with 0-8 modifications, or a composition comprising a profiling peptide comprising a cellular uptake moiety and an Mcl-1 binding domain, the Mcl-1 binding domain having the sequence of SEQ ID NO:1 with 0-8 modifications and a carrier, contacting the first portion, the second portion, and the third portion of the plurality of cancer cells with a dye and analyzing the first portion, the second portion, and the third portion of the plurality of cancer cells by flow cytometry.

In some embodiments, an additive with a high affinity for calcium channels is added to the plurality of cancer cells. In some such embodiments, the additive is a diterpenoid. In particular embodiments, the additive is ryanodine. In embodiments, the additive is added in a concentration that is sufficient to significantly reduce or prevent nonspecific dye uptake. In some embodiments, the additive is added in a concentration of at least 20 nM. In some embodiments, the additive is added in a concentration of at least 30 nM.

Methods of the disclosure include isolating a plurality of cancer cells from a subject sample; the cells are then labeled; treated with a negative control, a positive control, or a profiling peptide of the disclosure; contacted with a dye; and analyzed with flow cytometry.

In an illustrative method of the disclosure, a plurality of cancer cells are isolated from a subject sample, and sample quality is confirmed. The cells are then pelleted, blocked in BSA, and labeled. After staining, cells are pelleted and separated into three portions and treated with either water or dimethyl sulfoxide (DMSO) (negative control), CCCP (positive control) or a profiling peptide of the disclosure (subject dependency). DiOC$_6$, a cationic mitochondrial dye is added. Later, the cells are analyzed via flow cytometry.

In some embodiments, a plurality of cancer cells are isolated from primary bone marrow aspirates and sample quality is determined. Cells are then pelleted, blocked in BSA and labeled for markers specific to B and T cells, as well as monocyte differentiation markers and blast-specific markers. After staining, cells are pelleted and separated into three portions and treated with either water (negative control), CCCP (positive control) or SEQ ID NO:14 (subject dependency). DiOC$_6$, a cationic mitochondrial dye is added. The cells are analyzed via flow cytometry. Blast cells are isolated by gating on the CD45 dim, CD13, CD33, and CD34 high population of each sample.

In particular embodiments, a plurality of cancer cells are isolated from primary bone marrow aspirates using density-gradient centrifugation. Sample quality is determined using trypan blue exclusion. Cells are then pelleted, blocked in BSA and labeled for markers specific to B and T cells, as well as monocyte differentiation markers and blast-specific markers. After staining, cells are pelleted and separated into fluorescent-activated cell sorting (FACS) tubes and treated with either water (negative control), CCCP (positive control) or SEQ ID NO:14 (subject dependency). DiOC$_6$, a cationic mitochondrial dye is added. The cells are then analyzed via flow cytometry. Blast cells are isolated by gating on the CD45 dim, CD13, CD33 and CD34 high population of each sample.

Some methods described herein further comprise determining an Mcl-1 dependency percentage for the first portion of the plurality of cancer cells based at least on the change in mitochondrial integrity.

In embodiments, the Mcl-1 dependency percentage (also referred to as Mcl-1 priming percentage; PP) is defined by the following equation:

$$PP = \left[1 - \left(\frac{Pep - PC}{NC - PC}\right)\right] * 100$$

Where PC is the AUC of the positive control, NC is the AUC of the negative control, and Pep is the AUC of the profiling peptide. Unless otherwise noted, the Mcl-1 dependency percentages calculated herein correspond to a profiling peptide concentration of 1 µM with CCCP as the positive control and water or DMSO as the negative control. The AUC is either area under the curve or signal intensity. In embodiments, the AUC is the median fluorescent intensity (MFI). In some embodiments, the area under the curve is established by homogenous time-resolved fluorescence (HTRF). In some embodiments, the time occurs over a window from between about 0 to about 300 min to about 0 to about 30 min. In some embodiments, the area under the curve is established by fluorescence activated cell sorting (FACS) or microplate assay as known in the art or described herein. In some embodiments, the signal intensity is a single time point measurement that occurs between about 5 min and about 300 min.

In embodiments where more than one profiling peptide is used, the Mcl-1 dependency percentage (PP) is defined by the following equation:

$$PP = \left[100 * \left(\frac{NC\ AUC - Pep_1\ AUC}{NC\ AUC - PC_{avg}\ AUC}\right)\right] Pep_1 + \left[100 * \left(\frac{NC\ AUC - Pep_2\ AUC}{NC\ AUC - PC_{avg}\ AUC}\right)\right] Pep_2 + \ldots \left[100 * \left(\frac{NC\ AUC - Pep_n\ AUC}{NC\ AUC - PC_{avg}\ AUC}\right)\right] Pep_n$$

In embodiments, a decrease in mitochondrial integrity indicates that the cancer cell is sensitive to a therapeutic agent. As used herein, "therapeutic agent" refers to any anti-cancer compound that is administered as a part of an anti-cancer therapy regimen. In embodiments, the therapeutic agent is a cyclin-dependent kinase 9 (CDK9) inhibitor. In some embodiments, the therapeutic agent is alvocidib.

In embodiments, methods of profiling a cancer cell from a subject include methods of predicting sensitivity of a cancer cell from a subject to a therapeutic agent. Therefore, methods of the present disclosure include a method of predicting sensitivity of a cancer cell from a subject to a therapeutic agent, comprising: contacting the cancer cell with a profiling peptide comprising a cellular uptake moiety, and an Mcl-1 binding domain having SEQ ID NO:1 with 0-8 modifications; and detecting a change in mitochondrial integrity of the cancer cell; wherein a decrease in mitochondrial integrity indicates that the cancer cell is sensitive to the therapeutic agent. In further embodiments, a method of predicting sensitivity of a cancer cell from a subject to a therapeutic agent, comprising: contacting the cancer cell with a profiling peptide comprising a cellular uptake moiety, and an Mcl-1 binding domain having SEQ ID NO:1 with 0-8 modifications; detecting a change in mitochondrial integrity of the cancer cell; and determining an Mcl-1 dependency percentage for the cancer cell based at least on the change in mitochondrial integrity, wherein an Mcl-1 dependency percentage above a predetermined value indicates that the cancer cell is sensitive to the therapeutic agent. In any of the above embodiments, the Mcl-1 binding domain has any one of SEQ ID NOS:1-11 with 0-8 modifications. In any of the above embodiments, the Mcl-1 binding domain has any one of SEQ ID NOS:1-11 with 1-8 modifications. In any of the above embodiments, the Mcl-1 binding domain has any one of SEQ ID NOS:1-11. In any of the above embodiments, the cellular uptake moiety may be a TAT translocation domain or an ANT translocation domain. In any of the above embodiments, the cellular uptake moiety is conjugated to the Mcl-1 binding domain via a linker. In any of the above embodiments, the profiling peptide has the sequence of (SEQ ID NO:14). In any of the above embodiments, the profiling peptide has the sequence of (SEQ ID NO:15). In any of the above embodiments, the cancer cell may not be permeabilized.

Further embodiments provide methods of predicting sensitivity of a cancer cell from a subject to a therapeutic agent, comprising: contacting the cancer cell with a profiling peptide comprising an Mcl-1 binding domain having SEQ ID NO:1 with 0-8 modifications, the cancer cell not being permeabilized; and detecting a change in mitochondrial integrity of the cancer cell; wherein a decrease in mitochondrial integrity indicates that the cancer cell is sensitive to the therapeutic agent. Still further embodiments provide a method of predicting sensitivity of a cancer cell from a subject to a therapeutic agent, comprising: contacting the cancer cell with a profiling peptide comprising an Mcl-1 binding domain having SEQ ID NO:1 with 0-8 modifications, the cancer cell not being permeabilized; detecting a change in mitochondrial integrity of the cancer cell; and determining an Mcl-1 dependency percentage for the cancer cell based at least on the change in mitochondrial integrity, wherein an Mcl-1 dependency percentage above a predetermined value indicates that the cancer cell is sensitive to the therapeutic agent. In any of the above embodiments, the Mcl-1 binding domain has any one of SEQ ID NOS: 1-11 with 0-8 modifications. In any of the above embodiments, the Mcl-1 binding domain has any one of SEQ ID NOS:1-11 with 1-8 modifications. In any of the above embodiments, the Mcl-1 binding domain has SEQ ID NO:1-11.

Further embodiments provide use of a profiling peptide comprising an Mcl-1 binding domain having SEQ ID NO:1 with 0-8 modifications. Accordingly, embodiments of the present disclosure include use of a profiling peptide comprising an Mcl-1 binding domain having SEQ ID NO:1 with 0-8 modifications in a method to predict a patient response to a therapeutic agent, the method comprising: contacting the cancer cell with a profiling peptide comprising a cellular uptake moiety, and an Mcl-1 binding domain having SEQ ID NO:1 with 0-8 modifications. In some embodiments, the method further comprises detecting a change in mitochondrial integrity of the cancer cell; wherein a decrease in mitochondrial integrity indicates that the cancer cell is sensitive to the therapeutic agent. In any of the above embodiments, the Mcl-1 binding domain has any one of SEQ ID NOS:1-11 with 0-8 modifications. In any of the above embodiments, the Mcl-1 binding domain has any one of SEQ ID NOS:1-11 with 1-8 modifications. In any of the above embodiments, the Mcl-1 binding domain has any one of SEQ ID NOS:1-11. In any of the above embodiments, the cellular uptake moiety may be a TAT translocation domain or an ANT translocation domain. In any of the above embodiments, the cellular uptake moiety is conjugated to the Mcl-1 binding domain via a linker. In any of the above embodiments, the profiling peptide has the sequence of (SEQ ID NO:14). In any of the above embodiments, the profiling peptide has the sequence of (SEQ ID NO:15). In any of the above embodiments, the cancer cell may not be permeabilized.

In embodiments, the Mcl-1 dependency percentage being over a predetermined value of 5%, 10%, 15%, 20%, 25%, 30%, 35%, 40%, 45%, 50%, 55%, 60%, 65%, 70%, or 75% indicates that the cancer cell is sensitive to the therapeutic agent, such as alvocidib, as a single agent, or combinations of alvocidib with other therapeutic agents, such as Ara-C, Mitoxantrone, Venetoclax, Daunorubicin, Brd4 inhibitors (e.g., JQ1), and/or DNA methyltransferase inhibitors (e.g., azacitidine or decitabine). In some embodiments, the Mcl-1 dependency percentage being over 15% indicates that the cancer cell is sensitive to the therapeutic agent, such as alvocidib, as a single agent, or combinations of alvocidib with other therapeutic agents. In some embodiments, the Mcl-1 dependency percentage being over 20% indicates that the cancer cell is sensitive to the therapeutic agent, as a single agent, or in combination with other therapeutic agents. In some embodiments, the Mcl-1 dependency percentage being over 25% indicates that the cancer cell is sensitive to the therapeutic agent, as a single agent, or in combination with other therapeutic agents. In some embodiments, the Mcl-1 dependency percentage being over 30% indicates that the cancer cell is sensitive to the therapeutic agent, as a single agent, or in combination with other therapeutic agents. In some embodiments, the Mcl-1 dependency percentage being over 35% indicates that the cancer cell is sensitive to the therapeutic agent, as a single agent, or in combination with other therapeutic agents. In some embodiments, the Mcl-1 dependency percentage being over 40% indicates that the cancer cell is sensitive to the therapeutic agent, as a single agent, or in combination with other therapeutic agents. In some embodiments, the Mcl-1 dependency percentage being over 45% indicates that the cancer cell is sensitive to the therapeutic agent, as a single agent, or in combination with other therapeutic agents. In some embodiments, the Mcl-1 dependency percentage being over 50% indicates that the cancer cell is sensitive to the therapeutic agent, as a single agent, or in combination with other therapeutic agents. In certain of the foregoing embodiments, the therapeutic agent is alvocidib.

In some embodiments, the methods of profiling a cancer described herein are useful in the evaluation of a subject, for example, for evaluating diagnosis, prognosis, and response to treatment. Diagnosis refers to the process of attempting to determine or identify a possible disease or disorder, such as, for example, cancer. Prognosis refers to predicting a likely outcome of a disease or disorder. A complete prognosis often includes the expected duration, the function, and a description of the course of the disease, such as progressive decline, intermittent crisis, or sudden, unpredictable crisis. Response to treatment is a prediction of a subject's medical outcome when receiving a treatment. Responses to treatment can be, by way of example, pathological complete response, survival, and progression free survival.

In embodiments, methods of profiling a cancer cell from a subject include methods of producing a sensitivity profile for a cancer cell from a subject. Therefore, methods of the disclosure further include a method of producing a sensitivity profile for a cancer cell from a subject, comprising: contacting the cancer cell with a profiling peptide comprising a cellular uptake moiety, and an Mcl-1 binding domain having SEQ ID NO:1 with 0-8 modifications; and detecting a change in mitochondrial integrity of the cancer cell. Additional methods of the disclosure include a method of producing a sensitivity profile for a cancer cell from a subject, comprising: contacting the cancer cell with a profiling peptide comprising a cellular uptake moiety, and an Mcl-1 binding domain having SEQ ID NO:1 with 0-8 modifications; detecting a change in mitochondrial integrity of the cancer cell; and determining an Mcl-1 dependency percentage for the cancer cell based at least on the change in mitochondrial integrity. In any of the above embodiments, the Mcl-1 binding domain has any one of SEQ ID NOS:1-11 with 0-8 modifications. In any of the above embodiments, the Mcl-1 binding domain has any one of SEQ ID NOS:1-11 with 1-8 modifications. In any of the above embodiments, the Mcl-1 binding domain has any one of SEQ ID NOS:1-11. In any of the above embodiments, the cellular uptake moiety may be a TAT translocation domain or an ANT translocation domain. In any of the above embodiments, the cellular uptake moiety is conjugated to the Mcl-1 binding domain via a linker. In any of the above embodiments, the profiling peptide has the sequence of (SEQ ID NO:14). In any of the above embodiments, the profiling peptide has the sequence of (SEQ ID NO:15). In any of the above embodiments, the cancer cell may not be permeabilized.

Further methods of the disclosure include a method of producing a sensitivity profile for a cancer cell from a subject, comprising: contacting the cancer cell with a profiling peptide comprising an Mcl-1 binding domain having SEQ ID NO:1 with 0-8 modifications, the cancer cell not being permeabilized; and detecting a change in mitochondrial integrity of the cancer cell. In further embodiments, methods of the disclosure include a method of producing a sensitivity profile for a cancer cell from a subject, comprising: contacting the cancer cell with a profiling peptide comprising an Mcl-1 binding domain having SEQ ID NO:1 with 0-8 modifications, the cancer cell not being permeabilized; detecting a change in mitochondrial integrity of the cancer cell; and determining an Mcl-1 dependency percentage for the cancer cell based at least on the change in mitochondrial integrity. In any of the above embodiments, the Mcl-1 binding domain has any one of SEQ ID NOS:1-11 with 0-8 modifications. In any of the above embodiments, the Mcl-1 binding domain has any one of SEQ ID NOS:1-11 with 1-8 modifications. In any of the above embodiments, the Mcl-1 binding domain has any one of SEQ ID NOS:1-11.

In various embodiments, the methods of profiling a cancer from a subject disclosed herein direct a clinical decision regarding whether a subject is to receive a specific treatment. In various embodiments, the present methods direct the treatment of a cancer subject, including, for example, what type of treatment should be administered or withheld. In various embodiments, a cancer treatment is administered or withheld based on the methods described herein. Examples of treatments include surgical resection, radiation therapy, chemotherapy, pharmacodynamic therapy, targeted therapy, immunotherapy, and supportive therapy (e.g., painkillers, diuretics, antidiuretics, antivirals, antibiotics, nutritional supplements, anemia therapeutics, blood clotting therapeutics, bone therapeutics, and psychiatric and psychological therapeutics). In various embodiments, the treatments include those described in US Patent Publication No. US 2012-0225851 and International Patent Publication No. WO 2012/122370.

In some embodiments, the present methods provide information about the likely response that a subject is to have to a particular treatment. In some embodiments, the present methods provide a high likelihood of response and may direct treatment, including aggressive treatment. In some embodiments, the present methods provide a low likelihood of response and may direct cessation of treatment, including aggressive treatment, and the use of palliative care, to avoid unnecessary toxicity from ineffective chemotherapies for a better quality of life.

In some embodiments, the present methods indicate a high or low likelihood of response to a pro-apoptotic agent and/or an agent that operates via apoptosis and/or an agent that operates via apoptosis driven by direct protein modulation. In various embodiments, exemplary pro-apoptotic agents and/or agents that operate via apoptosis and/or an agent that operates via apoptosis driven by direct protein modulation include ABT-263 (navitoclax), and obatoclax, WEP, bortezomib, and carfilzomib. In some embodiments, the present methods indicate a high or low likelihood of response to an agent that does not operate via apoptosis and/or an agent that does not operate via apoptosis driven by direct protein modulation. In various embodiments, exemplary agents that do not operate via apoptosis include kinesin spindle protein inhibitors, cyclin-dependent kinase inhibitors (e.g., alvocidib), Arsenic Trioxide (TRISENOX), MEK inhibitors, pomalidomide, azacitidine, decitibine, vorinostat, entinostat, dinaciclib, gemtuzumab, BTK inhibitors, PI3 kinase delta inhibitors, lenalidomide, anthracyclines, cytarabine, melphalam, Akt inhibitors, mTOR inhibitors. In a specific embodiment, the present methods are useful in predicting a subject's response to any of the treatments (including agents) described herein.

In embodiments, the present methods are predictive of a positive response to a pro-apoptotic agent or an agent that operates via apoptosis. In embodiments, the present methods are predictive of a positive response to an agent that does not operate via apoptosis. In further embodiments, the present methods are predictive of non-responsiveness to an apoptotic effector agent and/or an agent that does not operate via apoptosis.

In certain embodiments, the methods described herein predict a subject's response to a treatment regimen comprising one or more therapeutic agents. In some embodiments, the methods described herein direct the selection of a therapeutic agent for treating a cancer in a subject. In embodiments, the therapeutic agent is a cyclin-dependent kinase 9 (CDK9) inhibitor. In some embodiments, the CDK9 inhibitor is alvocidib.

In embodiments, the methods described herein predict a subject's response to a treatment regimen comprising a combination of two or more therapeutic agents. In some embodiments, the two or more therapeutic agents comprise a CDK9 inhibitor. In some embodiments, the two or more therapeutic agents comprise alvocidib. In some embodiments, the two or more therapeutic agents comprise alvocidib, cytarabine, mitoxantrone, daunorubicin, decitabine, azacitidine, venetoclax, bortezomib, dacogen, ibrutinib, lenalidomide, thalidomide, or a combination thereof. In some embodiments, the two or more therapeutic agents comprise alvocidib and cytarabine, mitoxantrone, daunorubicin, decitabine, azacitidine, venetoclax, bortezomib, dacogen, ibrutinib, lenalidomide, thalidomide, or a combination thereof.

In embodiments, methods of profiling a cancer cell from a subject include methods of selecting a therapeutic agent for treating a cancer in a subject. Therefore, methods of the disclosure further include a method of selecting a therapeutic agent for treating a cancer in a subject, comprising: contacting the cancer cell with a profiling peptide comprising a cellular uptake moiety, and an Mcl-1 binding domain having SEQ ID NO:1 with 0-8 modifications; detecting a change in mitochondrial integrity of the cancer cell; and selecting the therapeutic agent to treat the subject if the change in mitochondrial integrity is a decrease in mitochondrial integrity. Additional methods of the disclosure include a method of producing a sensitivity profile for a cancer cell from a subject, comprising: contacting the cancer cell with a profiling peptide comprising a cellular uptake moiety, and an Mcl-1 binding domain having SEQ ID NO:1 with 0-8 modifications; detecting a change in mitochondrial integrity of the cancer cell; determining an Mcl-1 dependency percentage for the cancer cell based at least on the change in mitochondrial integrity; and selecting the therapeutic agent to treat the subject if the Mcl-1 dependency percentage is above a predetermined value. In any of the above embodiments, the Mcl-1 binding domain has any one of SEQ ID NOS:1-11 with 0-8 modifications. In any of the above embodiments, the Mcl-1 binding domain has any one of SEQ ID NOS:1-11 with 1-8 modifications. In any of the above embodiments, the Mcl-1 binding domain has any one of SEQ ID NOS:1-11. In any of the above embodiments, the cellular uptake moiety may be a TAT translocation domain or an ANT translocation domain. In any of the above embodiments, the cellular uptake moiety is conjugated to the Mcl-1 binding domain via a linker. In any of the above embodiments, the profiling peptide has the sequence of (SEQ ID NO:14). In any of the above embodiments, the profiling peptide has the sequence of (SEQ ID NO:15). In any of the above embodiments, the cancer cell may not be permeabilized, for example with a cell permeabilization agent such as digitonin.

Further methods of the disclosure include a method of selecting a therapeutic agent for treating a cancer in a subject, comprising: receiving a sensitivity profile for a cancer cell of the subject, the sensitivity profile comprising mitochondrial integrity data of the cancer cell when contacted with a profiling peptide comprising a cellular uptake moiety, and an Mcl-1 binding domain having SEQ ID NO:1 with 0-8 modifications; and selecting the therapeutic agent to treat the subject if the mitochondrial integrity data shows a decrease in mitochondrial integrity. Yet further methods of the disclosure include a method of selecting a therapeutic agent for treating a cancer in a subject, comprising: receiving a sensitivity profile for a cancer cell of the subject, the sensitivity profile comprising Mcl-1 dependency data for the cancer cell, the Mcl-1 dependency data determined based at least on a change in mitochondrial integrity of the cancer cell when contacted with a profiling peptide comprising a cellular uptake moiety, and an Mcl-1 binding domain having SEQ ID NO:1 with 0-8 modifications; and selecting the therapeutic agent to treat the subject if the Mcl-1 dependency data shows an Mcl-1 dependency percentage above a predetermined value. In any of the above embodiments, the Mcl-1 binding domain has any one of SEQ ID NOS:1-11 with 0-8 modifications. In any of the above embodiments, the Mcl-1 binding domain has any one of SEQ ID NOS:1-11 with 1-8 modifications. In any of the above embodiments, the Mcl-1 binding domain has any one of SEQ ID NOS:1-11. In any of the above embodiments, the cellular uptake moiety may be a TAT translocation domain or an ANT translocation domain. In any of the above embodiments, the cellular uptake moiety is conjugated to the Mcl-1 binding domain via a linker. In any of the above embodiments, the profiling peptide has the sequence of (SEQ ID NO:14). In any of the above embodiments, the profiling peptide has the sequence of (SEQ ID NO:15). In any of the above embodiments, the cancer cell may not be permeabilized, for example with a cell permeabilization agent such as digitonin.

Still further methods of the disclosure include a method of selecting a therapeutic agent for treating a cancer in a subject, comprising: contacting the cancer cell with a profiling peptide comprising an Mcl-1 binding domain having SEQ ID NO:1 with 0-8 modifications, the cancer cell not being permeabilized; detecting a change in mitochondrial integrity of the cancer cell; and selecting the therapeutic agent to treat the subject if the change in mitochondrial integrity is a decrease in mitochondrial integrity. Yet further methods of the disclosure include a method of selecting a therapeutic agent for treating a cancer in a subject, comprising: contacting the cancer cell with a profiling peptide comprising an Mcl-1 binding domain having SEQ ID NO:1 with 0-8 modifications, the cancer cell not being permeabilized; detecting a change in mitochondrial integrity of the cancer cell; determining an Mcl-1 dependency percentage for the cancer cell based at least on the change in mitochondrial integrity; and selecting the therapeutic agent to treat the subject if the Mcl-1 dependency percentage is above a predetermined value. In any of the above embodiments, the Mcl-1 binding domain has any one of SEQ ID NOS:1-11 with 0-8 modifications. In any of the above embodiments, the Mcl-1 binding domain has any one of SEQ ID NOS:1-11 with 1-8 modifications. In any of the above embodiments, the Mcl-1 binding domain has SEQ ID NO:1-11.

In further embodiments, methods of the disclosure include a method of selecting a therapeutic agent for treating a cancer in a subject, comprising: receiving a sensitivity profile for a cancer cell of the subject, the sensitivity profile comprising mitochondrial integrity data of the cancer cell when contacted with a profiling peptide comprising an Mcl-1 binding domain having SEQ ID NO:1 with 0-8 modifications, the cancer cell not being permeabilized; and selecting the therapeutic agent to treat the subject if the mitochondrial integrity data shows a decrease in mitochondrial integrity. In additional embodiments, methods of the disclosure include a method of selecting a therapeutic agent for treating a cancer in a subject, comprising: receiving a sensitivity profile for a cancer cell of the subject, the sensitivity profile comprising Mcl-1 dependency data for the cancer cell, the Mcl-1 dependency data determined based at least on a change in mitochondrial integrity of the cancer cell when contacted with a profiling peptide comprising an Mcl-1 binding domain having SEQ ID NO:1 with 0-8 modifications, the cancer cell not being permeabilized; and selecting the therapeutic agent to treat the subject if the Mcl-1 dependency data shows an Mcl-1 dependency percentage above a predetermined value. In any of the above embodiments, the Mcl-1 binding domain has any one of SEQ ID NOS:1-11 with 0-8 modifications. In any of the above embodiments, the Mcl-1 binding domain has any one of SEQ ID NOS:1-11 with 1-8 modifications. In any of the above embodiments, the Mcl-1 binding domain has any one of SEQ ID NOS:1-11.

In embodiments, methods of the present disclosure include administering a therapeutic agent described herein to the subject based on mitochondrial integrity and/or Mcl-1 dependency data obtained by contacting a subject's cancer cell with any one or more of the profiling peptides disclosed herein. In one embodiment, the therapeutic agent is one or more of a BH3 mimetic, epigenetic modifying agent, topoisomerase inhibitor, cyclin-dependent kinase inhibitor (e.g., alvocidib), and/or kinesin-spindle protein stabilizing agent. In another embodiment, the therapeutic agent is a proteasome inhibitor; and/or a modulator of cell cycle regulation (by way of example, a cyclin dependent kinase inhibitor); and/or a modulator of cellular epigenetic mechanistic (by way of example, one or more of a histone deacetylase (HDAC) (e.g. one or more of vorinostat or entinostat), azacitidine, decitabine); and/or an anthracycline or anthracenedione (by way of example, one or more of epirubicin, doxorubicin, mitoxantrone, daunorubicin, idarubicin); and/ or a platinum-based therapeutic (by way of example, one or more of carboplatin, cisplatin, and oxaliplatin); cytarabine or a cytarabine-based chemotherapy; a BH3 mimetic (by way of example, one or more of BCL2, BCLXL, or MCL1); and an inhibitor of MCL1.

In various embodiments, the chemotherapeutic agent is selected from: one or more of alkylating agents such as thiotepa and CYTOXAN cyclosphosphamide; alkyl sulfonates such as busulfan, improsulfan and piposulfan; aziridines such as benzodopa, carboquone, meturedopa, and uredopa; ethylenimines and methylamelamines including altretamine, triethylenemelamine, trietylenephosphoramide, triethiylenethiophosphoramide and trimethylolomelamine; acetogenins (e.g., bullatacin and bullatacinone); a camptothecin (including the synthetic analogue topotecan); bryostatin; callystatin; CC-1065 (including its adozelesin, carzelesin and bizelesin synthetic analogues); cryptophycins (e.g., cryptophycin 1 and cryptophycin 8); dolastatin; duocarmycin (including the synthetic analogues, KW-2189 and CB 1-TM1); eleutherobin; pancratistatin; a sarcodictyin; spongistatin; nitrogen mustards such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, and ranimustine; antibiotics such as the enediyne antibiotics (e.g., calicheamicin, especially calicheamicin gammaII and calicheamicin omegaII (see, e.g., Agnew, Chem. Intl. Ed. Engl., 33: 183-186 (1994)); dynemicin, including dynemicin A; bisphosphonates, such as clodronate; an esperamicin; as well as neocarzinostatin chromophore and related chromoprotein enediyne antiobiotic chromophores), aclacinomysins, actinomycin, authramycin, azaserine, bleomycins, cactinomycin, carabicin, caminomycin, carzinophilin, chromomycinis, dactinomycin, daunorubicin, detorubicin, 6-diazo-5-oxo-L-norleucine, adriamycin doxorubicin (including morpholino-doxorubicin, cyanomorpholino-doxorubicin, 2-pyrrolino-doxorubicin and deoxy doxorubicin), epirubicin, esorubicin, idarubicin, marcellomycin, mitomycins such as mitomycin C, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine; androgens such as calusterone, dromostanolone propionate, epitiostanol, mepitiostane, testolactone; anti-adrenals such as minoglutethimide, mitotane, trilostane; folic acid replenisher such as folinic acid; aceglatone; aldophosphamide glycoside; aminolevulinic acid; eniluracil; amsacrine; bestrabucil; bisantrene; edatraxate; demecolcine; diaziquone; elformithine; elliptinium acetate; an epothilone; etoglucid; gallium nitrate; hydroxyurea; lentinan; lonidainine; maytansinoids such as maytansine and ansamitocins; mitoguazone; mitoxantrone; mopidanmol; nitraerine; pentostatin; phenamet; pirarubicin; losoxantrone; podophyllinic acid; 2-ethylhydrazide; procarbazine; PSK polysaccharide complex (JHS Natural Products, Eugene, Oreg.); razoxane; rhizoxin; sizofuran; spirogermanium; tenuazonic acid; triaziquone; 2,2',2''-trichlorotriethyl amine; trichothecenes (e.g., T-2 toxin, verracurin A, roridin A and anguidine); urethan; vindesine; dacarbazine; mannomustine; mitobronitol; mitolactol; pipobroman; gacytosine; arabinoside ("Ara-C"); cyclophosphamide; thiotepa; taxoids, e.g., TAXOL paclitaxel (Bristol-Myers Squibb Oncology, Princeton, N.J.), ABRAXANE Cremophor-free, albumin-engineered nanoparticle formulation of paclitaxel (American Pharmaceutical Partners, Schaumberg, 111.), and TAXOTERE doxetaxel (Rhone-Poulenc Rorer, Antony, France); chlorambucil; GEMZAR gemcitabine; 6-thioguanine; mercaptopurine; methotrexate; platinum analogs such as cisplatin, oxaliplatin and carboplatin; vinblastine; platinum; etoposide (VP-16); ifosfamide; mitoxantrone; vincristine; NAVELBINE. vinorelbine; novantrone; teniposide; edatrexate; daunomycin; aminopterin; xeloda; ibandronate; irinotecan (Camptosar, CPT-11) (including the treatment regimen of irinotecan with 5-FU and leucovorin); topoisomerase inhibitor RFS 2000; difluoromethylornithine (DMFO); retinoids such as retinoic acid; capecitabine; combretastatin; leucovorin (LV); oxaliplatin, including the oxaliplatin treatment regimen (FOLFOX); lapatinib (Tykerb); inhibitors of PKC-1, Raf, H-Ras, EGFR (e.g., erlotinib (Tarceva)) and VEGF-A that reduce cell proliferation, dacogen, velcade, and pharmaceutically acceptable salts, acids or derivatives of any of the agents listed herein. Exemplary therapeutic agents include alvocidib, cytarabine, mitoxantrone, daunorubicin, decitabine, azacitidine, venetoclax, bortezomib, dacogen, ibrutinib, lenalidomide, thalidomide, and pharmaceutically acceptable salts, acids or derivatives thereof.

Suitable methods may include administration of a pro-apoptotic agent and/or an agent that operates via apoptosis and/or an agent that operates via apoptosis driven by direct protein modulation. Examples of such agents include ABT-263 (Navitoclax), and obatoclax, WEP, bortezomib, and carfilzomib. Other suitable treatments may include an agent that does not operate via apoptosis and/or an agent that does not operate via apoptosis driven by direct protein modulation. Examples of such agents include kinesin spindle protein inhibitors, cyclin-dependent kinase (CDK) inhibitors, Arsenic Trioxide (TRISENOX), MEK inhibitors, pomalidomide, azacitidine, decitibine, vorinostat, entinostat, dinaciclib, gemtuzumab, BTK inhibitors, PI3 kinase delta inhibitors, lenalidomide, anthracyclines, cytarabine, melphalan, Akt inhibitors, mTOR inhibitors. In embodiments, the CDK inhibitor is a CDK9 inhibitor. In some embodiments, the CDK9 inhibitor is alvocidib.

In embodiments, the methods of treatment disclosed herein comprise administering an effective amount of a therapeutic agent to the subject, thereby treating their cancer. In various embodiments, effective amounts of a therapeutic agent can decrease the number of tumor cells, decrease the number of metastases, decrease tumor volume, induce apoptosis of cancer cells, induce cancer cell death, induce—or radio-sensitivity in cancer cells, inhibit angiogenesis near cancer cells, inhibit cancer cell proliferation, inhibit tumor growth, prevent metastasis, reduce the number of metastases, increase life expectancy, prolong a subject's life, reduce cancer-associated pain, and/or reduce relapse or re-occurrence of the cancer following treatment.

For administration, effective amounts (also referred to as doses) can be initially estimated based on results from in vitro assays and/or animal model studies. For example, a dose can be formulated in animal models to achieve a circulating concentration range that includes an IC50 as determined in cell culture against a particular target. Such information can be used to more accurately determine useful doses in subjects of interest.

The actual dose amount administered to a particular subject can be determined by a physician, veterinarian, or researcher taking into account parameters such as physical and physiological factors including target, body weight, severity of condition, type of cancer, previous or concurrent therapeutic interventions, idiopathy of the subject, and route of administration.

In embodiments, methods of profiling a cancer cell from a subject include methods of treating a cancer in a subject in need thereof. Accordingly, methods of the present disclosure include a method for treating a cancer in a subject in need thereof, the method comprising administering a treatment regimen comprising a therapeutic agent to a subject having an Mcl-1 dependency percentage above a predetermined value, the Mcl-1 dependency percentage having been obtained by an in vitro method comprising contacting a first portion of a plurality of cancer cells with a profiling peptide comprising a cellular uptake moiety and an Mcl-1 binding domain, the Mcl-1 binding domain having the sequence of SEQ ID NO:1 with 0-8 modifications, or a composition comprising a profiling peptide comprising a cellular uptake moiety and an Mcl-1 binding domain, the Mcl-1 binding domain having the sequence of SEQ ID NO:1 with 0-8 modifications and a carrier. Additionally, methods of the present disclosure include a method of treating a cancer in a subject in need thereof, comprising: contacting a cancer cell from the subject with a profiling peptide comprising a cellular uptake moiety, and an Mcl-1 binding domain having SEQ ID NO:1 with 0-8 modifications; detecting a change in mitochondrial integrity of the cancer cell; and administering an effective amount of a therapeutic agent to the subject if a decrease in mitochondrial integrity is detected, thereby treating the cancer in the subject. Further methods of the present disclosure include a method of treating a cancer in a subject in need thereof, comprising: contacting a cancer cell from the subject with a profiling peptide comprising a cellular uptake moiety, and an Mcl-1 binding domain having SEQ ID NO:1 with 0-8 modifications; detecting a change in mitochondrial integrity of the cancer cell; determining an Mcl-1 dependency percentage for the cancer cell based at least on the change in mitochondrial integrity; and administering an effective amount of a therapeutic agent to the subject if the Mcl-1 dependency percentage is above a predetermined value, thereby treating the cancer in the subject. In any of the above embodiments, the Mcl-1 binding domain has any one of SEQ ID NOS:1-11 with 0-8 modifications. In any of the above embodiments, the Mcl-1 binding domain has any one of SEQ ID NOS:1-11 with 1-8 modifications. In any of the above embodiments, the Mcl-1 binding domain has any one of SEQ ID NOS:1-11. In any of the above embodiments, the cellular uptake moiety may be a TAT translocation domain or an ANT translocation domain. In any of the above embodiments, the cellular uptake moiety is conjugated to the Mcl-1 binding domain via a linker. In any of the above embodiments, the profiling peptide has the sequence of (SEQ ID NO:14). In any of the above embodiments, the profiling peptide has the sequence of (SEQ ID NO:15). In any of the above embodiments, the cancer cell may not be permeabilized.

In some embodiments, methods of the present disclosure include a method of treating a cancer in a subject in need thereof, comprising: receiving a sensitivity profile for a cancer cell of the subject, the sensitivity profile comprising mitochondrial integrity data of the cancer cell when contacted with a profiling peptide comprising a cellular uptake moiety, and an Mcl-1 binding domain having SEQ ID NO:1 with 0-8 modifications; and administering an effective amount of a therapeutic agent to the subject if the mitochondrial integrity data shows a decrease in mitochondrial integrity, thereby treating the cancer in the subject. In further embodiments, methods of the present disclosure include a method of treating a cancer in a subject in need thereof, comprising: receiving a sensitivity profile for a cancer cell of the subject, the sensitivity profile comprising Mcl-1 dependency data for the cancer cell, the Mcl-1 dependency data being determined based at least on a change in mitochondrial integrity of the cancer cell when contacted with a profiling peptide comprising a cellular uptake moiety, and an Mcl-1 binding domain having SEQ ID NO:1 with 0-8 modifications; and administering an effective amount of a therapeutic agent to the subject if the Mcl-1 dependency data shows an Mcl-1 dependency percentage above a predetermined value, thereby treating the cancer in the subject. In any of the above embodiments, the Mcl-1 binding domain has any one of SEQ ID NOS:1-11 with 0-8 modifications. In any of the above embodiments, the Mcl-1 binding domain has any one of SEQ ID NOS:1-11 with 1-8 modifications. In any of the above embodiments, the Mcl-1 binding domain has any one of SEQ ID NOS:1-11. In any of the above embodiments, the cellular uptake moiety may be a TAT translocation domain or an ANT translocation domain. In any of the above embodiments, the cellular uptake moiety is conjugated to the Mcl-1 binding domain via a linker. In any of the above embodiments, the profiling peptide has the sequence of (SEQ ID NO:14). In any of the above embodiments, the profiling peptide has the sequence of (SEQ ID NO:15). In any of the above embodiments, the cancer cell may not be permeabilized.

Further embodiments of the present disclosure include a method of treating a cancer in a subject in need thereof, comprising: contacting a cancer cell from the subject with a profiling peptide comprising an Mcl-1 binding domain having SEQ ID NO:1 with 0-8 modifications, the cancer cell not being permeabilized; detecting a change in mitochondrial integrity of the cancer cell; and administering an effective amount of a therapeutic agent to the subject if a decrease in mitochondrial integrity is detected, thereby treating the cancer in the subject. In still further embodiments, methods of the present disclosure include a method of treating a cancer in a subject in need thereof, comprising: contacting a cancer cell from the subject with a profiling peptide comprising an Mcl-1 binding domain having SEQ ID NO:1 with 0-8 modifications, the cancer cell not being permeabilized; detecting a change in mitochondrial integrity of the cancer cell; determining an Mcl-1 dependency percentage for the cancer cell based at least on the change in mitochondrial integrity; and administering an effective amount of a therapeutic agent to the subject if the Mcl-1 dependency percentage is above a predetermined value, thereby treating the cancer in the subject. In any of the above embodiments, the Mcl-1 binding domain has any one of SEQ ID NOS:1-11 with 0-8 modifications. In any of the above embodiments, the Mcl-1 binding domain has any one of SEQ ID NOS:1-11 with 1-8 modifications. In any of the above embodiments, the Mcl-1 binding domain has any one of SEQ ID NOS:1-11.

Additional embodiments of the present disclosure include a method of treating a cancer in a subject in need thereof, comprising: receiving a sensitivity profile for a cancer cell of the subject, the sensitivity profile comprising mitochondrial integrity data of the cancer cell when contacted with a profiling peptide comprising an Mcl-1 binding domain having SEQ ID NO:1 with 0-8 modifications, the cancer cell not being permeabilized; and administering an effective amount of a therapeutic agent to the subject if the mitochondrial integrity data shows a decrease in mitochondrial integrity, thereby treating the cancer in the subject. In some embodiments, methods of the present disclosure include a method of treating a cancer in a subject in need thereof, comprising: receiving a sensitivity profile for cancer cells of the subject, the sensitivity profile comprising Mcl-1 dependency data for the cancer cell, the Mcl-1 dependency data being determined based at least on a change in mitochondrial integrity of the cancer cell when contacted with a profiling peptide comprising an Mcl-1 binding domain having SEQ ID NO:1 with 0-8 modifications, the cancer cell not being permeabilized; and administering an effective amount of a therapeutic agent to the subject if the Mcl-1 dependency data shows an Mcl-1 dependency percentage above a predetermined value, thereby treating the cancer in the subject. In any of the above embodiments, the Mcl-1 binding domain has any one of SEQ ID NOS:1-11 with 0-8 modifications. In any of the above embodiments, the Mcl-1 binding domain has any one of SEQ ID NOS:1-11 with 1-8 modifications. In any of the above embodiments, the Mcl-1 binding domain has any one of SEQ ID NOS:1-11.

In any of the above embodiments, an effective amount of one or more of the following therapeutic agents may be administered to the subject: (i) a CDK inhibitor (e.g. a CDK4 inhibitor, a CDK6 inhibitor, a CDK7 inhibitor, a CDK8 inhibitor, a CDK9 inhibitor, a CDK10 inhibitor, and/or a CDK11 inhibitor); (ii) a bromodomain inhibitor (e.g., a Brd2 inhibitor, a Brd3 inhibitor, a Brd4 inhibitor and/or a BrdT inhibitor); (iii) a histone methyltransferase inhibitor (e.g., a DOT1-like histone methyltransferase (Dot1L) inhibitor); (iv) a histone deacetylase (HDAC) inhibitor (e.g., a Class I HDAC (e.g., HDAC1, HDAC2, HDAC3 and HDAC8) inhibitor, a Class IIa HDAC (e.g., HDAC4, HDAC5, HDAC7, and HDAC9) inhibitor; a Class IIb HDAC (e.g., HDAC6 and HDAC10) inhibitor; and a Class IV HDAC (e.g., HDAC11) inhibitor); and (v) a histone demethylase inhibitor (e.g. an inhibitor of a lysine-specific demethylase, such as lysine-specific demethylase 1A (Lsd1)).

In some embodiments, the CDK inhibitor is a CDK7, CDK9 inhibitor, or both. In some embodiments, the CDK inhibitor is a CDK9-specific siRNA, alvocidib, or dinaciclib. In some embodiments, the bromodomain inhibitor is a Brd4 inhibitor. In some embodiments, the bromodomain inhibitor is JQ-1 (Nature 2010 Dec. 23; 468(7327):1067-73), BI2536 (ACS Chem. Biol. 2014 May 16; 9(5):1160-71; Boehringer Ingelheim), TG101209 (ACS Chem. Biol. 2014 May 16; 9(5):1160-71), OTX015 (Mol. Cancer Ther. November 201312; C244; Oncoethix), IBET762 (J Med Chem. 2013 Oct. 10; 56(19):7498-500; GlaxoSmithKline), IBET151 (Bioorg. Med. Chem. Lett. 2012 Apr. 15; 22(8):2968-72; GlaxoSmithKline), PFI-1 (J. Med. Chem. 2012 Nov. 26; 55(22):9831-7; Cancer Res. 2013 Jun. 1; 73(11):3336-46; Structural Genomics Consortium), or CPI-0610 (Constellation Pharmaceuticals). In some embodiments, the histone methyltransferase inhibitor is EPZ004777, EPZ-5676 (Blood. 2013 Aug. 8; 122(6):1017-25) or SGC0946 (Nat. Commun. 2012; 3:1288). In specific embodiments, the histone methyltransferase inhibitor is EPZ-5676. In some embodiments, the HDAC inhibitor is trichostatin A, vorinostat (Proc. Natl. Acad. Sci. U.S.A. 1998 Mar. 17; 95(6): 3003-7), givinostat, abexinostat (Mol. Cancer Ther. 2006 May; 5(5):1309-17), belinostat (Mol. Cancer Ther. 2003 August; 2(8):721-8), panobinostat (Clin. Cancer Res. 2006 Aug. 1; 12(15):4628-35), resminostat (Clin. Cancer Res. 2013 Oct. 1; 19(19):5494-504), quisinostat (Clin. Cancer Res. 2013 Aug. 1; 19(15):4262-72), depsipeptide (Blood. 2001 Nov. 1; 98(9):2865-8), entinostat (Proc. Natl. Acad. Sci. U.S.A. 1999 Apr. 13; 96(8):4592-7), mocetinostat (Bioorg. Med. Chem. Lett. 2008 Feb. 1; 18(3):1067-71) or valproic acid (EMBO J. 2001 Dec. 17; 20(24):6969-78). For example, in some embodiments, the HDAC inhibitor is panobinostat. In some embodiments, the histone demethylase inhibitor is HCl-2509 (BMC Cancer. 2014 Oct. 9; 14:752), tranylcypromine or ORY-1001 (J. Clin. Oncol 31, 2013 (suppl; abstr e13543).

In embodiments, an effective amount of two or more of the following therapeutic agents may be administered to the subject: (i) a cyclin-dependent kinase inhibitor; (ii) a bromodomain inhibitor; (iii) a histone methyltransferase inhibitor; (iv) a histone deacetylase inhibitor; and (v) a histone demethylase inhibitor.

In some embodiments, the two or more therapeutic agents are a CDK inhibitor, and a bromodomain inhibitor. In some embodiments, the CDK inhibitor is alvocidib or a CDK9-specific siRNA. In particular embodiments, the CDK inhibitor is alvocidib. In some embodiments, the CDK inhibitor is alvocidib or dinaciclib, and the bromodomain inhibitor is JQ1, IBET762, or OTX015. In certain embodiments, the bromodomain inhibitor is JQ1. In certain embodiments, the bromodomain inhibitor is IBET762. In certain embodiments, the bromodomain inhibitor is OTX015. In some embodiments, the two or more therapeutic agents are alvocidib and JQ1. In some embodiments, the two or more therapeutic agents are alvocidib and IBET762. In some embodiments, the two or more therapeutic agents are alvocidib and OTX015.

In some embodiments, the therapeutic agent is a CDK inhibitor, and an effective amount of a histone deacetylase inhibitor is also administered to the subject. In some embodiments, the CDK inhibitor is alvocidib. In some embodiments, the histone deacetylase inhibitor is panobinostat. In some embodiments, the CDK inhibitor is alvocidib or dinaciclib, and the histone deacetylase inhibitor is panobinostat. In certain embodiments, the CDK inhibitor is alvocidib, and the histone deacetylase inhibitor is panobinostat.

In any of the above embodiments, the therapeutic agent is a CDK inhibitor, and an effective amount of a DNA methyltransferase inhibitor is further administered to the subject. In such embodiments, the CDK inhibitor can be alvocidib or dinaciclib and the DNA methyltransferase can be a nucleoside analogue. In some embodiments, the CDK inhibitor can be alvocidib or dinaciclib and the DNA methyltransferase can be azacitidine or decitabine.

In any of the above embodiments, the therapeutic agent is a CDK9 inhibitor. In such embodiments, the CDK9 inhibitor may be alvocidib. In any of the above embodiments, the therapeutic agent is alvocidib, and an effective amount of Ara-C and mitoxantrone are further administered to the subject. In another embodiment, the therapeutic agent is alvocidib, and an effective amount of a Bcl-2 inhibitor, such as Venetoclax, is further administered to the subject. In a specific embodiment, the therapeutic agent is alvocidib, and the Bcl-2 inhibitor is Venetoclax. In other of the above embodiments, the therapeutic agent is alvocidib, and an effective amount of Ara-C and Daunorubicin is further administered to the subject. In other of the above embodiments, the therapeutic agent is alvocidib, and an effective amount of a Brd4 inhibitor, such as JQ1, is further administered to the subject. In other of the above embodiments, the therapeutic agent is alvocidib, and an effective amount of a DNA methyltransferase inhibitor, such as azacitidine or decitabine, is further administered to the subject. In further of the above embodiments, the therapeutic agent is alvocidib, and an effective amount of a DNA methyltransferase inhibitor, such as azacitidine or decitabine, and a Brd4 inhibitor, such as JQ1, is further administered to the subject.

In any of the above embodiments, the CDK9 inhibitor is dinaciclib.

In any of the above embodiments, the therapeutic agent is Venetoclax. In any of the above embodiments, the therapeutic agent is Ara-C. In any of the above embodiments, the therapeutic agent is Ara-C, and an effective amount of Daunorubicin is further administered.

In any of the above embodiments, a combination of two or more therapeutic agents is administered to a subject. In some embodiments, the two or more therapeutic agents comprise a CDK9 inhibitor. In some embodiments, the two or more therapeutic agents comprise alvocidib. In some embodiments, the two or more therapeutic agents comprise alvocidib, cytarabine, mitoxantrone, daunorubicin, decitabine, azacitidine, venetoclax, bortezomib, dacogen, ibrutinib, lenalidomide, thalidomide, or a combination thereof. In some embodiments, the two or more therapeutic agents comprise alvocidib and cytarabine, mitoxantrone, daunorubicin, decitabine, azacitidine, venetoclax, bortezomib, dacogen, ibrutinib, lenalidomide, thalidomide, or a combination thereof.

In more embodiments of the foregoing, the cancer cell specimen is derived from the biopsy of a solid tumor. In still more embodiments of the foregoing, the cancer cell specimen is derived from the biopsy of a non-solid tumor. In any of the foregoing treatment methods, the cancer is a hematologic cancer. For example, in some embodiments the hematologic cancer the hematologic cancer is multiple myeloma, MDS, AML, ALL, acute lymphocytic leukemia, chronic lymphogenous leukemia, CLL, mantle cell lymphoma, diffuse large B-cell lymphoma, follicular lymphoma, or non-Hodgkin's lymphoma. In some specific embodiments, the hematological cancer is AML. In some other embodiments of the foregoing, the hematologic cancer is MDS. In different embodiments of the foregoing, the hematologic cancer is CLL.

In any of the above embodiments, the cancer cell profiled may not be permeabilized, for example with a cell permeabilization agent such as digitonin.

In any of the above embodiments, an additional treatment agent can be selected and optionally administered. Examples of such agents include one or more of anti-cancer drugs, therapy, surgery, adjuvant therapy, and neoadjuvant therapy, such as those specific agents described herein.

In one embodiment, the present methods further direct a clinical decision regarding whether a subject is to receive adjuvant therapy after primary, main, or initial treatment, including a single sole adjuvant therapy. Adjuvant therapy, also called adjuvant care, is treatment that is given in addition to the primary, main or initial treatment. By way of example, adjuvant therapy may be an additional treatment usually given after surgery where all detectable disease has been removed, but where there remains a statistical risk of relapse due to occult disease.

In some embodiments, the present methods direct a subject's treatment to include adjuvant therapy. For example, a subject that is scored to be responsive to a specific treatment may receive such treatment as adjuvant therapy. Further, the present methods may direct the identity of an adjuvant therapy, by way of example, as a treatment that induces and/or operates in a pro-apoptotic manner or one that does not. In one embodiment, the present methods may indicate that a subject will not be or will be less responsive to a specific treatment and therefore such a subject may not receive such treatment as adjuvant therapy. Accordingly, in some embodiments, the present methods provide for providing or withholding adjuvant therapy according to a subject's likely response. In this way, a subject's quality of life, and the cost of care, may be improved.

In any of the above embodiments, the methods further comprise evaluating a clinical factor. In various embodiments, the clinical factor is one or more of age, cytogenetic status, performance, histological subclass, gender, and disease stage. In embodiments, the clinical factor is age. In such embodiments, the subject age profile is classified as over about 10, over about 20, over about 30, over about 40, over about 50, over about 60, over about 70, over about 80 years old.

In some embodiments, the clinical factor is cytogenetic status. Cytogenetic status can be measured in a variety of manners known in the art. For example, FISH, traditional karyotyping, and virtual karyotyping (e.g. comparative genomic hybridization arrays, CGH and single nucleotide polymorphism arrays) may be used. For example, FISH may be used to assess chromosome rearrangement at specific loci and these phenomena are associated with disease risk status. In some embodiments, the cytogenetic status is favorable, intermediate, or unfavorable.

In some embodiments, the clinical factor is performance. Performance status can be quantified using any system and methods for scoring a subject's performance status are known in the art. The measure is often used to determine whether a subject can receive therapy, adjustment of dose adjustment, and to determine intensity of palliative care. There are various scoring systems, including the Karnofsky score and the Zubrod score. Parallel scoring systems include the Global Assessment of Functioning (GAF) score, which has been incorporated as the fifth axis of the Diagnostic and Statistical Manual (DSM) of psychiatry. Higher performance status (e.g., at least 80%, or at least 70% using the Karnofsky scoring system) may indicate treatment to prevent progression of the disease state, and enhance the subject's ability to accept therapy and/or radiation treatment. For example, in these embodiments, the subject is ambulatory and capable of self-care. In other embodiments, the evaluation is indicative of a subject with a low performance status (e.g., less than 50%, less than 30%, or less than 20% using the Karnofsky scoring system), so as to allow conventional radiotherapy and/or therapy to be tolerated. In these embodiments, the subject is largely confined to bed or chair and is disabled even for self-care.

The Karnofsky score runs from 100 to 0, where 100 is "perfect" health and 0 is death. The score may be employed at intervals of 10, where: 100% is normal, no complaints, no signs of disease; 90% is capable of normal activity, few symptoms or signs of disease, 80% is normal activity with some difficulty, some symptoms or signs; 70% is caring for self, not capable of normal activity or work; 60% is requiring some help, can take care of most personal requirements; 50% requires help often, requires frequent medical care; 40% is disabled, requires special care and help; 30% is severely disabled, hospital admission indicated but no risk of death; 20% is very ill, urgently requiring admission, requires supportive measures or treatment; and 10% is moribund, rapidly progressive fatal disease processes.

The Zubrod scoring system for performance status includes: 0, fully active, able to carry on all pre-disease performance without restriction; 1, restricted in physically strenuous activity but ambulatory and able to carry out work of a light or sedentary nature, e.g., light house work, office work; 2, ambulatory and capable of all self-care but unable to carry out any work activities, up and about more than 50% of waking hours; 3, capable of only limited self-care, confined to bed or chair more than 50% of waking hours; 4, completely disabled, cannot carry on any self-care, totally confined to bed or chair; 5, dead.

In further embodiments, the clinical factor is histological subclass. In some embodiments, histological samples of tumors are graded according to Elston & Ellis, Histopathology, 1991, 19:403-10, the contents of which are hereby incorporated by reference in their entirety.

In some embodiments, the clinical factor is gender. In one embodiment, the gender is male. In another embodiment the gender is female.

In some embodiments, the clinical factor is disease stage. By way of example, using the overall stage grouping, Stage I cancers are localized to one part of the body; Stage II cancers are locally advanced, as are Stage III cancers. Whether a cancer is designated as Stage II or Stage III can depend on the specific type of cancer. In one example, Hodgkin's disease, Stage II indicates affected lymph nodes on only one side of the diaphragm, whereas Stage III indicates affected lymph nodes above and below the diaphragm. The specific criteria for Stages II and III therefore differ according to diagnosis. Stage IV cancers have often metastasized, spread to other organs, or spread throughout the body.

In some embodiments, the clinical factor is the French-American-British (FAB) classification system for hematologic diseases (e.g. indicating the presence of dysmyelopoiesis and the quantification of myeloblasts and erythroblasts). In one embodiment, the FAB for acute lymphoblastic leukemias is L1-L3, or for acute myeloid leukemias is M0-M7. Further, in some embodiments, the any one of the following clinical factors may be useful in the methods described herein: gender; genetic risk factors; family history; personal history; race and ethnicity; features of the certain tissues; various benign conditions (e.g. non-proliferative lesions); previous chest radiation; carcinogen exposure and the like.

In another embodiment, the method further comprises a measurement of an additional biomarker selected from mutational status, single nucleotide polymorphisms, steady state protein levels, and dynamic protein levels, which can add further specificity and/or sensitivity. In some embodiments, the measurement of an additional biomarker can be measurement of one or more of a cell surface marker CD33, a cell surface marker CD34, a FLT3 mutation status, a p53 mutation status, a phosphorylation state of MEK-1 kinase and phosphorylation of serine at position 70 of Bcl-2. In some embodiments, the biomarker is expression levels of the cytokines, including, for example, interleukin-6. In another embodiments, the biomarker is a mutation in one or more of the genes MLL, AML/ETO, Flt3-ITD, NPM1 (NPMc+), CEBPI, IDH1, IDH2, RUNX1, ras, and WT1 and/or in the epigenetic modifying genes TET2 and ASXL. In further embodiments, the measurement of the biomarker indicates a change in the cell signaling protein profile.

In some cancers, such as Wilms tumor and retinoblastoma, for example, gene deletions or inactivations are responsible for initiating cancer progression, as chromosomal regions associated with tumor suppressors are commonly deleted or mutated. For example, deletions, inversions, and translocations are commonly detected in chromosome region 9p21 in gliomas, non-small-cell lung cancers, leukemias, and melanomas. Without wishing to be bound by theory, these chromosomal changes may inactivate the tumor suppressor cyclin-dependent kinase inhibitor 2A. Along with these deletions of specific genes, large portions of chromosomes can also be lost. For instance, chromosomes 1p and 16q are commonly lost in solid tumor cells. Gene duplications and increases in gene copy numbers can also contribute to cancer and can be detected with transcriptional analysis or copy number variation arrays. For example, the chromosomal region 12q13-q14 is amplified in many sarcomas. This chromosomal region encodes a binding protein called MDM2, which is known to bind to a tumor suppressor called p53. When MDM2 is amplified, it prevents p53 from regulating cell growth, which can result in tumor formation. Further, certain breast cancers are associated with overexpression and increases in copy number of the human epidermal growth factor receptor 2 (ERBB2) gene. Also, gains in chromosomal number, such as chromosomes 1 q and 3q, are also associated with increased cancer risk.

In various embodiments, the present methods further comprise evaluating a presence, absence, or level of a protein and/or a nucleic acid, such as when measuring a biomarker. In various embodiments, the present methods further comprise evaluating a presence, absence, or level of a protein and/or a nucleic acid which can enhance the specificity and/or sensitivity of the sensitivity profiling. In some embodiments, the evaluating is of a marker for subject response. In some embodiments, the present methods comprise measurement using one or more of immunohistochemical staining, western blotting, in cell western, immunofluorescent staining, ELISA, and fluorescent activating cell sorting (FACS), or any other method described herein or known in the art. The present methods may comprise contacting an antibody with a tumor specimen (e.g. biopsy or tissue or body fluid) to identify an epitope that is specific to the tissue or body fluid and that is indicative of a state of a cancer.

In various embodiments, antibodies include whole antibodies and/or any antigen binding fragment (e.g., an antigen-binding portion) and/or single chains of these (e.g. an antibody comprising at least two heavy (H) chains and two light (L) chains inter-connected by disulfide bonds, an Fab fragment, a monovalent fragment consisting of the VL, VH, CL and CH1 domains; a F(ab)2 fragment, a bivalent fragment including two Fab fragments linked by a disulfide bridge at the hinge region; a Fd fragment consisting of the VH and CH1 domains; a FIT fragment consisting of the VL and VH domains of a single arm of an antibody; and the like). In various embodiments, polyclonal and monoclonal antibodies are useful, as are isolated human or humanized antibodies, or functional fragments thereof.

There are generally two strategies used for detection of epitopes on antigens in body fluids or tissues, direct methods and indirect methods. The direct method comprises a one-step staining, and may involve a labeled antibody (e.g. FITC conjugated antiserum) reacting directly with the antigen in a body fluid or tissue sample. The indirect method comprises an unlabeled primary antibody that reacts with the body fluid or tissue antigen, and a labeled secondary antibody that reacts with the primary antibody. Labels can include radioactive labels, fluorescent labels, hapten labels such as, biotin, or an enzyme such as horse radish peroxidase or alkaline phosphatase. Methods of conducting these assays are well known in the art. See, e.g., Harlow et al. (Antibodies, Cold Spring Harbor Laboratory, N Y, 1988), Harlow et al. (Using Antibodies, A Laboratory Manual, Cold Spring Harbor Laboratory, N Y, 1999), Virella (Medical Immunology, 6th edition, Informa HealthCare, New York, 2007), and Diamandis et al. (Immunoassays, Academic Press, Inc., New York, 1996). Kits for conducting these assays are commercially available from, for example, Clontech Laboratories, LLC. (Mountain View, Calif.).

Standard assays to evaluate the binding ability of the antibodies toward the target of various species are known in the art, including for example, ELISAs, western blots and RIAs. The binding kinetics (e.g., binding affinity) of antibodies also can be assessed by standard assays known in the art, such as by Biacore analysis.

In another embodiment, the measurement comprises evaluating a presence, absence, or level of a nucleic acid. A person skilled in the art will appreciate that a number of methods can be used to detect or quantify the DNA/RNA levels of appropriate markers.

Gene expression can be measured using, for example, low-to-mid-plex techniques, including reporter gene assays, Northern blot, fluorescent in situ hybridization (FISH), and reverse transcription PCR (RT-PCR). Gene expression can also be measured using, for example, higher-plex techniques, including serial analysis of gene expression (SAGE), DNA microarrays. Tiling array, RNA-Seq/whole transcriptome shotgun sequencing (WTSS), high-throughput sequencing, multiplex PCR, multiplex ligation-dependent probe amplification (MLPA), DNA sequencing by ligation, and Luminex/XMAP. A person skilled in the art will appreciate that a number of methods can be used to detect or quantify the level of RNA products of the biomarkers within a sample, including arrays, such as microarrays, RT-PCR (including quantitative PCR), nuclease protection assays and Northern blot analyses.

In another embodiment, the method further comprises predicting a clinical response in the subject. In another embodiment, the clinical response is at least about one, about two, about three, or about five year progression/event-free survival.

In some embodiments, the methods disclosed herein comprise preventive treatment. For example, administering a treatment to a subject that is likely to be afflicted by cancer in accordance with the methods described herein. In some embodiments, a subject is likely to be afflicted by cancer if the subject is characterized by one or more of a high risk for a cancer, a genetic predisposition to a cancer (e.g. genetic risk factors), a previous episode of a cancer (e.g. new cancers and/or recurrence), a family history of a cancer, exposure to a cancer-inducing agent (e.g. an environmental agent), and pharmacogenomic information (the effect of genotype on the pharmacokinetic, pharmacodynamic or efficacy profile of a therapeutic).

In some embodiments, a subject is likely to be afflicted by cancer if the subject is characterized by a high risk for a cancer. In some embodiments, a subject is likely to be afflicted by cancer if the subject is characterized by a genetic predisposition to a cancer. In some embodiments, a genetic predisposition to a cancer is a genetic clinical factor, as is known in the art. Such clinical factors may include, by way of example, HNPCC, MLH1, MSH2, MSH6, PMS1, PMS2 for at least colon, uterine, small bowel, stomach, urinary tract cancers. In some embodiments, a subject is likely to be afflicted by cancer if the subject is characterized by a previous episode of a cancer. In some embodiments, the subject has been afflicted with 1, 2, 3, 4, 5, or 6, previous episodes of cancer. In some embodiments, a subject is likely to be afflicted by cancer if the subject is characterized by a family history of a cancer. In some embodiments, a parent and/or grandparent and/or sibling and/or aunt/uncle and/or great aunt/great uncle, and/or cousin has been or is afflicted with a cancer. In some embodiments, a subject is likely to be afflicted by cancer if the subject is characterized by exposure to a cancer-inducing agent (e.g. an environmental agent). For example, exposing skin to strong sunlight is a clinical factor for skin cancer. By way of example, smoking is a clinical factor for cancers of the lung, mouth, larynx, bladder, kidney, and several other organs.

Embodiments of this invention are further illustrated by the following non-limiting examples.

EXAMPLES

Example 1

Whole Cell Assay Using Profiling Peptides in Permeabilized and Non-Permeabilized Cells Briefly, frozen MOLM-13 and OCI-AML3 cell stocks were rapidly thawed, and cell viability was determined by Trypan Blue exclusion. Cells were washed in PBS and resuspended in DTEB (or MEB) buffer (135 mM Trehalose [or 150 mM Mannitol], 10 mM HEPES, 50 mM KCl, 20 µM EGTA, 20 µM EDTA, 0.1% BSA, and 5 mM succinate). The profiling peptides and NOXA (AELPPEFAAQLRKIGDK-VYC; SEQ ID NO:16) were reconstituted in water to make working solutions allowing for final concentrations of: SEQ ID NO:1 (100 µM), SEQ ID NO:14 (100 µM), SEQ ID NO:15 (100 µM), and NOXA (100 µM). DMSO and FCCP (50 µM) were used as negative and positive peptide controls. Profiling peptides, controls, or NOXA (for comparison purposes) were first added to a microplate. Cells ($4 \times 10^5$) resuspended in DTEB or MEB buffers were then added to a staining solution (20 mg/mL oligomycin, 50 mg/mL digitonin, 40 µM JC-1, 1 M 2-mercaptoethanol, DTEB or MEB buffer), before being added to the wells of the microplate in the above (for non-digitonin-treated samples, digitonin was not added to the staining solution above). The mixture was then incubated for up to 2 hours at 30° C., in order for cell permeabilization (if needed), delivery of peptides or compounds, and mitochondrial depolarization to occur. Fluorescence signal of each well was assessed using an Envision multilabel plate reader at Ex475/Em530 and Ex530/Em595. Additional cells that were not treated with a peptide, but were treated with digitonin, were stained with propidium iodide (PI) to assess whether cells were effectively permeabilized by the digitonin. The normalized mitochondrial potential of the median JC-1 red fluorescence of the wells was then compared to DMSO (negative) and FCCP (positive) controls. The results of this comparison are shown in FIGS. 1A-1D. FIGS. 1A and 1B show the results from the MOLM-13 cells, and FIGS. 1C and 1D show the results from the OCI-AML3 cells. Additionally, FIGS. 1A and 1C show the results of cells treated with digitonin, and FIGS. 1B and 1D show the results of cells that were not exposed to digitonin. The labels for the graphs correspond as follows: (NC) Negative Control—DMSO; (PC) Positive Control—FCCP; (1) NOXA, (2) SEQ ID NO:1, (3) SEQ ID NO:14, and (4) SEQ ID NO:15.

As can be seen in FIGS. 1A-1D, cell-membrane permeabilization is necessary for the NOXA peptide, commonly used in similar assays, to induce apoptosis. However, the profiling peptides of the present disclosure do not require the use of digitonin. In the absence of digitonin, the profiling peptides of the present disclosure with the cellular uptake moiety appended at the amino-terminus of the Mcl-1 binding domain, SEQ ID NO:14, has superior activity compared to the profiling peptide comprising the Mcl-1 binding domain alone or the profiling peptide with the cellular uptake moiety appended at the carboxy-terminus of the Mcl-1 binding domain, SEQ ID NO:15.

Additionally, the results shown in FIGS. 1A-1D show that the decoupling agent and positive control, FCCP, requires a cell permeabilizing agent, such as digitonin, to efficiently enter the cell and fully initiate mitochondrial outer-membrane permeabilization. Therefore, in the studies in MOLM-13 cells lacking digitonin (FIG. 1B), SEQ ID NO:14 and SEQ ID NO:15 exceeded the activity of the positive control.

The Z-factors for these assays were then assessed. Z-factors are a valuable method for evaluating the reliability of a biological assay. The goal for an assay is for a Z-factor to be 0.5 or higher. Evaluating the signal-to-noise ratios for the sensitivity profiling assays by calculating the Z-factors shows that using the profiling peptides of the present disclosure results in a much more reliable assay (Table 2). Additionally, the removal of the cell permeabilization step markedly improves the signal-to-noise ratio (Table 3).

TABLE 2

Z-factors for NOXA and profiling peptides of the present disclosure.

| Z' (NOXA) | Z' (SEQ ID NO: 1) | Z' (SEQ ID NO: 14) |
| --- | --- | --- |
| −3.4 | 0.32 | 0.50 |

TABLE 3

Z-factors for permeabilized cells and non-permeabilized cells.

| Cell Line | Z' (digitonin) | Z' (no digitonin) |
| --- | --- | --- |
| MOLM13 | −1.1 | 0.6 |
| OCI-AML3 | 0 | 0.6 |

Example 2

Titration of Concentrations of Profiling Peptides

In an effort to assess the concentration of profiling peptides of the present disclosure used in the absence of a cell permeabilization agent such that the Mcl-1 dependency percentage values are comparable to those achieved using NOXA in the presence of a cell permeabilization agent, the following experiment was performed.

Briefly, frozen OCI-AML3 cell stocks were rapidly thawed, and cell viability was determined by Trypan Blue exclusion. Cells were washed in PBS and resuspended in DTEB (or MEB) buffer (135 mM Trehalose [or 150 mM Mannitol], 10 mM HEPES, 50 mM KCl, 20 µM EGTA, 20 µM EDTA, 0.1% BSA, 5 mM succinate). The profiling peptides and NOXA (SEQ ID NO:16) were reconstituted in water to make working solutions allowing for final concentrations of: SEQ ID NO:1 (100 µM), SEQ ID NO:1 (30 µM), SEQ ID NO:1 (10 µM), and NOXA (100 µM). DMSO and FCCP (50 µM) were used as negative and positive peptide controls. Profiling peptides, controls, or NOXA (for comparison purposes) were first added to a microplate. Cells ($4 \times 10^5$) resuspended in DTEB or MEB buffers were then added to a staining solution (20 mg/mL oligomycin, 50 mg/mL digitonin, 40 µM JC-1, 1 M 2-mercaptoethanol, DTEB or MEB buffer), before being added to the wells of the microplate in the above (for non-digitonin-treated samples, digitonin was not added to the staining solution above). The mixture is then incubated for up to 2 hours at 30° C., in order for cell permeabilization (if needed), delivery of peptides or compounds, and mitochondrial depolarization to occur. Fluorescence signal of each well was assessed using an Envision multilabel plate reader at Ex475/Em530 and Ex530/Em595. The median JC-1 red fluorescence of the gated population was then was then used to calculate % dependency as compared to DMSO (negative) and FCCP (positive) controls.

Statistical Analysis: For each peptide, the Mcl-1 dependency percentage was calculated using the following formula that determines the dependency:

$$PP = \left[1 - \left(\frac{Pep - PC}{NC - PC}\right)\right] * 100$$

Where PC is the fluorescence intensity of the positive control, NC is the fluorescence intensity of the negative control, and Pep is the fluorescence intensity of the peptide at the noted concentration.

The results are shown in FIG. 2. The labels for the graphs correspond as follows: (1) NOXA, (2) SEQ ID NO:1-100 µM, (3) SEQ ID NO:1-30 µM, and (4) SEQ ID NO:1-10 µM. As can be seen in FIG. 2, in OCI-AML-3 cells, reducing the concentration of the profiling peptide to 10 µM brings the Mcl-1 dependency percentage to a comparable value of the standard NOXA peptide at 100 µM.

Example 3

Studies Using AML Subject-Based Cohorts

Peripheral blood and bone marrow samples from newly diagnosed subjects with AML are obtained and analyzed by contacting cells from the sample with any one or more of the profiling peptides disclosed herein (e.g., SEQ ID NOS: 1, 14, or 15). Subjects are treated with an alvocidib-containing regimen (e.g., FLAM: alvocidib (Flavopiridol), Ara-C and Mitoxantrone) if Mcl-1 dependency in their sample is above a predetermined amount (e.g., above 5%, 10%, 15%, 20%, 25%, or 30%). A statistically significant percentage of treated subjects (e.g., greater than 75% or even greater than 95%) have a complete response. Complete response is characterized by less than 5% myeloblasts with normal maturation of all cell lines, an ANC 1000/µL and platelet count 100,000/µL, absence of blast in peripheral blood, absence of leukemic cells in the marrow, clearance of cytogenetics associated with disease, and clearance of previous extramedullary disease.

Sensitivity Profiling

Briefly, frozen, extracted leukocyte samples are rapidly thawed, and cell viability determined by Trypan Blue exclusion. Cells are washed in FACS buffer (1×PBS with 2% FBS) and immunophenotyped using fluorescently labeled CD45, CD3, and CD20 monoclonal antibodies. Cells are then resuspended in Newmeyer buffer (10 mM Trehalose, 10 mM HEPES, 80 mM KCl, 20 μM EGTA, 20 μM EDTA, 5 mM succinate, pH 7.4) for the perturbation step. The profiling peptides are diluted in Newmeyer buffer to make working solutions resulting in final concentrations of: SEQ ID NO:1 (100 μM), SEQ ID NO:14 (100 μM), and SEQ ID NO:15 (100 μM). DMSO and BAM-15 are used as negative and positive peptide controls. Oligomycin is added to individual FACS tubes, followed by the profiling peptides. Cells are then added to the FACS tubes and incubated for 2 hours and 15 minutes at room temperature, in order for delivery of peptides and mitochondrial depolarization to occur. After the incubation, JC-1 dye is prepared in Newmeyer buffer and added to directly to the treated cells. After 45 minutes of incubation with JC-1, cells are analyzed on a three laser BD FACSCanto II. AML Blasts will be gated based on three parameters: 1) singlet discrimination based on SSC, 2) CD45 dim and CD3/CD20 negative, and 3) SSC low. The median JC-1 red fluorescence of the gated blast population is used to calculate % depolarization as compared to DMSO (negative) and BAM-15 (positive) controls. Individual Subject cytogenetic risk classification (Favorable, Intermediate, and Adverse) is determined from the Cancer and Leukemia Group B (CALGB) guidelines.

Statistical Analysis: For each peptide, the Mcl-1 dependency percentage is calculated using the following formula that determines the dependency based on the DMSO negative control as completely unprimed and the BAM-15 as a 100% primed reference:

$$PP = \left[1 - \left(\frac{Pep - PC}{NC - PC}\right)\right] * 100$$

Where PC is the AUC of the positive control, NC is the AUC of the negative control, and Pep is the AUC of the peptide.

For analysis, all subjects not classified as CR are treated as non-responders [Minimal Residual Disease (MRD), Partial Remission (PR), and TF (treatment failure)]. Student's t-tests, Mann-Whitney rank-sum non-parametric tests, multi-variate logistic regression, and ROC curve analyses, between the profiling peptides (and other tumor characteristics, such as cytogenetics, etc.) and response, is calculated using GraphPad Prism Version 5.04 and MedCalc Version 14.8.1.

Mitochondrial Profiling of AML Subject Samples Enrolled on FLAM Protocols

The clinical variables obtained from the subjects is compared to response to determine which, if any, of these factors influence whether subjects would respond to the therapies or not. The variable that is expected to have a significant association with CR is the cytogenetic risk factor, where those with adverse classifications being less likely to respond to the therapies. The WBC, history of MDS, and which protocol was followed are potentially significant.

It is expected that the addition of sensitivity profiling to the analysis will greatly increase the ability to identify subjects who would respond to alvocidib, either alone or in combination therapy.

Example 4

Illustrative Assay Procedure

Mononuclear cells are isolated from primary bone marrow aspirates using density-gradient centrifugation. Sample quality is determined using trypan blue exclusion. Cells are then pelleted, blocked in BSA and stained for markers specific to B and T cells, as well as monocyte differentiation markers and blast-specific markers. After staining, cells are pelleted and separated into fluorescent-activated cell sorting (FACS) tubes and treated with either water (negative control), CCCP (positive control) or SEQ ID NO:14 (subject dependency). After 1 hour, DiOC$_6$, a cationic mitochondrial dye is added. One hour later the cells are analyzed via flow cytometry. Blast cells are isolated by gating on the CD45 dim, CD13, CD33, and CD34 high population of each sample. Dependency values are calculated using the median fluorescent intensity (MFI) of DiOC$_6$ in each sample according to the following equation:

$$PP = \left\{\left[1 - \frac{(\text{Peptide } MFI - CCCP\ MFI)}{(\text{H2O } MFI - CCCP\ MFI)}\right]\right\} * 100$$

Example 5

Illustrative Assay Procedure

Figure 3:
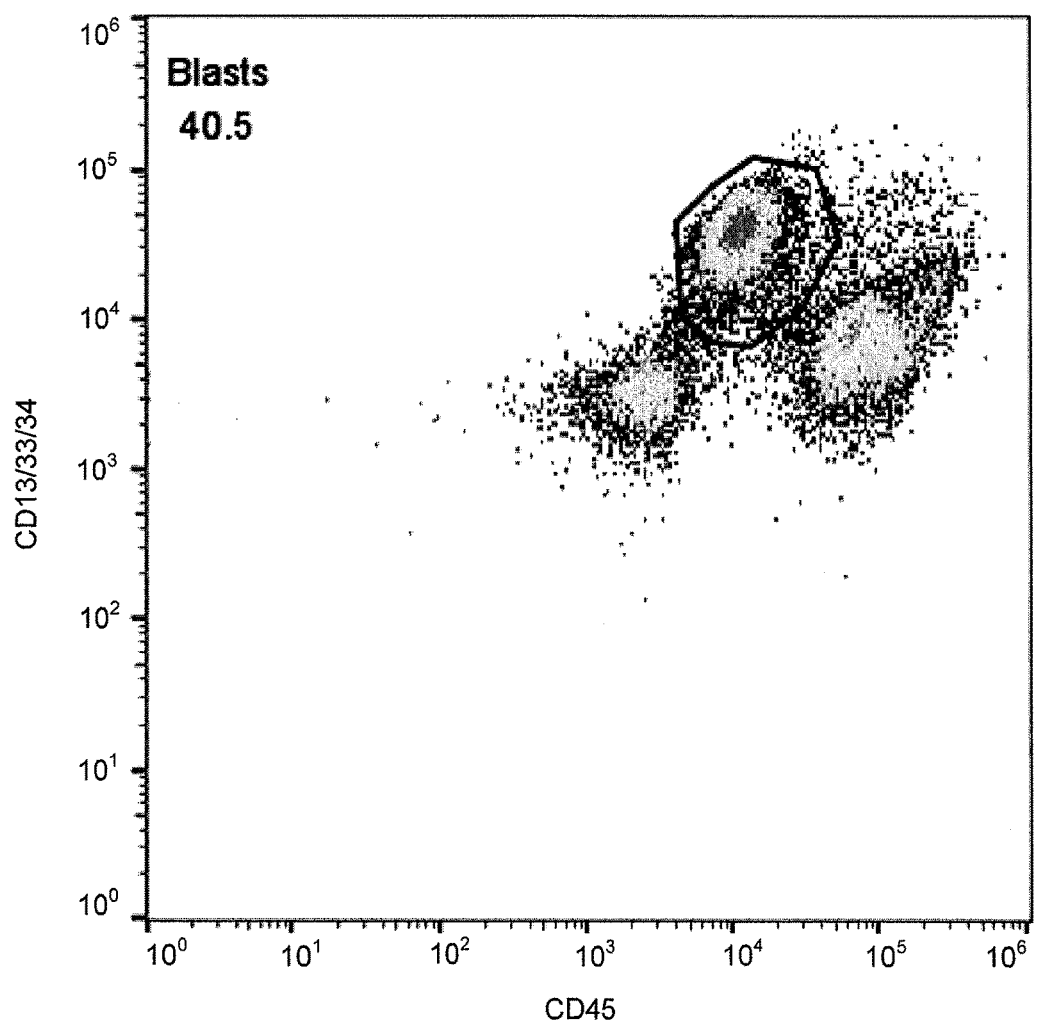
FIG. 3 shows gating for the acute myeloid leukemia (AML) blast cell population using CD45 dim and CD13, CD33 and CD34 high as described in Example 5.

Leukocytes are isolated from primary bone marrow aspirates using ficoll preparation. Leukocytes may be fresh or frozen. If frozen, the sample is thawed prior to testing. Incubate the sample in RPMI with DNase 1 in 37° C. incubator for 60 minutes. Cells are then pelleted, blocked in PBS with 1% BSA for 15 minutes on ice, followed by staining for 30 minutes on ice in the dark. After staining, cells are pelleted and resuspended in DTEB with Ryanodine (30 nM) and Oligomycin. After incubating in a 37° C. incubator for 30 minutes, the sample is separated into fluorescent-activated cell sorting (FACS) tubes and treated with either water (negative control), CCCP (positive control) or SEQ ID NO:14 (subject dependency) and incubated in a 37° incubator for 60 minutes. DiOC$_6$, a cationic mitochondrial dye is then added and incubated for 60 minutes in a 37° C. incubator. The cells are then analyzed via flow cytometry. Blast cells are isolated by gating on the CD45 dim, CD13, CD33 and CD34 high population of each sample. (See FIG. 3). Where indicated, cells may be further gated using CD3 and CD20. Dependency values are calculated using the median fluorescent intensity (MFI) of DiOC$_6$ in each sample according to the following equation:

$$PP = \left\{\left[1 - \frac{(\text{Peptide } MFI - CCCP\ MFI)}{(\text{H2O } MFI - CCCP\ MFI)}\right]\right\} * 100$$

Example 6

Addition of Ryanodine to Assay

Figure 4:
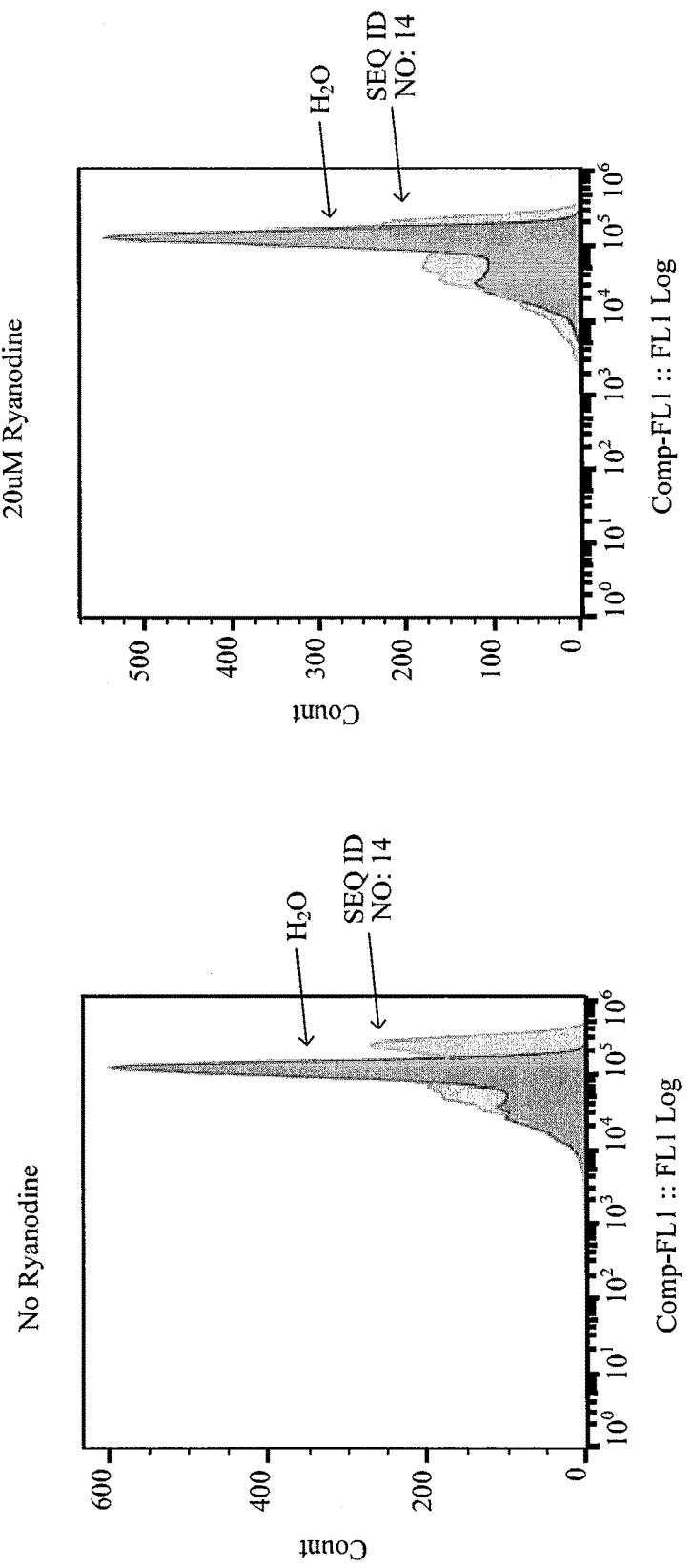
FIG. 4 shows the results of ryanodine testing. Calcium release in MOLM-13 cells treated with the peptide of SEQ ID NO: 14 are shown.

The effects of the addition of ryanodine to the assay described in Example 5, was tested. Ryanodine was added to the assay, and it was determined that this effect was due to Tat-mediated calcium release from the ER and that treatment with 20 nM Ryanodine prevented nonspecific dye uptake. As shown in FIG. 4, the addition of ryanodine reduced non-specificity and allows for an increase in the profiling peptide concentration thereby bringing the assay results into full parity with the NOXA assay results.

Example 7

Comparison of NOXA Priming Assay

NOXA assay results were compared to the results of the assay described in Example 5. Table 4 shows a comparison of NOXA and SEQ ID NO: 14 assay results from cell lines for which NOXA test results have been published (Ishizawa et al. (2015) Mitochondrial Profiling of Acute Myeloid Leukemia in the Assessment of Response to Apoptosis Modulating Drugs. PLoS ONE 10(9): e0138377).

Table 4. Comparison of NOXA Assay Results and SEQ ID NO:14 Assay Results.

TABLE 4

Comparison of NOXA Assay Results and SEQ ID NO: 14 Assay Results.

| Cell Line | NOXA Priming % | SEQ ID NO: 14 Dependency % | Concordance* |
|---|---|---|---|
| MOLM-13 | 19.24 | 20.78 | Y |
| OCI-AML3 | 21.96 | 19.40 | Y |
| THP-1 | 11.28 | 11.70 | Y |
| HL-60 | 7.60 | 24.5 | Y |
| U-937 | 24.35 | 10.1 | Y |
| KG-1 | 12.39 | 0.0 | Y |
| MV4-11 | 12.84 | 5.0 | Y |

*Concordance based on cutoff of ≥40% MCL-1 Dependency for both methods.

Table 5 shows a comparison of NOXA and SEQ ID NO: 14 assay results from subject samples for which NOXA test results have been produced. Of note, Samples 17 through 19 in Table 5 were collected from subjects treated with FLAM and who showed complete response to therapy.

TABLE 5

Comparison of NOXA Assay Results and SEQ ID NO: 14 Assay Results.

| Sample # | Reference Lab NOXA Priming % | Reference Lab NOXA Result (Pos/Neg)* | SEQ ID NO: 14 Dependency % | SEQ ID NO: 14 Result (Pos/Neg) | Concordance* (Y/N) |
|---|---|---|---|---|---|
| 1 | 14.0 | Neg | 18.0 | Neg | Y |
| 2 | 60.0 | Pos | 44.9 | Pos | Y |
| 3 | 16.0 | Neg | 53.8 | Pos | N |
| 4 | 0.0 | Neg | 26.7 | Neg | Y |
| 5 | 94.4 | Pos | 70.8 | Pos | Y |
| 6 | 48.6 | Pos | 44.3 | Pos | Y |
| 7 | 0.0 | Neg | 48.1 | Pos | N |
| 8 | 23.5 | Neg | 17.0 | Neg | Y |

TABLE 5-continued

Comparison of NOXA Assay Results and SEQ ID NO: 14 Assay Results.

| Sample # | Reference Lab NOXA Priming % | Reference Lab NOXA Result (Pos/Neg)* | SEQ ID NO: 14 Dependency % | SEQ ID NO: 14 Result (Pos/Neg) | Concordance* (Y/N) |
|---|---|---|---|---|---|
| 9 | 79.1 | Pos | 71.8 | Pos | Y |
| 10 | 38.0 | Neg | 0.0 | Neg | Y |
| 11 | 43.3 | Pos | 40.6 | Pos | Y |
| 12 | 0.0 | Neg | 38.3 | Neg | Y |
| 13 | 0.0 | Neg | 35.2 | Neg | Y |
| 14 | 0.0 | Neg | 2.6 | Neg | Y |
| 15 | 7.0 | Neg | 0.0 | Neg | Y |
| 16 | 7.0 | Neg | 0.1 | Neg | Y |
| 17 | 10.89 | Neg | 62.4 | Pos | N |
| 18 | 14.43 | Neg | 55.0 | Pos | N |
| 19 | 0.0 | Neg | 27.8 | Neg | Y |

*Concordance based on cutoff of ≥40% MCL-1 Dependency for both methods.

As seen in Table 4 and Table 5, qualitative agreement has been observed for 15 of 19 samples, qualitative agreement is observed for 7 of 7 cell lines with published dependency values, and concordance was observed for 22 of 26 total samples (subject samples and cell lines). The overall observed accuracy was 81% Specificity (17/21 negative samples), and 100% Sensitivity (5/5 positive samples).

As can be seen in Table 5, four samples which originally tested negative subsequently tested positive using the SEQ ID NO: 14 assay. It is believed that these four samples were considered positive due to the improved assay methodology and flow cytometry gating strategy.

Figure 5:
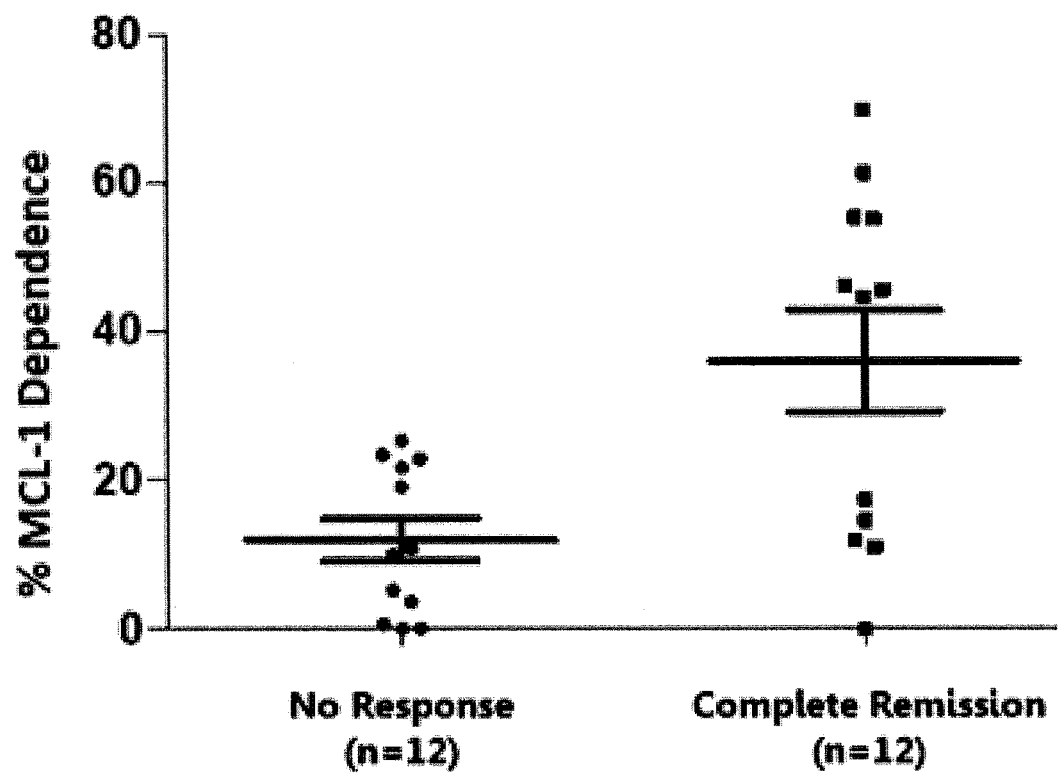
FIG. 5 shows the complete remission (CR) rate in AML subjects with MCL-1 Dependence≥40%.

Results from this study indicate that the SEQ ID NO: 14 assay and the original NOXA assay are greater than 85% concordant when using a cutoff of ≥40% dependency. FIG. 5 shows that the rate of complete response for AML subjects with MCL-1 dependence≥40% is 100%.

Those skilled in the art will recognize, or be able to ascertain, using no more than routine experimentation, numerous equivalents to the specific embodiments described specifically herein. Such equivalents are intended to be encompassed in the scope of certain embodiments.

All of the U.S. patents, U.S. patent application publications, U.S. patent applications, foreign patents, foreign patent applications and non-patent publications referred to in this specification or the attached Application Data Sheet are incorporated herein by reference, in their entirety to the extent not inconsistent with the present description. Aspects of the embodiments can be modified, if necessary to employ concepts of the various patents, applications and publications to provide yet further embodiments. These and other changes can be made to the embodiments in light of the above-detailed description.

From the foregoing it will be appreciated that, although specific embodiments of the invention have been described herein for purposes of illustration, various modifications may be made without deviating from the spirit and scope of the invention. Accordingly, the invention is not limited except as by the appended claims.

What is claimed is:

1. A method for treating a subject with an MCL-1 dependent hematological cancer comprising:
  acquiring bone marrow cells from the subject;
  profiling a plurality of bone marrow cells with a profiling peptide comprising SEQ ID NO: 14;
  determining a Mcl-1 dependency percentage (MDP) of the subject; and
  administering alvocidib to a subject with an MDP determined to be at least 40%.

2. The method of claim 1 wherein the hematologic cancer is multiple myeloma, myelodysplastic syndrome (MDS), or acute myeloid leukemia (AML).

3. The method of claim 1 wherein the cancer is AML.

4. The method of claim 1 wherein the cancer is MDS.

5. The method of claim 1 wherein the cancer is multiple myeloma.

6. The method of claim 1 wherein cytarabine and mitoxantrone are also administered to the subject.

7. The method of claim 1 wherein the profiling is performed in the absence of a permeabilizing agent.

8. A method for treating a subject with an MCL-1 dependent hematological cancer selected from acute myeloid leukemia (AML) and myelodysplastic syndrome (MDS) comprising:
  acquiring bone marrow cells from the subject;
  profiling a plurality of bone marrow cells with a profiling peptide comprising SEQ ID NO: 14;
  determining a Mcl-1 dependency percentage (MDP) of the subject; and
  administering alvocidib to a subject with an MDP determined to be at least 40%.

9. The method of claim 8 wherein the hematological cancer is AML.

10. The method of claim 8 wherein the hematological cancer is MDS.

11. The method of claim 8 wherein the profiling is performed in the absence of a permeabilizing agent.

12. A method for treating a subject having acute myeloid leukemia (AML) comprising:
  acquiring bone marrow cells from the subject;
  profiling a plurality of bone marrow cells with a profiling peptide comprising SEQ ID NO: 14 wherein the profiling is performed in the absence of a permeabilizing agent;
  determining a MCL-1 dependency percentage (MDP) of the subject; and
  administering alvocidib to a subject with an MDP determined to be at least 40%.

13. A method for treating a subject having myelodysplastic syndrome (MDS) comprising:
  acquiring bone marrow cells from the subject;
  profiling a plurality of bone marrow cells with a profiling peptide comprising SEQ ID NO: 14 wherein the profiling is performed in the absence of a permeabilizing agent;
  determining a MCL-1 dependency percentage (MDP) of the subject; and
  administering alvocidib to a subject with an MDP determined to be at least 40%.

\* \* \* \* \*

SEQUENCE LISTING

<160> NUMBER OF SEQ ID NOS: 16

<210> SEQ ID NO 1
<211> LENGTH: 23

```
<212> TYPE: PRT
<213> ORGANISM: Artificial Sequence
<220> FEATURE:
<223> OTHER INFORMATION: Exemplary Mcl-1 Binding Domain sequence

<400> SEQUENCE: 1

Arg Pro Glu Ile Trp Met Thr Gln Gly Leu Arg Arg Leu Gly Asp Glu
1               5                   10                  15

Ile Asn Ala Tyr Tyr Ala Arg
            20

<210> SEQ ID NO 2
<211> LENGTH: 23
<212> TYPE: PRT
<213> ORGANISM: Artificial Sequence
<220> FEATURE:
<223> OTHER INFORMATION: Exemplary Mcl-1 Binding Domain sequence

<400> SEQUENCE: 2

Arg Pro Glu Ile Trp Leu Thr Gln Ser Leu Gln Arg Leu Gly Asp Glu
1               5                   10                  15

Ile Asn Ala Tyr Tyr Ala Arg
            20

<210> SEQ ID NO 3
<211> LENGTH: 23
<212> TYPE: PRT
<213> ORGANISM: Artificial Sequence
<220> FEATURE:
<223> OTHER INFORMATION: Exemplary Mcl-1 Binding Domain sequence

<400> SEQUENCE: 3

Arg Pro Glu Ile Trp Leu Thr Gln His Leu Gln Arg Leu Gly Asp Glu
1               5                   10                  15

Ile Asn Ala Tyr Tyr Ala Arg
            20

<210> SEQ ID NO 4
<211> LENGTH: 23
<212> TYPE: PRT
<213> ORGANISM: Artificial Sequence
<220> FEATURE:
<223> OTHER INFORMATION: Exemplary Mcl-1 Binding Domain sequence

<400> SEQUENCE: 4

Arg Pro Glu Ile Trp Met Gly Gln Gly Leu Arg Arg Leu Gly Asp Glu
1               5                   10                  15

Ile Asn Ala Tyr Tyr Ala Arg
            20

<210> SEQ ID NO 5
<211> LENGTH: 23
<212> TYPE: PRT
<213> ORGANISM: Artificial Sequence
<220> FEATURE:
<223> OTHER INFORMATION: Exemplary Mcl-1 Binding Domain sequence

<400> SEQUENCE: 5

Arg Pro Glu Ile Trp Leu Gly Gln Ser Leu Gln Arg Leu Gly Asp Glu
1               5                   10                  15

Ile Asn Ala Tyr Tyr Ala Arg
            20

<210> SEQ ID NO 6
```

```
<211> LENGTH: 23
<212> TYPE: PRT
<213> ORGANISM: Artificial Sequence
<220> FEATURE:
<223> OTHER INFORMATION: Exemplary Mcl-1 Binding Domain sequence

<400> SEQUENCE: 6

Arg Pro Glu Ile Trp Leu Gly Gln His Leu Gln Arg Leu Gly Asp Glu
 1               5                  10                  15

Ile Asn Ala Tyr Tyr Ala Arg
            20

<210> SEQ ID NO 7
<211> LENGTH: 23
<212> TYPE: PRT
<213> ORGANISM: Artificial Sequence
<220> FEATURE:
<223> OTHER INFORMATION: Exemplary Mcl-1 Binding Domain sequence

<400> SEQUENCE: 7

Arg Pro Glu Ile Trp Ile Thr Gln Glu Leu Arg Arg Ile Gly Asp Glu
 1               5                  10                  15

Phe Asn Ala Tyr Tyr Ala Arg
            20

<210> SEQ ID NO 8
<211> LENGTH: 23
<212> TYPE: PRT
<213> ORGANISM: Artificial Sequence
<220> FEATURE:
<223> OTHER INFORMATION: Exemplary Mcl-1 Binding Domain sequence

<400> SEQUENCE: 8

Arg Pro Glu Ile Trp Met Thr Gln Glu Leu Arg Arg Ile Gly Asp Glu
 1               5                  10                  15

Phe Asn Ala Tyr Tyr Ala Arg
            20

<210> SEQ ID NO 9
<211> LENGTH: 23
<212> TYPE: PRT
<213> ORGANISM: Artificial Sequence
<220> FEATURE:
<223> OTHER INFORMATION: Exemplary Mcl-1 Binding Domain sequence

<400> SEQUENCE: 9

Arg Pro Glu Ile Trp Ile Thr Gln Gly Leu Arg Arg Ile Gly Asp Glu
 1               5                  10                  15

Phe Asn Ala Tyr Tyr Ala Arg
            20

<210> SEQ ID NO 10
<211> LENGTH: 23
<212> TYPE: PRT
<213> ORGANISM: Artificial Sequence
<220> FEATURE:
<223> OTHER INFORMATION: Exemplary Mcl-1 Binding Domain sequence

<400> SEQUENCE: 10

Arg Pro Glu Ile Trp Ile Thr Gln Glu Leu Arg Arg Leu Gly Asp Glu
 1               5                  10                  15

Phe Asn Ala Tyr Tyr Ala Arg
            20
```

```
<210> SEQ ID NO 11
<211> LENGTH: 23
<212> TYPE: PRT
<213> ORGANISM: Artificial Sequence
<220> FEATURE:
<223> OTHER INFORMATION: Exemplary Mcl-1 Binding Domain sequence

<400> SEQUENCE: 11

Arg Pro Glu Ile Trp Ile Thr Gln Glu Leu Arg Arg Ile Gly Asp Glu
1               5                   10                  15

Ile Asn Ala Tyr Tyr Ala Arg
            20

<210> SEQ ID NO 12
<211> LENGTH: 11
<212> TYPE: PRT
<213> ORGANISM: Artificial Sequence
<220> FEATURE:
<223> OTHER INFORMATION: TAT translocation domain

<400> SEQUENCE: 12

Tyr Gly Arg Lys Lys Arg Arg Gln Arg Arg Arg
1               5                   10

<210> SEQ ID NO 13
<211> LENGTH: 16
<212> TYPE: PRT
<213> ORGANISM: Artificial Sequence
<220> FEATURE:
<223> OTHER INFORMATION: ANT translocation domain sequence

<400> SEQUENCE: 13

Arg Gln Ile Lys Ile Trp Phe Gln Asn Arg Arg Met Lys Trp Lys Lys
1               5                   10                  15

<210> SEQ ID NO 14
<211> LENGTH: 37
<212> TYPE: PRT
<213> ORGANISM: Artificial Sequence
<220> FEATURE:
<223> OTHER INFORMATION: profiling peptide sequence

<400> SEQUENCE: 14

Tyr Gly Arg Lys Lys Arg Arg Gln Arg Arg Gly Gly Gly Arg Pro
1               5                   10                  15

Glu Ile Trp Met Thr Gln Gly Leu Arg Arg Leu Gly Asp Glu Ile Asn
            20                  25                  30

Ala Tyr Tyr Ala Arg
        35

<210> SEQ ID NO 15
<211> LENGTH: 37
<212> TYPE: PRT
<213> ORGANISM: Artificial Sequence
<220> FEATURE:
<223> OTHER INFORMATION: profiling peptide sequence

<400> SEQUENCE: 15

Arg Pro Glu Ile Trp Met Thr Gln Gly Leu Arg Arg Leu Gly Asp Glu
1               5                   10                  15

Ile Asn Ala Tyr Tyr Ala Arg Gly Gly Gly Tyr Gly Arg Lys Lys Arg
            20                  25                  30

Arg Gln Arg Arg Arg
        35
```

```
<210> SEQ ID NO 16
<211> LENGTH: 20
<212> TYPE: PRT
<213> ORGANISM: Artificial Sequence
<220> FEATURE:
<223> OTHER INFORMATION: NOXA sequence

<400> SEQUENCE: 16

Ala Glu Leu Pro Pro Glu Phe Ala Ala Gln Leu Arg Lys Ile Gly Asp
 1               5                  10                  15

Lys Val Tyr Cys
            20
```